US011123491B2

(12) United States Patent
Felts et al.

(10) Patent No.: US 11,123,491 B2
(45) Date of Patent: Sep. 21, 2021

(54) CYCLIC OLEFIN POLYMER VESSELS AND VESSEL COATING METHODS

(71) Applicant: SIO2 MEDICAL PRODUCTS, INC., Auburn, AL (US)

(72) Inventors: John T. Felts, Alameda, CA (US); Thomas E. Fisk, Green Valley, AZ (US); Robert S. Abrams, Albany, NY (US); John Ferguson, Auburn, AL (US); Jonathan R. Freedman, Auburn, AL (US); Robert J. Pangborn, Harbor Springs, MI (US); Peter J. Sagona, Pottstown, PA (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 680 days.

(21) Appl. No.: 15/824,775

(22) Filed: Nov. 28, 2017

(65) Prior Publication Data

US 2018/0304020 A1    Oct. 25, 2018

Related U.S. Application Data

(63) Continuation of application No. 13/240,797, filed on Sep. 22, 2011, now Pat. No. 9,878,101.

(60) Provisional application No. 61/413,355, filed on Nov. 12, 2010.

(51) Int. Cl.
*A61M 5/31* (2006.01)
*A61M 5/315* (2006.01)

(52) U.S. Cl.
CPC ....... *A61M 5/3129* (2013.01); *A61M 5/31513* (2013.01); *A61M 2005/3131* (2013.01)

(58) Field of Classification Search
CPC ...... A61J 1/05; A61J 1/062; A61J 1/10; A61J 1/14; A61J 2001/1468
See application file for complete search history.

(56) References Cited

U.S. PATENT DOCUMENTS 3,274,267 A    9/1966    Chow
3,297,465 A    1/1967    Connell
(Continued)

FOREIGN PATENT DOCUMENTS

AT    414209 B    10/2006
AT    504533 A1    6/2008
(Continued)

OTHER PUBLICATIONS

US 5,645,643 A, 07/1997, Thomas (withdrawn)
(Continued)

*Primary Examiner* — Benjamin J Klein
(74) *Attorney, Agent, or Firm* — McAndrews Held & Malloy, Ltd.

(57) ABSTRACT

A package including a vessel wherein at least a portion of the vessel wall is made of a double wall material is disclosed. The double wall material comprises an interior polymer layer enclosed by an exterior polymer layer and one of the polymer layers is a layer made of cyclic olefin polymer (COP) resin. The package comprising the double wall, a CVD coating set on the wall, and a medicament comprising at least one protein, peptide, and/or DNA sequence is disclosed. Methods for processing a vessel, for example to provide lubricity or hydrophobicity, are also disclosed. The interior surface of the seated vessel can be processed via the vessel port by PECVD. Vessel barrier, lubricity and hydrophobic coatings and coated vessels, for example syringes and medical sample collection tubes are disclosed.

17 Claims, 12 Drawing Sheets

(56) References Cited

U.S. PATENT DOCUMENTS

| | | |
|---|---|---|
| 3,355,947 A | 12/1967 | Karlby |
| 3,442,686 A | 5/1969 | Jones |
| 3,448,614 A | 6/1969 | Muger |
| 3,590,634 A | 7/1971 | Pasternak |
| 3,838,598 A | 10/1974 | Tomkins |
| 3,957,653 A | 5/1976 | Blecher |
| 4,111,326 A | 9/1978 | Percarpio |
| 4,134,832 A | 1/1979 | Heimreid |
| 4,136,794 A | 1/1979 | Percapio |
| 4,162,528 A | 7/1979 | Maldonado |
| 4,168,330 A | 9/1979 | Kaganowicz |
| 4,186,840 A | 2/1980 | Percarpio |
| 4,187,952 A | 2/1980 | Percarpio |
| 4,226,333 A | 10/1980 | Percarpio |
| 4,289,726 A | 9/1981 | Potoczky |
| 4,290,534 A | 9/1981 | Percarpio |
| 4,293,078 A | 10/1981 | Percarpio |
| 4,338,764 A | 7/1982 | Percarpio |
| 4,391,128 A | 7/1983 | McWorter |
| 4,392,218 A | 7/1983 | Plunkett, Jr. |
| 4,422,896 A | 12/1983 | Class |
| 4,452,679 A | 6/1984 | Dunn |
| 4,478,873 A | 10/1984 | Masso |
| 4,481,229 A | 11/1984 | Suzuki |
| 4,483,737 A | 11/1984 | Mantel |
| 4,484,479 A | 11/1984 | Eckhardt |
| 4,486,378 A | 12/1984 | Hirata |
| 4,522,510 A | 6/1985 | Rosencwaig |
| 4,524,089 A | 6/1985 | Haque |
| 4,524,616 A | 6/1985 | Drexel |
| 4,552,791 A | 11/1985 | Hahn |
| 4,576,204 A | 3/1986 | Smallborn |
| 4,609,428 A | 9/1986 | Fujimura |
| 4,610,770 A | 9/1986 | Saito |
| 4,648,107 A | 3/1987 | Latter |
| 4,648,281 A | 3/1987 | Morita |
| 4,652,429 A | 3/1987 | Konrad |
| 4,664,279 A | 5/1987 | Obrist |
| 4,667,620 A | 5/1987 | White |
| 4,668,365 A | 5/1987 | Foster |
| 4,683,838 A | 8/1987 | Kimura |
| 4,697,717 A | 10/1987 | Grippi |
| 4,703,187 A | 10/1987 | Hofling |
| 4,716,491 A | 12/1987 | Ohno |
| 4,721,553 A | 1/1988 | Saito |
| 4,725,481 A | 2/1988 | Ostapchenko |
| 4,741,446 A | 5/1988 | Miller |
| 4,756,964 A | 7/1988 | Kincaid |
| 4,767,414 A | 8/1988 | Williams |
| 4,778,721 A | 10/1988 | Sliemers |
| 4,799,246 A | 1/1989 | Fischer |
| 4,808,453 A | 2/1989 | Romberg |
| 4,809,876 A | 3/1989 | Tomaswick |
| 4,824,444 A | 4/1989 | Nomura |
| 4,841,776 A | 6/1989 | Kawachi |
| 4,842,704 A | 6/1989 | Collins |
| 4,844,986 A | 7/1989 | Karakelle |
| 4,846,101 A | 7/1989 | Montgomery |
| 4,853,102 A | 8/1989 | Tateishi |
| 4,869,203 A | 9/1989 | Pinkhasov |
| 4,872,758 A | 10/1989 | Miyazaki |
| 4,874,497 A | 10/1989 | Matsuoka |
| 4,880,675 A | 11/1989 | Mehta |
| 4,883,686 A | 11/1989 | Doehler |
| 4,886,086 A | 12/1989 | Etchells |
| 4,894,256 A | 1/1990 | Gartner |
| 4,894,510 A | 1/1990 | Nakanishi |
| 4,897,285 A | 1/1990 | Wilhelm |
| 4,926,791 A | 5/1990 | Hirose |
| 4,948,628 A | 8/1990 | Montgomery |
| 4,973,504 A | 11/1990 | Romberg |
| 4,991,104 A | 2/1991 | Miller |
| 4,999,014 A | 3/1991 | Gold |
| 5,000,994 A | 3/1991 | Romberg |
| 5,016,564 A | 5/1991 | Nakamura |
| 5,021,114 A | 6/1991 | Saito |
| 5,028,566 A | 7/1991 | Lagendijk |
| 5,030,475 A | 7/1991 | Ackermann |
| 5,032,202 A | 7/1991 | Tsai |
| 5,039,548 A | 8/1991 | Hirose |
| 5,041,303 A | 8/1991 | Wertheimer |
| 5,042,951 A | 8/1991 | Gold |
| 5,044,199 A | 9/1991 | Drexel |
| 5,064,083 A | 11/1991 | Alexander |
| 5,067,491 A | 11/1991 | Taylor |
| 5,079,481 A | 1/1992 | Moslehi |
| 5,082,542 A | 1/1992 | Moslehi |
| 5,084,356 A | 1/1992 | Deak |
| 5,085,904 A | 2/1992 | Deak |
| 5,099,881 A | 3/1992 | Nakajima |
| 5,113,790 A | 5/1992 | Geisler |
| 5,120,966 A | 6/1992 | Kondo |
| 5,131,752 A | 7/1992 | Yu |
| 5,144,196 A | 9/1992 | Gegenwart |
| 5,147,678 A | 9/1992 | Foerch |
| 5,154,943 A | 10/1992 | Etzkorn |
| 5,189,446 A | 2/1993 | Barnes |
| 5,192,849 A | 3/1993 | Moslehi |
| 5,198,725 A | 3/1993 | Chen |
| 5,203,959 A | 4/1993 | Hirose |
| 5,204,141 A | 4/1993 | Roberts |
| 5,209,882 A | 5/1993 | Hattori |
| 5,216,329 A | 6/1993 | Pelleteir |
| 5,224,441 A | 7/1993 | Felts |
| 5,225,024 A | 7/1993 | Hanley |
| 5,232,111 A | 8/1993 | Burns |
| 5,252,178 A | 10/1993 | Moslehi |
| 5,260,095 A | 11/1993 | Affinito |
| 5,266,398 A | 11/1993 | Hioki |
| 5,271,274 A | 12/1993 | Khuri-Yakub |
| 5,272,417 A | 12/1993 | Ohmi |
| 5,272,735 A | 12/1993 | Bryan |
| 5,275,299 A | 1/1994 | Konrad |
| 5,286,297 A | 2/1994 | Moslehi |
| 5,292,370 A | 3/1994 | Tsai |
| 5,294,011 A | 3/1994 | Konrad |
| 5,294,464 A | 3/1994 | Geisler |
| 5,297,561 A | 3/1994 | Hulon |
| 5,298,587 A | 3/1994 | Hu |
| 5,300,901 A | 4/1994 | Krummel |
| 5,302,266 A | 4/1994 | Grabarz |
| 5,308,649 A | 5/1994 | Babacz |
| 5,314,561 A | 5/1994 | Komiya |
| 5,320,875 A | 6/1994 | Hu |
| 5,321,634 A | 6/1994 | Obata |
| 5,330,578 A | 7/1994 | Sakama |
| 5,333,049 A | 7/1994 | Ledger |
| 5,338,579 A | 8/1994 | Ogawa et al. |
| 5,346,579 A | 9/1994 | Cook |
| 5,354,286 A | 10/1994 | Mesa |
| 5,356,029 A | 10/1994 | Hogan |
| 5,361,921 A | 11/1994 | Burns |
| 5,364,665 A | 11/1994 | Felts |
| 5,364,666 A | 11/1994 | Williams |
| 5,372,851 A | 12/1994 | Ogawa et al. |
| 5,374,314 A | 12/1994 | Babacz |
| 5,378,510 A | 1/1995 | Thomas |
| 5,381,228 A | 1/1995 | Brace |
| 5,395,644 A | 3/1995 | Affinito |
| 5,396,080 A | 3/1995 | Hannotiau |
| 5,397,956 A | 3/1995 | Araki |
| 5,409,782 A | 4/1995 | Murayama |
| 5,413,813 A | 5/1995 | Cruse |
| 5,423,915 A | 6/1995 | Murata |
| 5,429,070 A | 7/1995 | Campbell |
| 5,433,786 A | 7/1995 | Hu |
| 5,434,008 A | 7/1995 | Felts |
| 5,439,736 A | 8/1995 | Nomura |
| 5,440,446 A | 8/1995 | Shaw |
| 5,443,645 A | 8/1995 | Otoshi |
| 5,444,207 A | 8/1995 | Sekine |
| 5,449,432 A | 9/1995 | Hanawa |
| 5,452,082 A | 9/1995 | Sanger |
| 5,468,520 A | 11/1995 | Williams |

(56) References Cited

U.S. PATENT DOCUMENTS

| | | |
|---|---|---|
| 5,470,388 A | 11/1995 | Goedicke |
| 5,472,660 A | 12/1995 | Fortin |
| 5,485,091 A | 1/1996 | Verkuil |
| 5,486,701 A | 1/1996 | Norton |
| 5,494,170 A | 2/1996 | Burns |
| 5,494,712 A | 2/1996 | Hu |
| 5,495,958 A | 3/1996 | Konrad |
| 5,508,075 A | 4/1996 | Roulin |
| 5,510,155 A | 4/1996 | Williams |
| 5,513,515 A | 5/1996 | Mayer |
| 5,514,276 A | 5/1996 | Babock |
| 5,521,351 A | 5/1996 | Mahoney |
| 5,522,518 A | 6/1996 | Konrad |
| 5,531,060 A | 7/1996 | Fayet |
| 5,531,683 A | 7/1996 | Kriesel |
| 5,536,253 A | 7/1996 | Haber |
| 5,543,919 A | 8/1996 | Mumola |
| 5,545,375 A | 8/1996 | Tropsha |
| 5,547,508 A | 8/1996 | Affinito |
| 5,547,723 A | 8/1996 | Williams |
| 5,554,223 A | 9/1996 | Imahashi |
| 5,555,471 A | 9/1996 | Xu |
| 5,565,248 A | 10/1996 | Piester |
| 5,569,810 A | 10/1996 | Tsuji |
| 5,571,366 A | 11/1996 | Ishii |
| 5,578,103 A | 11/1996 | Araujo |
| 5,591,898 A | 1/1997 | Mayer |
| 5,593,550 A | 1/1997 | Stewart |
| 5,597,456 A | 1/1997 | Maruyama |
| 5,616,369 A | 4/1997 | Williams |
| 5,620,523 A | 4/1997 | Maeda |
| 5,632,396 A | 5/1997 | Burns |
| 5,633,711 A | 5/1997 | Nelson |
| 5,643,638 A | 7/1997 | Otto |
| 5,652,030 A | 7/1997 | Delperier |
| 5,654,054 A | 8/1997 | Tropsha |
| 5,656,141 A | 8/1997 | Betz |
| 5,658,438 A | 8/1997 | Givens |
| 5,665,280 A | 9/1997 | Tropsha |
| 5,667,840 A | 9/1997 | Tingey |
| 5,674,321 A | 10/1997 | Pu |
| 5,677,010 A | 10/1997 | Esser |
| 5,679,412 A | 10/1997 | Kuehnle |
| 5,679,413 A | 10/1997 | Petrmichl |
| 5,683,771 A | 11/1997 | Tropsha |
| 5,686,157 A | 11/1997 | Harvey |
| 5,690,745 A | 11/1997 | Grunwald |
| 5,691,007 A | 11/1997 | Montgomery |
| 5,693,196 A | 12/1997 | Stewart |
| 5,699,923 A | 12/1997 | Burns |
| 5,702,770 A | 12/1997 | Martin |
| 5,704,983 A | 1/1998 | Thomas et al. |
| 5,716,683 A | 2/1998 | Harvey |
| 5,718,967 A | 2/1998 | Hu |
| 5,725,909 A | 3/1998 | Shaw |
| 5,733,405 A | 3/1998 | Taki |
| 5,736,207 A | 4/1998 | Walther |
| 5,737,179 A | 4/1998 | Shaw |
| 5,738,233 A | 4/1998 | Burns |
| 5,738,920 A | 4/1998 | Knors |
| 5,744,360 A | 4/1998 | Hu |
| 5,750,892 A | 5/1998 | Huang |
| 5,763,033 A | 6/1998 | Tropsha |
| 5,766,362 A | 6/1998 | Montgomery |
| 5,769,273 A | 6/1998 | Sasaki |
| 5,779,074 A | 7/1998 | Burns |
| 5,779,716 A | 7/1998 | Cano |
| 5,779,802 A | 7/1998 | Borghs |
| 5,779,849 A | 7/1998 | Blalock |
| 5,788,670 A | 8/1998 | Reinhard |
| 5,792,940 A | 8/1998 | Ghandhi |
| 5,798,027 A | 8/1998 | Lefebvre |
| 5,800,880 A | 9/1998 | Laurent |
| 5,807,343 A | 9/1998 | Tucker |
| 5,807,605 A | 9/1998 | Tingey |
| 5,812,261 A | 9/1998 | Nelson |
| 5,814,257 A | 9/1998 | Kawata |
| 5,814,738 A | 9/1998 | Pinkerton |
| 5,820,603 A | 10/1998 | Tucker |
| 5,823,373 A | 10/1998 | Sudo |
| 5,824,198 A | 10/1998 | Williams |
| 5,824,607 A | 10/1998 | Trow |
| 5,833,752 A | 11/1998 | Martin |
| 5,837,888 A | 11/1998 | Mayer |
| 5,837,903 A | 11/1998 | Weingand |
| 5,840,167 A | 11/1998 | Kim |
| 5,849,368 A | 12/1998 | Hostettler |
| 5,853,833 A | 12/1998 | Sudo |
| 5,855,686 A | 1/1999 | Rust |
| 5,861,546 A | 1/1999 | Sagi |
| 5,871,700 A | 2/1999 | Konrad |
| 5,877,895 A | 3/1999 | Shaw |
| 5,880,034 A | 3/1999 | Keller |
| 5,888,414 A | 3/1999 | Collins |
| 5,888,591 A | 3/1999 | Gleason |
| 5,897,508 A | 4/1999 | Konrad |
| 5,900,284 A | 5/1999 | Hu |
| 5,900,285 A | 5/1999 | Walther |
| 5,902,461 A | 5/1999 | Xu |
| 5,904,952 A | 5/1999 | Lopata |
| 5,913,140 A | 6/1999 | Roche |
| 5,914,189 A | 6/1999 | Hasz |
| 5,919,328 A | 7/1999 | Tropsha |
| 5,919,420 A | 7/1999 | Niermann |
| 5,935,391 A | 8/1999 | Nakahigashi |
| 5,945,187 A | 8/1999 | Such-Rasmussen |
| 5,951,527 A | 9/1999 | Sudo |
| 5,952,069 A | 9/1999 | Tropsha |
| 5,955,161 A | 9/1999 | Tropsha |
| 5,961,911 A | 10/1999 | Hwang |
| 5,968,620 A | 10/1999 | Harvey |
| 5,972,297 A | 10/1999 | Niermann |
| 5,972,436 A | 10/1999 | Walther |
| 5,985,103 A | 11/1999 | Givens |
| 6,001,429 A | 12/1999 | Martin |
| 6,009,743 A | 1/2000 | Mayer |
| 6,013,337 A | 1/2000 | Knors |
| 6,017,317 A | 1/2000 | Newby |
| 6,018,987 A | 2/2000 | Mayer |
| 6,020,196 A | 2/2000 | Hu |
| 6,027,619 A | 2/2000 | Cathey |
| 6,032,813 A | 3/2000 | Niermann |
| 6,035,717 A | 3/2000 | Carodiskey |
| 6,050,400 A | 4/2000 | Taskis |
| 6,051,151 A | 4/2000 | Keller |
| 6,054,016 A | 4/2000 | Tuda |
| 6,054,188 A | 4/2000 | Tropsha |
| 6,068,884 A | 5/2000 | Rose |
| 6,077,403 A | 6/2000 | Kobayashi |
| 6,081,330 A | 6/2000 | Nelson |
| 6,082,295 A | 7/2000 | Lee |
| 6,083,313 A | 7/2000 | Venkatraman et al. |
| 6,085,927 A | 7/2000 | Kusz |
| 6,090,081 A | 7/2000 | Sudo |
| 6,106,678 A | 8/2000 | Shufflebotham |
| 6,110,395 A | 8/2000 | Gibson, Jr. |
| 6,110,544 A | 8/2000 | Yang |
| 6,112,695 A | 9/2000 | Felts |
| 6,116,081 A | 9/2000 | Ghandhi |
| 6,117,243 A | 9/2000 | Walther |
| 6,118,844 A | 9/2000 | Fischer |
| 6,124,212 A | 9/2000 | Fan |
| 6,125,687 A | 10/2000 | McClelland |
| 6,126,640 A | 10/2000 | Tucker |
| 6,136,275 A | 10/2000 | Niermann |
| 6,139,802 A | 10/2000 | Niermann |
| 6,143,140 A | 11/2000 | Wang |
| 6,149,982 A | 11/2000 | Plester |
| 6,153,269 A | 11/2000 | Gleason |
| 6,156,152 A | 12/2000 | Ogino |
| 6,156,399 A | 12/2000 | Spallek |
| 6,156,435 A | 12/2000 | Gleason |
| 6,160,350 A | 12/2000 | Sakemi |
| 6,161,712 A | 12/2000 | Savitz |

(56) References Cited

U.S. PATENT DOCUMENTS

| | | | |
|---|---|---|---|
| 6,163,006 A | 12/2000 | Doughty |
| 6,165,138 A | 12/2000 | Miller |
| 6,165,542 A | 12/2000 | Jaworowski |
| 6,165,566 A | 12/2000 | Tropsha |
| 6,171,670 B1 | 1/2001 | Sudo |
| 6,175,612 B1 | 1/2001 | Sato |
| 6,177,142 B1 | 1/2001 | Felts |
| 6,180,185 B1 | 1/2001 | Felts |
| 6,180,191 B1 | 1/2001 | Felts |
| 6,188,079 B1 | 2/2001 | Juvinall |
| 6,189,484 B1 | 2/2001 | Yin |
| 6,190,992 B1 | 2/2001 | Sandhu |
| 6,193,853 B1 | 2/2001 | Yumshtyk |
| 6,196,155 B1 | 3/2001 | Setoyama |
| 6,197,166 B1 | 3/2001 | Moslehi |
| 6,200,658 B1 | 3/2001 | Walther |
| 6,200,675 B1 | 3/2001 | Neerinck |
| 6,204,922 B1 | 3/2001 | Chalmers |
| 6,210,791 B1 | 4/2001 | Skoog |
| 6,213,985 B1 | 4/2001 | Niedospial |
| 6,214,422 B1 | 4/2001 | Yializis |
| 6,217,716 B1 | 4/2001 | Fai Lai |
| 6,223,683 B1 | 5/2001 | Plester |
| 6,236,459 B1 | 5/2001 | Negandaripour |
| 6,245,190 B1 | 6/2001 | Masuda |
| 6,248,219 B1 | 6/2001 | Wellerdieck |
| 6,248,397 B1 | 6/2001 | Ye |
| 6,251,792 B1 | 6/2001 | Collins |
| 6,254,983 B1 | 7/2001 | Namiki |
| 6,261,643 B1 | 7/2001 | Hasz |
| 6,263,249 B1 | 7/2001 | Stewart |
| 6,271,047 B1 | 8/2001 | Ushio |
| 6,276,296 B1 | 8/2001 | Plester |
| 6,277,331 B1 | 8/2001 | Konrad |
| 6,279,505 B1 | 8/2001 | Plester |
| 6,284,986 B1 | 9/2001 | Dietze |
| 6,306,132 B1 | 10/2001 | Moorman |
| 6,308,556 B1 | 10/2001 | Sagi |
| 6,322,661 B1 | 11/2001 | Bailey, III |
| 6,331,174 B1 * | 12/2001 | Reinhard ............... A61M 5/28 |
| | | 427/2.3 |
| 6,346,596 B1 | 2/2002 | Mallen |
| 6,348,967 B1 | 2/2002 | Nelson |
| 6,350,415 B1 | 2/2002 | Niermann |
| 6,351,075 B1 | 2/2002 | Barankova |
| 6,352,629 B1 | 3/2002 | Wang |
| 6,354,452 B1 | 3/2002 | DeSalvo |
| 6,355,033 B1 | 3/2002 | Moorman |
| 6,365,013 B1 | 4/2002 | Beele |
| 6,375,022 B1 | 4/2002 | Zurcher |
| 6,376,028 B1 | 4/2002 | Laurent |
| 6,379,757 B1 | 4/2002 | Iacovangelo |
| 6,382,441 B1 | 5/2002 | Carano |
| 6,394,979 B1 | 5/2002 | Sharp |
| 6,396,024 B1 | 5/2002 | Doughty |
| 6,399,944 B1 | 6/2002 | Vasilyev |
| 6,402,885 B2 | 6/2002 | Loewenhardt |
| 6,410,926 B1 | 6/2002 | Munro |
| 6,413,645 B1 | 7/2002 | Graff |
| 6,432,494 B1 | 8/2002 | Yang |
| 6,432,510 B1 | 8/2002 | Kim |
| 6,470,650 B1 | 10/2002 | Lohwasser |
| 6,471,822 B1 | 10/2002 | Yin |
| 6,475,622 B2 | 11/2002 | Namiki |
| 6,482,509 B2 | 11/2002 | Buch-Rasmussen et al. |
| 6,486,081 B1 | 11/2002 | Ishikawa |
| 6,500,500 B1 | 12/2002 | Okamura |
| 6,503,579 B1 | 1/2003 | Murakami |
| 6,518,195 B1 | 2/2003 | Collins |
| 6,524,448 B2 | 2/2003 | Brinkmann |
| 6,539,890 B1 | 4/2003 | Felts |
| 6,544,610 B1 | 4/2003 | Minami |
| 6,551,267 B1 | 4/2003 | Cohen |
| 6,558,679 B2 | 5/2003 | Flament-Garcia et al. |
| 6,562,189 B1 | 5/2003 | Quiles |
| 6,565,791 B1 | 5/2003 | Laurent |
| 6,582,426 B2 | 6/2003 | Moorman |
| 6,582,823 B1 | 6/2003 | Sakhrani et al. |
| 6,584,828 B2 | 7/2003 | Sagi |
| 6,595,961 B2 | 7/2003 | Hetzler |
| 6,597,193 B2 | 7/2003 | Lagowski |
| 6,599,569 B1 | 7/2003 | Humele |
| 6,599,594 B1 | 7/2003 | Walther |
| 6,602,206 B1 | 8/2003 | Niermann |
| 6,616,632 B2 | 9/2003 | Sharp |
| 6,620,139 B1 | 9/2003 | Plicchi |
| 6,620,334 B2 | 9/2003 | Kanno |
| 6,623,861 B2 | 9/2003 | Martin |
| 6,638,403 B1 | 10/2003 | Inaba |
| 6,638,876 B2 | 10/2003 | Levy |
| 6,645,354 B1 | 11/2003 | Gorokhovsky |
| 6,651,835 B2 | 11/2003 | Iskra |
| 6,652,520 B2 | 11/2003 | Moorman |
| 6,656,540 B2 | 12/2003 | Sakamoto |
| 6,658,919 B2 | 12/2003 | Chatard |
| 6,662,957 B2 | 12/2003 | Zurcher |
| 6,663,601 B2 | 12/2003 | Hetzler |
| 6,670,200 B2 | 12/2003 | Ushio |
| 6,673,199 B1 | 1/2004 | Yamartino |
| 6,680,091 B2 * | 1/2004 | Buch-Rasmussen ... A61J 1/062 |
| | | 428/35.7 |
| 6,680,621 B2 | 1/2004 | Savtchouk |
| 6,683,308 B2 | 1/2004 | Itagaki |
| 6,684,683 B2 | 2/2004 | Potyrailo |
| 6,702,898 B2 | 3/2004 | Hosoi |
| 6,706,412 B2 | 3/2004 | Yializis |
| 6,746,430 B2 | 6/2004 | Lubrecht |
| 6,749,078 B2 | 6/2004 | Iskra |
| 6,752,899 B1 | 6/2004 | Singh |
| 6,753,972 B1 | 6/2004 | Hirose |
| 6,757,056 B1 | 6/2004 | Meeks |
| 6,764,714 B2 | 7/2004 | Wei |
| 6,765,466 B2 | 7/2004 | Miyata |
| 6,766,682 B2 | 7/2004 | Engle |
| 6,774,018 B2 | 8/2004 | Mikhael |
| 6,796,780 B1 | 9/2004 | Chatard |
| 6,800,852 B2 | 10/2004 | Larson |
| 6,808,753 B2 | 10/2004 | Rule |
| 6,810,106 B2 | 10/2004 | Sato |
| 6,815,014 B2 | 11/2004 | Gabelnick |
| 6,818,310 B2 | 11/2004 | Namiki |
| 6,827,972 B2 | 12/2004 | Darras |
| 6,837,954 B2 | 1/2005 | Carano |
| 6,844,075 B1 | 1/2005 | Saak |
| 6,853,141 B2 | 2/2005 | Hoffman |
| 6,858,259 B2 | 2/2005 | Affinito |
| 6,863,731 B2 | 3/2005 | Elsayed-Ali |
| 6,864,773 B2 | 3/2005 | Perrin |
| 6,866,656 B2 | 3/2005 | Tingey |
| 6,872,428 B2 | 3/2005 | Yang |
| 6,876,154 B2 | 4/2005 | Appleyard |
| 6,885,727 B2 | 4/2005 | Tamura |
| 6,887,578 B2 | 5/2005 | Gleason |
| 6,891,158 B2 | 5/2005 | Larson |
| 6,892,567 B1 | 5/2005 | Morrow |
| 6,899,054 B1 | 5/2005 | Bardos |
| 6,905,769 B2 | 6/2005 | Komada |
| 6,910,597 B2 | 6/2005 | Iskra |
| 6,911,779 B2 | 6/2005 | Madocks |
| 6,919,107 B2 | 7/2005 | Schwarzenbach |
| 6,919,114 B1 | 7/2005 | Darras |
| 6,933,460 B2 | 8/2005 | Vanden Brande |
| 6,946,164 B2 | 9/2005 | Huang |
| 6,952,949 B2 | 10/2005 | Moore |
| 6,960,393 B2 | 11/2005 | Yializis |
| 6,962,671 B2 | 11/2005 | Martin |
| 6,965,221 B2 | 11/2005 | Lipcsei |
| 6,981,403 B2 | 1/2006 | Ascheman |
| 6,989,675 B2 | 1/2006 | Kesil |
| 6,995,377 B2 | 2/2006 | Darr |
| 7,029,755 B2 | 4/2006 | Terry |
| 7,029,803 B2 | 4/2006 | Becker |
| 7,039,158 B1 | 5/2006 | Janik |
| 7,052,736 B2 | 5/2006 | Wei |

(56) References Cited

U.S. PATENT DOCUMENTS

| | | |
|---|---|---|
| 7,052,920 B2 | 5/2006 | Ushio |
| 7,059,268 B2 | 6/2006 | Russell |
| 7,067,034 B2 | 6/2006 | Bailey, III |
| 7,074,501 B2 | 7/2006 | Czeremuszkin |
| 7,098,453 B2 | 8/2006 | Ando |
| 7,109,070 B2 | 9/2006 | Behle |
| 7,112,352 B2 | 9/2006 | Schaepkens |
| 7,112,541 B2 | 9/2006 | Xia |
| 7,115,310 B2 | 10/2006 | Jacoud |
| 7,118,538 B2 | 10/2006 | Konrad |
| 7,119,908 B2 | 10/2006 | Nomoto |
| 7,121,135 B2 | 10/2006 | Moore |
| 7,130,373 B2 | 10/2006 | Omote |
| 7,150,299 B2 | 12/2006 | Hertzler |
| 7,160,292 B2 | 1/2007 | Moorman |
| 7,180,849 B2 | 2/2007 | Hirokane |
| 7,183,197 B2 | 2/2007 | Won |
| 7,188,734 B2 | 3/2007 | Konrad |
| 7,189,218 B2 | 3/2007 | Lichtenberg |
| 7,189,290 B2 | 3/2007 | Hama |
| 7,193,724 B2 | 3/2007 | Isei |
| 7,198,685 B2 | 4/2007 | Hetzler |
| 7,206,074 B2 | 4/2007 | Fujimoto |
| 7,244,381 B2 | 7/2007 | Chatard |
| 7,253,892 B2 | 8/2007 | Semersky |
| 7,286,242 B2 | 10/2007 | Kim |
| 7,288,293 B2 | 10/2007 | Koulik |
| 7,297,216 B2 | 11/2007 | Hetzler |
| 7,297,640 B2 | 11/2007 | Xie |
| 7,300,684 B2 | 11/2007 | Boardman |
| 7,303,789 B2 | 12/2007 | Saito |
| 7,303,790 B2 | 12/2007 | Delaunay |
| 7,306,852 B2 | 12/2007 | Komada |
| 7,332,227 B2 | 2/2008 | Hardman |
| 7,338,576 B2 | 3/2008 | Ono |
| 7,339,682 B2 | 3/2008 | Aiyer |
| 7,344,766 B1 | 3/2008 | Sorensen |
| 7,348,055 B2 | 3/2008 | Chappa |
| 7,348,192 B2 | 3/2008 | Mikami |
| 7,362,425 B2 | 4/2008 | Meeks |
| 7,381,469 B2 | 6/2008 | Moelle |
| 7,390,573 B2 | 6/2008 | Korevaar |
| 7,399,500 B2 | 7/2008 | Bicker |
| 7,404,278 B2 | 7/2008 | Wittland |
| 7,405,008 B2 | 7/2008 | Domine |
| 7,409,313 B2 | 8/2008 | Ringermacher |
| 7,411,685 B2 | 8/2008 | Takashima |
| RE40,531 E | 10/2008 | Graff |
| 7,431,989 B2 | 10/2008 | Sakhrani |
| 7,438,783 B2 | 10/2008 | Miyata |
| 7,444,955 B2 | 11/2008 | Boardman |
| 7,455,892 B2 | 11/2008 | Goodwin |
| 7,480,363 B2 | 1/2009 | Lasiuk |
| 7,488,683 B2 | 2/2009 | Kobayashi |
| 7,494,941 B2 | 2/2009 | Kasahara |
| 7,507,378 B2 | 3/2009 | Reichenbach |
| 7,513,953 B1 | 4/2009 | Felts |
| 7,520,965 B2 | 4/2009 | Wei |
| 7,521,022 B2 | 4/2009 | Konrad |
| 7,534,615 B2 | 5/2009 | Havens |
| 7,534,733 B2 | 5/2009 | Bookbinder |
| RE40,787 E | 6/2009 | Martin |
| 7,541,069 B2 | 6/2009 | Tudhope |
| 7,552,620 B2 | 6/2009 | DeRoos |
| 7,553,529 B2 | 6/2009 | Sakhrani |
| 7,555,934 B2 | 7/2009 | DeRoos |
| 7,569,035 B1 | 8/2009 | Wilmot |
| 7,571,122 B2 | 8/2009 | Howes |
| 7,579,056 B2 | 8/2009 | Brown |
| 7,586,824 B2 | 9/2009 | Hirokane |
| 7,582,868 B2 | 9/2009 | Jiang |
| 7,595,097 B2 | 9/2009 | Iacovangelo |
| 7,608,151 B2 | 10/2009 | Tudhope |
| 7,609,605 B2 | 10/2009 | Hirokane |
| 7,618,686 B2 | 11/2009 | Colpo |
| 7,624,622 B1 | 12/2009 | Mayer |
| 7,625,494 B2 | 12/2009 | Honda |
| 7,641,636 B2 | 1/2010 | Moesli |
| 7,645,696 B1 | 1/2010 | Dulkin |
| 7,648,481 B2 | 1/2010 | Geiger |
| 7,648,762 B2 | 1/2010 | Sohn |
| 7,682,816 B2 | 3/2010 | Kim |
| 7,694,403 B2 | 4/2010 | Moulton |
| 7,699,933 B2 | 4/2010 | Lizenberg |
| 7,704,683 B2 | 4/2010 | Wittenberg |
| 7,713,638 B2 | 5/2010 | Moelle |
| 7,736,689 B2 | 6/2010 | Chappa |
| 7,740,610 B2 | 6/2010 | Moh |
| 7,744,567 B2 | 6/2010 | Glowacki |
| 7,744,790 B2 | 6/2010 | Behle |
| 7,745,228 B2 | 6/2010 | Schwind |
| 7,745,547 B1 | 6/2010 | Auerbach |
| 7,749,914 B2 | 7/2010 | Honda |
| 7,754,302 B2 | 7/2010 | Yamaski |
| 7,766,882 B2 | 8/2010 | Sudo |
| 7,780,866 B2 | 8/2010 | Miller |
| 7,785,862 B2 | 8/2010 | Kim |
| 7,790,475 B2 | 9/2010 | Galbraith |
| 7,798,993 B2 | 9/2010 | Lim |
| 7,803,305 B2 | 9/2010 | Ahem |
| 7,807,242 B2 | 10/2010 | Sorensen |
| 7,810,448 B2 | 10/2010 | Behle |
| 7,811,384 B2 | 10/2010 | Bicker |
| 7,815,922 B2 | 10/2010 | Chaney |
| 7,846,293 B2 | 12/2010 | Iwasaki |
| 7,854,889 B2 | 12/2010 | Perot |
| 7,867,366 B1 | 1/2011 | McFarland |
| 7,901,783 B2 | 3/2011 | Rose |
| 7,905,866 B2 | 3/2011 | Haider |
| 7,922,880 B1 | 4/2011 | Pradhan |
| 7,922,958 B2 | 4/2011 | D'Arrigo |
| 7,926,446 B2 | 4/2011 | Behle |
| 7,931,955 B2 | 4/2011 | Behle |
| 7,932,678 B2 | 4/2011 | Madocks |
| 7,934,613 B2 | 5/2011 | Sudo |
| 7,943,205 B2 | 5/2011 | Schaepkens |
| 7,947,337 B2 | 5/2011 | Kuepper |
| 7,955,986 B2 | 6/2011 | Hoffman |
| 7,960,043 B2 | 6/2011 | Harris |
| 7,964,438 B2 | 6/2011 | Roca I Cabarrocas |
| 7,967,945 B2 | 6/2011 | Glukhoy |
| 7,975,646 B2 | 7/2011 | Rius |
| 7,985,188 B2 | 7/2011 | Felts |
| 8,025,915 B2 | 9/2011 | Haines |
| 8,038,858 B1 | 10/2011 | Bures |
| 8,039,524 B2 | 10/2011 | Chappa |
| 8,056,719 B2 | 11/2011 | Porret |
| 8,062,266 B2 | 11/2011 | McKinnon |
| 8,066,854 B2 | 11/2011 | Storey |
| 8,067,070 B2 | 11/2011 | Klein |
| 8,070,917 B2 | 12/2011 | Tsukamoto |
| 8,075,995 B2 | 12/2011 | Zhao |
| 8,092,605 B2 | 1/2012 | Shannon |
| 8,101,246 B2 | 1/2012 | Fayet |
| 8,197,452 B2 | 6/2012 | Harding |
| 8,227,025 B2 | 7/2012 | Lewis |
| 8,258,486 B2 | 9/2012 | Avnery |
| 8,268,410 B2 | 9/2012 | Moelle |
| 8,273,222 B2 | 9/2012 | Wei |
| 8,277,025 B2 | 10/2012 | Nakazawa |
| 8,313,455 B2 | 11/2012 | DiGregorio |
| 8,323,166 B2 | 12/2012 | Haines |
| 8,389,958 B2 | 3/2013 | Vo-Dinh |
| 8,397,667 B2 | 3/2013 | Behle |
| 8,409,441 B2 | 4/2013 | Wilt |
| 8,418,650 B2 | 4/2013 | Goto |
| 8,435,605 B2 | 5/2013 | Aitken et al. |
| 8,450,113 B2 | 5/2013 | Luepke |
| 8,475,886 B2 | 7/2013 | Chen et al. |
| 8,512,796 B2 | 8/2013 | Felts |
| 8,524,331 B2 | 9/2013 | Honda |
| 8,592,015 B2 | 11/2013 | Bicker |
| 8,603,638 B2 | 12/2013 | Liu |
| 8,618,509 B2 | 12/2013 | Vo-Dinh |

(56) References Cited

U.S. PATENT DOCUMENTS

| | | |
|---|---|---|
| 8,623,324 B2 | 1/2014 | Diwu |
| 8,633,034 B2 | 1/2014 | Trotter |
| 8,747,962 B2 | 6/2014 | Bicker |
| 8,802,603 B2 | 8/2014 | D'Souza |
| 8,816,022 B2 | 8/2014 | Zhao |
| 9,067,706 B2 | 6/2015 | Joergensen |
| 9,068,565 B2 | 6/2015 | Alarcon |
| 9,192,725 B2 | 11/2015 | Kawamura |
| 2001/0000279 A1 | 4/2001 | Daniels |
| 2001/0021356 A1 | 9/2001 | Konrad |
| 2001/0038894 A1 | 11/2001 | Komada |
| 2001/0042510 A1 | 11/2001 | Plester |
| 2001/0043997 A1 | 11/2001 | Uddin |
| 2002/0006487 A1 | 1/2002 | O'Connor |
| 2002/0007796 A1 | 1/2002 | Gorokhovsky |
| 2002/0070647 A1 | 6/2002 | Ginovker |
| 2002/0117114 A1 | 8/2002 | Ikenaga |
| 2002/0125900 A1 | 9/2002 | Savtchouk |
| 2002/0130100 A1 | 9/2002 | Smith |
| 2002/0130674 A1 | 9/2002 | Logowski |
| 2002/0141477 A1 | 10/2002 | Akahori |
| 2002/0153103 A1 | 10/2002 | Madocks |
| 2002/0155218 A1 | 10/2002 | Meyer |
| 2002/0170495 A1 | 11/2002 | Nakamura |
| 2002/0176947 A1 | 11/2002 | Darras |
| 2002/0182101 A1 | 12/2002 | Koulik |
| 2002/0185226 A1 | 12/2002 | Lea |
| 2002/0190207 A1 | 12/2002 | Levy |
| 2003/0010454 A1 | 1/2003 | Bailey, III |
| 2003/0013818 A1 | 1/2003 | Hakuta |
| 2003/0029837 A1 | 2/2003 | Trow |
| 2003/0031806 A1 | 2/2003 | Jinks |
| 2003/0046982 A1 | 3/2003 | Chartard |
| 2003/0058413 A1 | 3/2003 | Bamhurst |
| 2003/0102087 A1 | 6/2003 | Ito |
| 2003/0119193 A1 | 6/2003 | Hess |
| 2003/0148028 A1 | 8/2003 | Kimura et al. |
| 2003/0159654 A1 | 8/2003 | Arnold |
| 2003/0215652 A1 | 11/2003 | O'Connor |
| 2003/0219547 A1 | 11/2003 | Arnold |
| 2003/0232150 A1 | 12/2003 | Arnold |
| 2004/0024371 A1 | 2/2004 | Plicchi |
| 2004/0039401 A1 | 2/2004 | Chow |
| 2004/0040372 A1 | 3/2004 | Plester |
| 2004/0045811 A1 | 3/2004 | Wang |
| 2004/0050744 A1 | 3/2004 | Hama |
| 2004/0055538 A1 | 3/2004 | Gorokhovsky |
| 2004/0071960 A1 | 4/2004 | Weber |
| 2004/0082917 A1 | 4/2004 | Hetzler |
| 2004/0084151 A1 | 5/2004 | Kim |
| 2004/0125913 A1 | 7/2004 | Larson |
| 2004/0135081 A1 | 7/2004 | Larson |
| 2004/0149225 A1 | 8/2004 | Weikart |
| 2004/0175961 A1 | 9/2004 | Olsen |
| 2004/0177676 A1 | 9/2004 | Moore |
| 2004/0195960 A1 | 10/2004 | Czeremuszkin |
| 2004/0206309 A1 | 10/2004 | Bera |
| 2004/0217081 A1 | 11/2004 | Konrad |
| 2004/0247948 A1 | 12/2004 | Behle |
| 2004/0267194 A1 | 12/2004 | Sano |
| 2005/0000962 A1 | 1/2005 | Crawford |
| 2005/0010175 A1 | 1/2005 | Beedon |
| 2005/0019503 A1 | 1/2005 | Komada |
| 2005/0037165 A1 | 2/2005 | Ahem |
| 2005/0039854 A1 | 2/2005 | Matsuyama |
| 2005/0045472 A1 | 3/2005 | Nagata |
| 2005/0057754 A1 | 3/2005 | Smith |
| 2005/0073323 A1 | 4/2005 | Kohno |
| 2005/0075611 A1 | 4/2005 | Heltzer |
| 2005/0075612 A1 | 4/2005 | Lee |
| 2005/0161149 A1 | 7/2005 | Yokota |
| 2005/0169803 A1 | 8/2005 | Betz |
| 2005/0190450 A1 | 9/2005 | Becker |
| 2005/0196629 A1 | 9/2005 | Bariatinsky |
| 2005/0199571 A1 | 9/2005 | Geisler |
| 2005/0206907 A1 | 9/2005 | Fujimoto |
| 2005/0211383 A1 | 9/2005 | Miyata |
| 2005/0223988 A1 | 10/2005 | Behle |
| 2005/0227002 A1 | 10/2005 | Lizenberg |
| 2005/0227022 A1 | 10/2005 | Domine |
| 2005/0229850 A1 | 10/2005 | Behle |
| 2005/0233077 A1 | 10/2005 | Lizenberg |
| 2005/0233091 A1 | 10/2005 | Kumar |
| 2005/0236346 A1 | 10/2005 | Whitney |
| 2005/0260504 A1 | 11/2005 | Becker |
| 2005/0284550 A1 | 12/2005 | Bicker |
| 2006/0005608 A1 | 1/2006 | Kutzhoffer |
| 2006/0013997 A1 | 1/2006 | Kuepper |
| 2006/0014309 A1 | 1/2006 | Sachdev |
| 2006/0024849 A1 | 2/2006 | Zhu |
| 2006/0042755 A1 | 3/2006 | Holmberg |
| 2006/0046006 A1 | 3/2006 | Bastion |
| 2006/0051252 A1 | 3/2006 | Yuan |
| 2006/0051520 A1 | 3/2006 | Behle |
| 2006/0076231 A1 | 4/2006 | Wei |
| 2006/0086320 A1 | 4/2006 | Lizenberg |
| 2006/0099340 A1 | 5/2006 | Behle |
| 2006/0121222 A1 | 6/2006 | Audrich |
| 2006/0121613 A1 | 6/2006 | Havens |
| 2006/0121623 A1 | 6/2006 | He |
| 2006/0127699 A1 | 6/2006 | Moelle |
| 2006/0135945 A1 | 6/2006 | Bankiewicz |
| 2006/0138326 A1 | 6/2006 | Jiang |
| 2006/0150909 A1 | 7/2006 | Behle |
| 2006/0169026 A1 | 8/2006 | Kage |
| 2006/0178627 A1 | 8/2006 | Geiger |
| 2006/0183345 A1 | 8/2006 | Nguyen |
| 2006/0192973 A1 | 8/2006 | Aiyer |
| 2006/0196419 A1 | 9/2006 | Tudhope |
| 2006/0198903 A1 | 9/2006 | Storey |
| 2006/0198965 A1 | 9/2006 | Tudhope |
| 2006/0200078 A1 | 9/2006 | Konrad |
| 2006/0200084 A1 | 9/2006 | Ito |
| 2006/0210425 A1 | 9/2006 | Mirkarimi |
| 2006/0228497 A1 | 10/2006 | Kumar |
| 2006/0260360 A1 | 11/2006 | Dick |
| 2007/0003441 A1 | 1/2007 | Wohleb |
| 2007/0009673 A1 | 1/2007 | Fukazawa et al. |
| 2007/0017870 A1 | 1/2007 | Belov |
| 2007/0048456 A1 | 3/2007 | Keshner |
| 2007/0049048 A1 | 3/2007 | Rauf |
| 2007/0051629 A1 | 3/2007 | Donlik |
| 2007/0065680 A1 | 3/2007 | Schultheis |
| 2007/0076833 A1 | 4/2007 | Becker |
| 2007/0102344 A1 | 5/2007 | Konrad |
| 2007/0110907 A1 | 5/2007 | Brown |
| 2007/0123920 A1 | 5/2007 | Inokuti |
| 2007/0148326 A1 | 6/2007 | Hatings |
| 2007/0166187 A1 | 7/2007 | Song |
| 2007/0184657 A1 | 8/2007 | Iijima |
| 2007/0187229 A1 | 8/2007 | Aksenov |
| 2007/0187280 A1 | 8/2007 | Haines |
| 2007/0205096 A1 | 9/2007 | Nagashima |
| 2007/0215009 A1 | 9/2007 | Shimazu |
| 2007/0215046 A1 | 9/2007 | Lupke |
| 2007/0218265 A1 | 9/2007 | Harris |
| 2007/0224236 A1 | 9/2007 | Boden |
| 2007/0229844 A1 | 10/2007 | Holz |
| 2007/0231655 A1 | 10/2007 | Ha |
| 2007/0232066 A1 | 10/2007 | Bicker |
| 2007/0235890 A1 | 10/2007 | Lewis |
| 2007/0243618 A1 | 10/2007 | Hatchett |
| 2007/0251458 A1 | 11/2007 | Mund |
| 2007/0258894 A1 | 11/2007 | Melker et al. |
| 2007/0259184 A1 | 11/2007 | Martin |
| 2007/0281108 A1 | 12/2007 | Weikart |
| 2007/0281117 A1 | 12/2007 | Kaplan |
| 2007/0287950 A1 | 12/2007 | Kjeken |
| 2007/0287954 A1 | 12/2007 | Zhao |
| 2007/0298189 A1 | 12/2007 | Straemke |
| 2008/0011232 A1 | 1/2008 | Ruis |
| 2008/0017113 A1 | 1/2008 | Goto |
| 2008/0023414 A1 | 1/2008 | Konrad |
| 2008/0027400 A1 | 1/2008 | Harding |

(56) References Cited

U.S. PATENT DOCUMENTS

| | | |
|---|---|---|
| 2008/0033367 A1* | 2/2008 | Haury ............... A61M 5/3129 604/187 |
| 2008/0045880 A1 | 2/2008 | Kjeken |
| 2008/0050567 A1 | 2/2008 | Kawashima |
| 2008/0050932 A1 | 2/2008 | Lakshmanan |
| 2008/0053373 A1 | 3/2008 | Mund |
| 2008/0069970 A1 | 3/2008 | Wu |
| 2008/0071228 A1 | 3/2008 | Wu |
| 2008/0081184 A1 | 4/2008 | Kubo |
| 2008/0090039 A1* | 4/2008 | Klein ..................... C23C 16/30 428/35.7 |
| 2008/0093245 A1 | 4/2008 | Periasamy |
| 2008/0102206 A1 | 5/2008 | Wagner |
| 2008/0109017 A1 | 5/2008 | Herweck |
| 2008/0110852 A1 | 5/2008 | Kuroda |
| 2008/0113109 A1 | 5/2008 | Moelle |
| 2008/0118734 A1 | 5/2008 | Goodwin |
| 2008/0131628 A1 | 6/2008 | Abensour |
| 2008/0131638 A1 | 6/2008 | Hutton |
| 2008/0139003 A1 | 6/2008 | Pirzada |
| 2008/0144185 A1 | 6/2008 | Wang et al. |
| 2008/0145271 A1 | 6/2008 | Kidambi |
| 2008/0187681 A1 | 8/2008 | Hofrichter |
| 2008/0202414 A1 | 8/2008 | Yan |
| 2008/0206477 A1 | 8/2008 | Leontaris |
| 2008/0210550 A1 | 9/2008 | Walther |
| 2008/0220164 A1 | 9/2008 | Bauch |
| 2008/0223815 A1 | 9/2008 | Konrad |
| 2008/0233355 A1 | 9/2008 | Henze |
| 2008/0260966 A1 | 10/2008 | Hanawa |
| 2008/0277332 A1 | 11/2008 | Liu |
| 2008/0289957 A1 | 11/2008 | Takigawa |
| 2008/0292806 A1 | 11/2008 | Wei |
| 2008/0295772 A1 | 12/2008 | Park |
| 2008/0303131 A1 | 12/2008 | McElrea |
| 2008/0312607 A1 | 12/2008 | Delmotte |
| 2008/0314318 A1 | 12/2008 | Plan |
| 2009/0004091 A1 | 1/2009 | Kang |
| 2009/0004363 A1 | 1/2009 | Keshner |
| 2009/0017217 A1 | 1/2009 | Hass |
| 2009/0022981 A1 | 1/2009 | Yoshida |
| 2009/0029402 A1 | 1/2009 | Papkovsky |
| 2009/0031953 A1 | 2/2009 | Ingle |
| 2009/0032393 A1 | 2/2009 | Madocks |
| 2009/0039240 A1 | 2/2009 | Van Nijnatten |
| 2009/0053491 A1 | 2/2009 | Laboda |
| 2009/0061237 A1 | 3/2009 | Gates |
| 2009/0065485 A1 | 3/2009 | O'Neill |
| 2009/0069790 A1 | 3/2009 | Yokley |
| 2009/0081797 A1 | 3/2009 | Fadeev |
| 2009/0099512 A1 | 4/2009 | Digregorio |
| 2009/0104392 A1 | 4/2009 | Takada |
| 2009/0117268 A1 | 5/2009 | Lewis |
| 2009/0117389 A1 | 5/2009 | Amberg-Schwab |
| 2009/0122832 A1 | 5/2009 | Feist |
| 2009/0134884 A1 | 5/2009 | Bosselmann |
| 2009/0137966 A1 | 5/2009 | Rueckert |
| 2009/0142227 A1 | 6/2009 | Fuchs |
| 2009/0142514 A1 | 6/2009 | O'Neill |
| 2009/0147719 A1 | 6/2009 | Rak |
| 2009/0149816 A1 | 6/2009 | Hetzler |
| 2009/0155490 A1 | 6/2009 | Bicker |
| 2009/0162571 A1 | 6/2009 | Haines |
| 2009/0166312 A1 | 7/2009 | Giraud |
| 2009/0176031 A1 | 7/2009 | Armellin |
| 2009/0214801 A1 | 8/2009 | Higashi |
| 2009/0220948 A1 | 9/2009 | Oviso et al. |
| 2009/0263668 A1 | 10/2009 | David |
| 2009/0274851 A1 | 11/2009 | Goudar |
| 2009/0280268 A1 | 11/2009 | Glukhoy |
| 2009/0297730 A1 | 12/2009 | Glukhoy |
| 2009/0306595 A1 | 12/2009 | Shih |
| 2009/0326517 A1 | 12/2009 | Bork |
| 2010/0021998 A1 | 1/2010 | Sanyal |
| 2010/0028238 A1 | 2/2010 | Maschwitz |
| 2010/0034985 A1 | 2/2010 | Krueger |
| 2010/0075077 A1 | 3/2010 | Bicker et al. |
| 2010/0086808 A1 | 4/2010 | Nagata |
| 2010/0089097 A1 | 4/2010 | Brack |
| 2010/0104770 A1 | 4/2010 | Goudar |
| 2010/0105208 A1 | 4/2010 | Winniczek |
| 2010/0132762 A1 | 6/2010 | Graham, Jr. |
| 2010/0145284 A1 | 6/2010 | Togashi |
| 2010/0149540 A1 | 6/2010 | Boukherroub |
| 2010/0174239 A1 | 7/2010 | Yodfat |
| 2010/0174245 A1 | 7/2010 | Halverson |
| 2010/0178490 A1 | 7/2010 | Cerny |
| 2010/0186740 A1 | 7/2010 | Lewis |
| 2010/0190036 A1 | 7/2010 | Komvopoulos |
| 2010/0193461 A1 | 8/2010 | Boutroy |
| 2010/0195471 A1 | 8/2010 | Hirokane |
| 2010/0204648 A1 | 8/2010 | Stout |
| 2010/0230281 A1 | 9/2010 | Park |
| 2010/0231194 A1 | 9/2010 | Bauch |
| 2010/0237545 A1 | 9/2010 | Haury |
| 2010/0273261 A1 | 10/2010 | Chen |
| 2010/0275847 A1 | 11/2010 | Yamasaki |
| 2010/0279397 A1 | 11/2010 | Crawford |
| 2010/0298738 A1 | 11/2010 | Felts |
| 2010/0298779 A1 | 11/2010 | Hetzler |
| 2011/0037159 A1 | 2/2011 | McElrea |
| 2011/0046570 A1 | 2/2011 | Stout |
| 2011/0056912 A1 | 3/2011 | Magsuyama |
| 2011/0065798 A1 | 3/2011 | Hoang |
| 2011/0079582 A1 | 4/2011 | Yonesu |
| 2011/0093056 A1 | 4/2011 | Kaplan |
| 2011/0111132 A1 | 5/2011 | Wei |
| 2011/0117202 A1 | 5/2011 | Bourke, Jr. |
| 2011/0117288 A1 | 5/2011 | Honda |
| 2011/0137263 A1 | 6/2011 | Ashmead |
| 2011/0152820 A1* | 6/2011 | Chattaraj .......... A61M 5/14546 604/403 |
| 2011/0159101 A1 | 6/2011 | Kurdyumov et al. |
| 2011/0160662 A1 | 6/2011 | Stout |
| 2011/0160663 A1 | 6/2011 | Stout |
| 2011/0174220 A1 | 7/2011 | Laure |
| 2011/0186537 A1 | 8/2011 | Rodriguez San Juan et al. |
| 2011/0220490 A1 | 9/2011 | Wei |
| 2011/0253674 A1 | 10/2011 | Chung |
| 2011/0313363 A1 | 12/2011 | D'Souza et al. |
| 2011/0319758 A1 | 12/2011 | Wang |
| 2011/0319813 A1 | 12/2011 | Kamen |
| 2012/0003497 A1 | 1/2012 | Handy |
| 2012/0004339 A1 | 1/2012 | Chappa |
| 2012/0021136 A1 | 1/2012 | Dzengeleski |
| 2012/0031070 A1 | 2/2012 | Slough |
| 2012/0035543 A1 | 2/2012 | Kamen |
| 2012/0052123 A9 | 3/2012 | Kurdyumov et al. |
| 2012/0053530 A1 | 3/2012 | Zhao |
| 2012/0058351 A1 | 3/2012 | Zhao |
| 2012/0065612 A1 | 3/2012 | Stout |
| 2012/0097527 A1 | 4/2012 | Kodaira |
| 2012/0097870 A1 | 4/2012 | Leray |
| 2012/0108058 A1 | 5/2012 | Ha |
| 2012/0123345 A1 | 5/2012 | Felts |
| 2012/0141913 A1 | 6/2012 | Lee |
| 2012/0143148 A1 | 6/2012 | Zhao |
| 2012/0149871 A1 | 6/2012 | Saxena |
| 2012/0171386 A1 | 7/2012 | Bicker |
| 2012/0175384 A1 | 7/2012 | Greter |
| 2012/0183954 A1 | 7/2012 | Diwu |
| 2012/0205374 A1 | 8/2012 | Klumpen |
| 2012/0231182 A1 | 9/2012 | Stevens |
| 2012/0234720 A1 | 9/2012 | Digregorio |
| 2012/0252709 A1 | 10/2012 | Felts |
| 2013/0041241 A1 | 2/2013 | Felts |
| 2013/0046375 A1 | 2/2013 | Chen |
| 2013/0057677 A1 | 3/2013 | Weil |
| 2013/0072025 A1 | 3/2013 | Singh |
| 2013/0081953 A1 | 4/2013 | Bruna et al. |
| 2013/0190695 A1 | 7/2013 | Wu |
| 2013/0209704 A1 | 8/2013 | Krueger |
| 2013/0264303 A1 | 10/2013 | Andersen et al. |
| 2013/0296235 A1 | 11/2013 | Alarcon |

(56) References Cited

U.S. PATENT DOCUMENTS

| | | | |
|---|---|---|---|
| 2014/0010969 A1 | 1/2014 | Bicker |
| 2014/0052076 A1 | 2/2014 | Zhao |
| 2014/0054803 A1 | 2/2014 | Chen |
| 2014/0099455 A1 | 4/2014 | Stanley |
| 2014/0110297 A1 | 4/2014 | Trotter |
| 2014/0147654 A1 | 5/2014 | Walthe |
| 2014/0151320 A1 | 6/2014 | Chang |
| 2014/0151370 A1 | 6/2014 | Chang |
| 2014/0187666 A1 | 7/2014 | Aizenberg |
| 2014/0190846 A1 | 7/2014 | Belt |
| 2014/0221934 A1 | 8/2014 | Janvier |
| 2014/0251856 A1 | 9/2014 | Larsson |
| 2014/0251859 A1 | 9/2014 | Weikart et al. |
| 2014/0305830 A1 | 10/2014 | Bicker |
| 2015/0105734 A1 | 4/2015 | Bryant |
| 2015/0165125 A1 | 6/2015 | Foucher |
| 2015/0224263 A1 | 8/2015 | Dugand |
| 2016/0186009 A1 | 6/2016 | Goto |

FOREIGN PATENT DOCUMENTS

| | | |
|---|---|---|
| AU | 2002354470 B2 | 5/2007 |
| CA | 20858805 | 12/1992 |
| CA | 2277679 A1 | 7/1997 |
| CA | 2355681 | 7/2000 |
| CA | 2571380 A1 | 7/2006 |
| CA | 2718253 | 9/2009 |
| CA | 2268719 C | 8/2010 |
| CA | 2879732 A1 | 1/2014 |
| CN | 1245439 A | 2/2000 |
| CN | 2546041 Y | 4/2003 |
| CN | 1436104 A | 8/2003 |
| CN | 1639775 A | 7/2005 |
| CN | 1711310 A | 12/2005 |
| CN | 2766863 Y | 3/2006 |
| CN | 1898172 A | 1/2007 |
| CN | 101035630 A | 9/2007 |
| CN | 201002786 Y | 1/2008 |
| CN | 101147813 A | 3/2008 |
| CN | 201056331 Y | 5/2008 |
| CN | 102027159 A | 4/2011 |
| CN | 102036814 A | 4/2011 |
| CN | 102414343 A | 4/2012 |
| CN | 102581274 A | 7/2012 |
| CN | 102917805 A | 2/2013 |
| DE | 1147836 | 4/1969 |
| DE | 1147838 | 4/1969 |
| DE | 3632748 A1 | 4/1988 |
| DE | 3908418 A1 | 9/1990 |
| DE | 4214401 C1 | 3/1993 |
| DE | 4204082 A1 | 8/1993 |
| DE | 4316349 A1 | 11/1994 |
| DE | 4438359 | 5/1996 |
| DE | 19707645 A1 | 8/1998 |
| DE | 19830794 A1 | 1/2000 |
| DE | 19912737 A1 | 6/2000 |
| DE | 10010831 A1 | 9/2001 |
| DE | 10154404 C1 | 6/2003 |
| DE | 10201110 A1 | 10/2003 |
| DE | 10242698 | 3/2004 |
| DE | 10246181 A1 | 4/2004 |
| DE | 10353540 A1 | 5/2004 |
| DE | 102004017236 A1 | 10/2005 |
| DE | 102006061585 A1 | 2/2008 |
| DE | 102008023027 A1 | 11/2009 |
| EP | 0121340 A2 | 10/1984 |
| EP | 0221005 A2 | 5/1987 |
| EP | 0275965 A2 | 7/1988 |
| EP | 0284867 A2 | 10/1988 |
| EP | 0306307 | 3/1989 |
| EP | 0329041 A2 | 8/1989 |
| EP | 0343017 A2 | 11/1989 |
| EP | 0396919 A2 | 11/1990 |
| EP | 0482613 A1 | 10/1991 |
| EP | 0484746 A2 | 10/1991 |
| EP | 0495447 A1 | 7/1992 |
| EP | 0520519 A1 | 12/1992 |
| EP | 0535810 A1 | 4/1993 |
| EP | 0375778 B1 | 9/1993 |
| EP | 0571116 A1 | 11/1993 |
| EP | 0580094 A1 | 1/1994 |
| EP | 0603717 A2 | 6/1994 |
| EP | 0619178 | 10/1994 |
| EP | 0645470 A1 | 3/1995 |
| EP | 0697378 A2 | 2/1996 |
| EP | 0709485 B1 | 5/1996 |
| EP | 0719877 A1 | 7/1996 |
| EP | 0728676 A1 | 8/1996 |
| EP | 0787824 A2 | 8/1997 |
| EP | 0787828 A2 | 8/1997 |
| EP | 0814114 A1 | 12/1997 |
| EP | 0251812 A2 | 1/1998 |
| EP | 0833366 A2 | 4/1998 |
| EP | 0879611 A2 | 11/1998 |
| EP | 0940183 A2 | 9/1999 |
| EP | 0962229 A2 | 12/1999 |
| EP | 0992610 A2 | 4/2000 |
| EP | 1119034 A1 | 7/2001 |
| EP | 0954272 B1 | 3/2002 |
| EP | 1245694 A1 | 10/2002 |
| EP | 1388594 B1 | 1/2003 |
| EP | 1317937 A1 | 6/2003 |
| EP | 1365043 A1 | 11/2003 |
| EP | 1367145 | 12/2003 |
| EP | 1388593 A1 | 2/2004 |
| EP | 1439241 A2 | 7/2004 |
| EP | 1447459 A2 | 8/2004 |
| EP | 1990639 A1 | 2/2005 |
| EP | 1510595 A1 | 3/2005 |
| EP | 1522403 A2 | 4/2005 |
| EP | 1901067 A2 | 8/2005 |
| EP | 1507894 | 12/2005 |
| EP | 1507723 | 3/2006 |
| EP | 1653192 A1 | 5/2006 |
| EP | 1810758 A1 | 7/2007 |
| EP | 1356260 B1 | 12/2007 |
| EP | 1870117 A2 | 12/2007 |
| EP | 1881088 A1 | 1/2008 |
| EP | 1507887 | 7/2008 |
| EP | 1415018 | 10/2008 |
| EP | 1756565 A4 | 7/2009 |
| EP | 2199264 A1 | 11/2009 |
| EP | 1388594 B1 | 1/2010 |
| EP | 2178109 A1 | 4/2010 |
| EP | 1507895 | 7/2010 |
| EP | 2218465 A1 | 8/2010 |
| EP | 2243751 A1 | 10/2010 |
| EP | 2251671 | 11/2010 |
| EP | 2261185 | 12/2010 |
| EP | 2369038 A2 | 9/2011 |
| EP | 1960279 B1 | 10/2011 |
| EP | 2444771 A2 | 4/2012 |
| EP | 2602354 A1 | 6/2013 |
| EP | 2639330 A1 | 9/2013 |
| EP | 3381444 A1 | 10/2018 |
| FR | 891892 A | 11/1942 |
| GB | 752822 | 7/1956 |
| GB | 1363762 | 8/1974 |
| GB | 1513426 A | 6/1978 |
| GB | 1566251 | 4/1980 |
| GB | 2210826 A | 6/1989 |
| GB | 2231197 A | 11/1990 |
| GB | 2246794 A | 2/1992 |
| GB | 2246795 A | 2/1992 |
| GB | 2387964 A | 10/2003 |
| IT | 1304783 B1 | 3/2001 |
| IT | 1310330 B1 | 2/2002 |
| JP | 56027330 A | 3/1981 |
| JP | 58154602 A | 9/1983 |
| JP | 59087307 A | 5/1984 |
| JP | 59154029 | 9/1984 |
| JP | S61183462 A | 8/1986 |
| JP | S62180069 A | 8/1987 |
| JP | S62290866 A | 12/1987 |

(56) References Cited

FOREIGN PATENT DOCUMENTS

| | | |
|---|---|---|
| JP | 63124521 A2 | 5/1988 |
| JP | 1023105 A | 1/1989 |
| JP | H01225775 A | 9/1989 |
| JP | 1279745 | 11/1989 |
| JP | 2501490 | 5/1990 |
| JP | 3183759 A2 | 8/1991 |
| JP | H03260065 A | 11/1991 |
| JP | H03271374 A | 12/1991 |
| JP | 4000373 A | 1/1992 |
| JP | 4000374 A | 1/1992 |
| JP | 4000375 A | 1/1992 |
| JP | 4014440 A | 1/1992 |
| JP | H04124273 A | 4/1992 |
| JP | H0578844 A | 3/1993 |
| JP | 05-006688 A | 4/1993 |
| JP | H05263223 A | 10/1993 |
| JP | 6010132 A | 1/1994 |
| JP | 6289401 | 10/1994 |
| JP | 7041579 A | 2/1995 |
| JP | 7068614 A | 3/1995 |
| JP | 7126419 A | 5/1995 |
| JP | 7-304127 | 11/1995 |
| JP | 8025244 A | 1/1996 |
| JP | 8084773 A | 4/1996 |
| JP | H08296038 A | 11/1996 |
| JP | 9005038 A | 1/1997 |
| JP | 10008254 A | 1/1998 |
| JP | 10-130844 | 5/1998 |
| JP | 11-108833 A | 4/1999 |
| JP | 11106920 | 4/1999 |
| JP | H11256331 A | 9/1999 |
| JP | 11344316 A | 12/1999 |
| JP | 2000064040 A | 2/2000 |
| JP | 2000109076 A | 4/2000 |
| JP | 2001033398 A | 2/2001 |
| JP | 2001231841 A | 8/2001 |
| JP | 2002177364 A | 6/2002 |
| JP | 2002206167 A | 7/2002 |
| JP | 2002371364 A | 12/2002 |
| JP | 2003171771 A | 6/2003 |
| JP | 2003-268550 A | 9/2003 |
| JP | 2003294431 A | 10/2003 |
| JP | 2003305121 A | 10/2003 |
| JP | 2004002928 A | 1/2004 |
| JP | 2004008509 A | 1/2004 |
| JP | 2004043789 A | 2/2004 |
| JP | 2004100036 A | 4/2004 |
| JP | 2004156444 A | 6/2004 |
| JP | 2004168359 A | 6/2004 |
| JP | 2004169087 A | 6/2004 |
| JP | 2004203682 A | 7/2004 |
| JP | 2004-253683 A | 9/2004 |
| JP | 2004307935 A | 11/2004 |
| JP | 2005035597 A | 2/2005 |
| JP | 2005043285 A | 2/2005 |
| JP | 2005132416 A | 5/2005 |
| JP | 2005160888 A | 6/2005 |
| JP | 2005-200044 | 7/2005 |
| JP | 2005200044 A | 7/2005 |
| JP | 2005-241524 A | 9/2005 |
| JP | 2005271997 A | 10/2005 |
| JP | 2005290561 A | 10/2005 |
| JP | 2006-064416 A | 3/2006 |
| JP | 2006111967 A | 4/2006 |
| JP | 2006160268 A | 6/2006 |
| JP | 2006-224992 A | 8/2006 |
| JP | 2006249577 A | 9/2006 |
| JP | 2007050898 A | 3/2007 |
| JP | 2007231386 A | 9/2007 |
| JP | 2007246974 A | 9/2007 |
| JP | 2008174793 A | 7/2008 |
| JP | 2009-062620 A | 3/2009 |
| JP | 2009062620 A | 3/2009 |
| JP | 2009079298 A | 4/2009 |
| JP | 2009084203 A | 4/2009 |
| JP | 2009185330 A | 8/2009 |
| JP | 2010155134 A | 7/2010 |
| JP | 2010270117 A | 12/2010 |
| JP | 2012149278 A | 8/2012 |
| JP | 2012210315 A | 11/2012 |
| JP | 2012526921 A | 11/2012 |
| JP | 2013233716 A | 11/2013 |
| JP | 5362941 B2 | 12/2013 |
| KR | 10-2005-0100367 A | 10/2005 |
| KR | 10-2006-0029694 | 4/2006 |
| KR | 10-0685594 B1 | 2/2007 |
| SU | 1530913 | 12/1989 |
| TW | 200703536 A | 1/2007 |
| WO | WO9324243 A1 | 12/1993 |
| WO | WO9400247 A1 | 1/1994 |
| WO | WO9426497 A1 | 11/1994 |
| WO | WO95/24275 | 9/1995 |
| WO | WO97/11482 | 3/1997 |
| WO | WO97/13802 | 4/1997 |
| WO | WO98-27926 | 7/1998 |
| WO | WO98/45871 | 10/1998 |
| WO | WO9917334 A1 | 4/1999 |
| WO | WO99/41425 | 8/1999 |
| WO | WO9945984 A1 | 9/1999 |
| WO | WO9945985 A1 | 9/1999 |
| WO | WO9947192 A1 | 9/1999 |
| WO | WO99/50471 | 10/1999 |
| WO | WO0038566 A2 | 7/2000 |
| WO | WO0104668 A1 | 1/2001 |
| WO | WO0125788 | 4/2001 |
| WO | WO0154816 A1 | 8/2001 |
| WO | WO0156706 A1 | 8/2001 |
| WO | WO0170403 A1 | 9/2001 |
| WO | WO0222192 A1 | 3/2002 |
| WO | WO03033426 | 4/2002 |
| WO | WO02/43116 A2 | 5/2002 |
| WO | WO0249925 A1 | 6/2002 |
| WO | WO02/056333 A1 | 7/2002 |
| WO | WO02072914 | 9/2002 |
| WO | WO02076709 A1 | 10/2002 |
| WO | 02100928 A1 | 12/2002 |
| WO | WO03014415 A1 | 2/2003 |
| WO | WO03038143 | 5/2003 |
| WO | WO03040649 A1 | 5/2003 |
| WO | WO03044240 A1 | 5/2003 |
| WO | 2004044039 A2 | 5/2004 |
| WO | WO2005035147 A1 | 4/2005 |
| WO | WO2005/052555 A | 6/2005 |
| WO | WO2005051525 A1 | 6/2005 |
| WO | WO2005094214 A2 | 10/2005 |
| WO | WO2005103605 A1 | 11/2005 |
| WO | WO2006012281 A1 | 2/2006 |
| WO | WO2006017186 A1 | 2/2006 |
| WO | WO2006027568 A1 | 3/2006 |
| WO | WO2006029743 A1 | 3/2006 |
| WO | WO2006044254 A1 | 4/2006 |
| WO | WO2006/048650 | 5/2006 |
| WO | WO2006048276 | 5/2006 |
| WO | WO2006048277 A1 | 5/2006 |
| WO | WO2006069774 A1 | 7/2006 |
| WO | 2006121556 A3 | 11/2006 |
| WO | WO2006135755 A2 | 12/2006 |
| WO | WO2007028061 A2 | 3/2007 |
| WO | WO2007035741 A2 | 3/2007 |
| WO | WO2007036544 A1 | 4/2007 |
| WO | WO2007/081814 | 7/2007 |
| WO | WO2007/089216 A1 | 8/2007 |
| WO | WO2007112328 A2 | 10/2007 |
| WO | WO2007120507 A2 | 10/2007 |
| WO | WO2007133378 A1 | 11/2007 |
| WO | WO2007134347 A2 | 11/2007 |
| WO | WO2008014438 A1 | 1/2008 |
| WO | WO2008024566 A2 | 2/2008 |
| WO | WO2008040531 A1 | 4/2008 |
| WO | WO2008047541 A1 | 4/2008 |
| WO | WO2008067574 A1 | 6/2008 |
| WO | WO2008071458 A1 | 6/2008 |
| WO | WO2008093335 A2 | 8/2008 |
| WO | 2008/121478 A2 | 10/2008 |

(56) References Cited

FOREIGN PATENT DOCUMENTS

| | | |
|---|---|---|
| WO | WO2009/015862 A1 | 2/2009 |
| WO | WO2009020550 A2 | 2/2009 |
| WO | WO2009021257 A1 | 2/2009 |
| WO | WO2009030974 | 3/2009 |
| WO | WO2009030975 A1 | 3/2009 |
| WO | WO2009030976 A1 | 3/2009 |
| WO | WO2009031838 A1 | 3/2009 |
| WO | WO2009040109 | 4/2009 |
| WO | WO2009053947 A2 | 4/2009 |
| WO | WO2009112053 A1 | 9/2009 |
| WO | WO2009117032 | 9/2009 |
| WO | WO2009118361 A1 | 10/2009 |
| WO | WO2009158613 | 12/2009 |
| WO | WO2010047825 A1 | 4/2010 |
| WO | WO2010095011 A1 | 8/2010 |
| WO | WO2010/132579 | 11/2010 |
| WO | WO2010/132581 | 11/2010 |
| WO | WO2010/132584 | 11/2010 |
| WO | WO2010/132585 | 11/2010 |
| WO | WO2010/132589 | 11/2010 |
| WO | WO2010/132591 | 11/2010 |
| WO | WO2010034004 A1 | 11/2010 |
| WO | WO2010132579 | 11/2010 |
| WO | WO2010132579 A2 | 11/2010 |
| WO | WO2010132589 | 11/2010 |
| WO | WO2010132591 | 11/2010 |
| WO | WO2011029628 | 3/2011 |
| WO | WO2011059823 A1 | 5/2011 |
| WO | WO2011007055 A1 | 6/2011 |
| WO | WO2011080543 A1 | 7/2011 |
| WO | WO2011082296 A1 | 7/2011 |
| WO | WO2011090717 A1 | 7/2011 |
| WO | WO2011/143329 | 11/2011 |
| WO | WO2011/143509 | 11/2011 |
| WO | WO2011/143509 A1 | 11/2011 |
| WO | WO2011137437 | 11/2011 |
| WO | WO2011143329 | 11/2011 |
| WO | WO2011159975 A1 | 12/2011 |
| WO | WO2012003221 | 1/2012 |
| WO | WO2012009653 | 1/2012 |
| WO | WO2012166515 A1 | 12/2012 |
| WO | WO2013045671 A1 | 4/2013 |
| WO | WO2013/071138 | 5/2013 |
| WO | WO2013/071138 A1 | 5/2013 |
| WO | WO2013106588 A1 | 7/2013 |
| WO | WO2013/170044 | 11/2013 |
| WO | WO2013/170052 | 11/2013 |
| WO | 2014-005728 A1 | 1/2014 |
| WO | WO2014008138 | 1/2014 |
| WO | WO2014012039 A1 | 1/2014 |
| WO | WO2014012052 A1 | 1/2014 |
| WO | WO2014012072 A2 | 1/2014 |
| WO | WO2014012078 A2 | 1/2014 |
| WO | WO2014012079 A1 | 1/2014 |
| WO | WO2014014641 A1 | 1/2014 |
| WO | WO2014/059012 | 4/2014 |
| WO | WO2014/071061 | 5/2014 |
| WO | WO2014/078666 | 5/2014 |
| WO | WO2014/085346 | 6/2014 |
| WO | WO2014/085348 | 6/2014 |
| WO | WO2014/134577 | 9/2014 |
| WO | WO2014/144926 | 9/2014 |
| WO | WO2014/164928 | 10/2014 |
| WO | WO2015049972 A1 | 4/2015 |
| WO | WO2016057068 A1 | 4/2016 |
| WO | WO2016094387 A2 | 6/2016 |

OTHER PUBLICATIONS

Hanlon, Adriene Lepiane, Pak, Chung K., Pawlikowski, Beverly A., Decision on Appeal, Appeal No. 2005-1693, U.S. Appl. No. 10/192,333, dated Sep. 30, 2005.

Arganguren, Mirta I., Macosko, Christopher W., Thakkar, Bimal, and Tirrel, Matthew, "Interfacial Interactions in Silica Reinforced Silicones," Materials Research Society Symposium Proceedings, vol. 170, 1990, pp. 303-308.

Patent Cooperation Treaty, International Preliminary Examining Authority, Notification of Transmittal of International Preliminary Report on Patentability, in international application No. PCT/US2011/036097, dated Nov. 13, 2012.

Patent Cooperation Treaty, Written Opinion of the International Searching Authority with International Search Report in Application No. PCT/US2012/064489, dated Jan. 25, 2013.

Danish Patent and Trademark Office, Singapore Written Opinion, in Application No. 201108308-6, dated Dec. 6, 2012.

Danish Patent and Trademark Office, Singapore Search Report, in Application No. 201108308-6, dated Dec. 12, 2012.

Tao, Ran et al., Condensationand Polymerization of Supersaturated Monomer Vapor, ACS Publications, 2012 American Chemical Society, ex.doi.org/10.1021/la303462q/Langmuir 2012, 28, 16580-16587.

State Intellectual Property Office of Teh People's Republic of China, Notification of First Office Action in Application No. 201080029201.4, dated Mar. 37, 2013. (15 pages).

PCT, Notification of Transmittal of the International Search Report and the Written Opinion of the International Searching Authority, or the Declaration, in International application No. PCT/US2013/040380, dated Sep. 3, 2013. (13 pages).

PCT, Notification of Transmittal of the International Search Report and the Written Opinion of the International Searching Authority, or the Declaration, in International application No. PCT/US2013/040368, dated Oct. 21, 2013. (21 pages).

PCT, Notification of Transmittal of the International Search Report and the Written Opinion of the International Searching Authority, or the Declaration, in International application No. PCT/US2013/048709, dated Oct. 2, 2013. (7 pages).

Coclite A.M. et al., "On the relationship between the structure and the barrier performance of plasma deposited silicon dioxide-like films", Surface and Coatings Technology, Elsevier, Amsterdam, NL, vol. 204, No. 24, Sep. 15, 2010 (Sep. 15, 2010), pp. 4012-4017, XPO27113381, ISSN: 0257-8972 [retrieved on Jun. 16, 2010] abstract, p. 4014, right-hand column—p. 4015, figures 2, 3.

Brunet-Bruneau A. et al., "Microstructural characterization of ion assisted Sio2 thin films by visible and infrared ellipsometry", Journal of Vacuum Science and Technology: Part A, AVS/AIP, Melville, NY, US, vol. 16, No. 4, Jul. 1, 1998 (Jul. 1, 1998), pp. 2281-2286, XPO12004127, ISSN: 0734-2101, DOI: 10.1116/1.581341, p. 2283, right-hand column—p. 2284, left-hand column, figures 2, 4.

P.G. Pai, S.S. Chao, and Y Takagi, "Infrared Spectroscopic Study of SiOx Films Produced by Plasma Enhanced Chemical Vapor Deposition",Journal of Vacuum Science & Technology A: Vacuum Surfaces and Films, Jun. 1986, p. 689-694; retrieved on Jun. 1, 2014 (7 pages).

C. Weikart and T. Smith, The Dow Chemical Company, "Microwave Plasma Barrier Coating Technology or PET Beverages Containers", Society of Vacuum Coaters, 46th Annual Technical Conference Proceedings, ISSN 0737-5921, pp. 486-490, 2003 (5 pages).

C. Weikart, T. Fisk, and M. Larive, The Dow Chemical Company; T. Glass, H. Pham, and A. Taha, The Dow Chemical Company, J. Felts, Nano Scale Surface Systems, Inc.; "Advances in PECVD Barrier Coating Development for ISBM PP Containers", Society of Vacuum Coaters, 51st Annual Technical Conference Proceedings, ISSN 0737-5921, pp. 569-573, Apr. 19-24, 2008 (5 pages).

C. Weikart, H. Yasuda, "Modification, Degradation, and Stability of Polymeric Surfaces Treated with Reactive Plasmas", Journal of Polymer Science: Part A: Polymer Chemistry, vol. 38, 3028-3042, John Wiley & Sons, Inc., 2000 (15 pages).

Sahagian, Khoren; Larner, Mikki; Kaplan, Stephen L., "Altering Biological Interfaces with Gas Plasma: Example Applications", Plasma Technology Systems, Belmont, CA, In SurFACTS in Biomaterials, Surfaces in Biomaterials Foundation, Summer 2013, 18(3), p. 1-5.

(56) References Cited

OTHER PUBLICATIONS

Daikyo Cyrystal Zenith Insert Needle Syringe System, West Delivering Innovative Services, West Pharmaceutical Services, Inc., 2010.
Daikyo Crystal Zenigh Syringes, West Pharmaceutical Services, Inc., www.WestPFSsolutions.com, #5659, 2011.
Zhang, Yongchao and Heller, Adam, Reduction of the Nonspecific Binding of a Target Antibody and of Its Enzyme-Labeled Detection Probe Enabling Electrochemical Immunoassay of Antibody through the 7 pg/mL-100 ng/mL (40 fM-400 pM) Range, Department of Chemical Engieering and Texas Materials Institute, University of Texas at Austin, Anal. Chem. 2005, 7, 7758-7762. (6 pages).
Principles and Applications of Liquid Scintillation Counting, LSC Concepts—Fundamentals of Liquid Scintillation Counting, National Diagnostics, 2004, pp. 1-15.
Chikkaveeraiah, Bhaskara V. and Rusling, Dr. James, Non Specific Binding (NSB) in Antigen-Antibody Assays, University of Connecticut, Spring 2007. (13 pages).
Sahagian, Khoren; Larner, Mikki; Kaplan, Stephen L., "Cold Gas Plasma in Surface Modification of Medical Plastics", Plasma Technology Systems, Belmont, CA, Publication pending. Presented at SPE Antec Medical Plastics Division, Apr. 23, 2013, Ohio.
Lipman, Melissa, "Jury Orders Becton to Pay $114M In Syringe Antitrust Case", © 2003-2013, Portfolio Media, Inc., Law360, New York (Sep. 20, 2013, 2:53 PM ET), http://www.law360.com/articles/474334/print?section=ip, [retrieved Sep. 23, 2013].
Wikipedia, the free encyclopedia, http://en.wikipedia.org/wiki/Birefringence, page last modified Sep. 18, 2013 at 11:39. [retrieved on Oct. 8, 2013]. (5 pages).
Wikipedia, the free encyclopedia, http://en.wikipedia.org/wiki/Confocal_microscopy, page last modified Aug. 28, 2013 at 11:12. [retrieved on Oct. 8, 2013]. (4 pages).
Wang, Jun et al., "Fluorocarbon thin film with superhydrophobic property prepared by pyrolysis of hexafluoropropylene oxide", Applied Surface Science, vol. 258, 2012, pp. 9782-9784 (4 pages).
Wang, Hong et al., "Ozone-Initiated Secondary Emission Rates of Aldehydes from Indoor surfaces in Four Homes", American Chemical Society, Environmental Science & Technology, vol. 40, No. 17, 2006, pp. 5263-5268 (6 pages).
Lewis, Hilton G. Pryce, et al., "HWCVD of Polymers: Commercialization and Scale-Up", Thin Solid Films 517, 2009, pp. 3551-3554.
Wolgemuth, Lonny, "Challenges With Prefilled Syringes: The Parylene Solution", Frederick Furness Publishing, www.ongrugdelivery.com, 2012, pp. 44-45.
History of Parylene (12 pages).
SCS Parylene HTX brochure, Stratamet Thin Film Corporation, Fremont, CA, 2012, retrieved from the Internet Feb. 13, 2013, http://www.stratametthinfilm.com/parylenes/htx. (2 pages).
SCS Parylene Properties, Specialty Coating Systems, Inc., Indianapolis, IN, 2011. (12 pages).
Werthheimer, M.R., Studies of the earliest stages of plasma-enhanced chemical vapor deposition of SiO2 on polymeric substrates, Thin Solid Films 382 (2001) 1-3, and references therein, United States Pharmacopeia 34. In General Chapters <1>, 2001.
Gibbins, Bruce and Warner, Lenna, The Role of Antimicrobial Silver Nanotechnology, Medical Device & Diagnostic Industry, Aug. 205, pp. 2-6.
MTI CVD Tube Furnace w Gas Delivery & Vacuum Pump, http://mtixtl.com/MiniCVDTubeFurnace2ChannelsGasVacuum-OTF-1200X-S50-2F.aspx (2 pages).
Lab-Built HFPO CVD Coater, HFPO Decomp to Give Thin Fluorocarbon Films, Applied Surface Science 2012 258 (24) 9782.
Technical Report No. 10, Journal of Parenteral Science and Technology, 42, Supplement 1988, Parenteral Formulation of Proteins and Peptides: Stability and Stabilizers, Parenteral Drug Association, 1988.
Technical Report No. 12, Journal of Parenteral Science and Technology, 42, Supplement 1988, Siliconization of Parenteral Drug Packaging Components, Parenteral Drug Association, 1988.
European Patent Office, Communication under Rule 71(3) EPC, in Application No. 10 162 760.2-1353, dated Oct. 25, 2013. (366 pages).
Wikipedia, the free encyclopedia, http://en.wikipedia.org/wiki/Difluorocarbene, page last modified Feb. 20, 2012 at 14:41. [retrieved on Sep. 7, 2012]. (4 pages).
O'Shaughnessy, W.S., et al., "Initiated Chemical Vapor Deposition of a Siloxane Coating for Insulation of Neutral Probes", Thin Solid Films 517 (2008) 3612-3614. (3 pages).
Denler, et al., Investigations of SiOx-polymer "interphases" by glancing angle RBS with Li+ and Be+ ions, Nuclear Instruments and Methods in Physical Research B 208 (2003) 176-180, United States Pharmacopeia 34. In General Chapters <1>, 2003.
PCT, Invitation to Pay Additional Fees and Annex to Form PCT/ISA/206 Communication relating to the results of the partial international search in International application No. PCT/US2013/071750, dated Feb. 14, 2014. (6 pages).
PCT, Notification of Transmittal of the International Search Report and the Written Opinion of the International Searching Authority, or the Declaration, in International application No. PCT/US2013/62247, dated Dec. 30, 2013. (13 pages).
PCT, Notification of Transmittal of the International Search Report and the Written Opinion of the International Searching Authority, or the Declaration, in International application No. PCT/US2013/043642, dated Dec. 5, 2013. (21 pages).
Japanese Patent Office, Notice of Reason(s) for Rejection in Patent application No. 2012-510983, dated Jan. 7, 2014. (6 pages).
Chinese Patent Office, Notification of the Second Office Action in Application No. 201080029199.0, dated Jan. 6, 2014. (26 pages).
Chinese Patent Office, Notification of the First Office Action in Application No. 201180023474.2, dated Dec. 23, 2013. (18 pages).
PCT, Notification of Transmittal of the International Search Report and the Written Opinion of the International Searching Authority, or the Declaration, in International application No. PCT/US2013/067852, dated Jan. 22, 2014. (9 pages).
PCT, Notification of Transmittal of the International Search Report and the Written Opinion of the International Searching Authority, or the Declaration, in International application No. PCT/US2013/064121, dated Mar. 24, 2014. (8 pages).
PCT, Notification of Transmittal of the International Search Report and the Written Opinion of the International Searching Authority, or the Declaration, in International application No. PCT/US2013/070325, dated Mar. 24, 2014. (16 pages).
Patent Cooperation Treaty, Notification of Transmittal of International Preliminary Report on Patentability, in Application No. PCT/US2010/034576, dated Sep. 14, 2011.
Patent Cooperation Treaty, Notification of Transmittal of International Preliminary Report on Patentability, in Application No. PCT/US2010/034568, dated Sep. 14, 2011.
Patent Cooperation Treaty, International Search Report and Written Opinion, in Application No. PCT/US2011/036358, dated Sep. 9, 2011.
Patent Cooperation Treaty, International Search Report and Written Opinion, in Application No. PCT/US2011/036340, dated Aug. 1, 2011.
MacDonald, Gareth, "West and Daikyo Seiko Launch Ready Pack", http://www.in-pharmatechnologist.com/Packaging/West-and-Daikyo-Seiko-launch-Ready-Pack, 2 pages, retrieved from the internet Sep. 22, 2011.
Kumer, Vijai, "Development of Terminal Sterilization Cycle for Pre-Filled Cyclic Olefin Polymer (COP) Syringes", http://abstracts.aapspharmaceutica.com/ExpoAAPS09/CC/forms/attendee/index.aspx?content=sessionInfo&sessionId=401, 1 page, retrieved from the internet Sep. 22, 2011.
Quinn, F.J., "Biotech Lights Up the Glass Packaging Picture", http://www.pharmaceuticalcommerce.com/frontEnd/main.php?idSeccion=840, 4 pages, retrieved from the Internet Sep. 21, 2011.
Wen, Zai-Qing et al., Distribution of Silicone Oil in Prefilled Glass Syringes Probed with Optical and Spectroscopic Methods, PDA Journal of Pharmaceutical Science and Technology 2009, 63, pp. 149-158.
ZebraSci—Intelligent Inspection Products, webpage, http://zebrasci.com/index.html, retrieved from the internet Sep. 30, 2011.

(56) References Cited

OTHER PUBLICATIONS

Google search re "cyclic olefin polymer resin" syringe or vial, http://www.google.com/search?sclient=psy-ab&hl=en&lr=&source=hp&q=%22cyclic+olefin+polymer+resin%22+syringe+OR+vial&btnG=Search&pbx=1&oq=%22cyclic+olefin+polymer+resin%22+syringe+OR+vial&aq, 1 page, retrieved from the internet Sep. 22, 2011.

Taylor, Nick, "West to Add CZ Vials as Glass QC Issues Drive Interest", ttp://twitter.com/WestPharma/status/98804071674281986, 2 pages, retrieved from the internet Sep. 22, 2011.

Patent Cooperation Treaty, International Preliminary Examining Authority, Notification of Transmittal of International Preliminary Report on Patentability, in international application No. PCT/US2010/034571, dated Jun. 13, 2011.

Patent Cooperation Treaty, International Preliminary Examining Authority, Written Opinion of the International Preliminary Examining Authority, in international application No. PCT/US2010/034586, dated Aug. 23, 2011.

Patent Cooperation Treaty, International Preliminary Examining Authority, Written Opinion of the International Preliminary Examining Authority, in international application No. PCT/US2010/034568, dated May 30, 2011.

Silicone Oil Layer, Contract Testing, webpage, http://www.siliconization.com/downloads/siliconeoillayercontracttesting.pdf, retrieved from the internet Oct. 28, 2011.

Patent Cooperation Treaty, Notification of Transmittal of International Preliminary Report on Patentability, in PCT/US2010/034577, dated Nov. 24, 2011.

Patent Cooperation Treaty, Notification of Transmittal of International Preliminary Report on Patentability, in PCT/US2010/034582, dated Nov. 24, 2011.

Patent Cooperation Treaty, Notification of Transmittal of International Preliminary Report on Patentability, in PCT/US2010/034586, dated Dec. 20, 2011.

Patent Cooperation Treaty, Notification of Transmittal of the International Search Report and the Written Opinion of the International Searching Authority, in PCT/US2011/036097, dated Dec. 29, 2011.

"Oxford instruments plasmalab 80plus", XP55015205, retrieved from the Internet on Dec. 20, 2011, URL:http://www.oxfordplasma.de/pdf_inst/plas_80.pdf.

Patent Cooperation Treaty, Notification of Transmittal of the International Search Report and the Written Opinion of the International Searching Authority, in PCT/US2011/044215, dated Dec. 29, 2011.

European Patent Office, Communication pursuant to Article 94(3) EPC, in Application No. 10 162 758.6-1234, dated May 8, 2012 (6 pages).

Allison, H.L., The Real Markets for Transparent Barrier Films, 37th Annual Technical Conference Proceedings, 1994, ISBN 1-878068-13-X, pp. 458.

Bailey, R. et al., Thin-Film Multilayer Capacitors Using Pyrolytically Deposited Silicon Dioxide, IEEE Transactions on Parts, Hybrids, and Packaging, vol. PHP-12, No. 4, Dec. 1976, pp. 361-364.

Banks, B.A., et al., Fluoropolymer Filled SiO2 Coatings; Properties and Potential Applications, Society of Vacuum Coaters, 35th Annual Technical Conference Proceedings, 1992, ISBN 1-878068-11-3, pp. 89-93.

Baouchi, W., X-Ray Photoelectron Spectroscopy Study of Sodium Ion Migration through Thin Films of SiO2 Deposited on Sodalime Glass, 37th Annual Technical Conference Proceedings, 1994, ISBN 1-878068-13-X, pp. 419-422.

Boebel, F. et al., Simultaneous In Situ Measurement of Film Thickness and Temperature by Using Multiple Wavelengths Pyrometric Interferometry (MWPI), IEEE Transaction on Semiconductor Manufacturing, vol. 6, No. 2, May 1993, ,pp. 112-118.

Bush, V. et al., The Evolution of Evacuated Blood Collection Tubes, BD Diagnostics—Preanalytical Systems Newsletter, vol. 19, No. 1, 2009.

Chahroudi, D., Deposition Technology for Glass Barriers, 33rd Annual Technical Conference Proceedings, 1990, ISBN 1-878068-09-1, pp. 212-220.

Chahroudi, D., et al., Transparent Glass Barrier Coatings for Flexible Film Packaging, Society of Vacuum Coaters, 34th Annual Technical Conference Proceedings, 1991, ISBN 1-878068-10-5, pp. 130-133.

Chahroudi, D., Glassy Barriers from Electron Beam Web Coaters, 32nd Annual Technical Conference Proceedings, 1989, pp. 29-39.

Czeremuszkin, G. et al., Ultrathin Silicon-Compound Barrier Coatings for Polymeric Packaging Materials: An Industrial Perspective, Plasmas and Polymers, vol. 6, Nos. 1/2, Jun. 2001, pp. 107-120.

Ebihara, K. et al., Application of the Dielectric Barrier Discharge to Detect Defects in a Teflon Coated Metal Surface, 2003 J. Phys. D: Appl. Phys. 36 2883-2886, doi: 10.1088/0022-3727/36/23/003, IOP Electronic Journals, http://www.iop.org/EJ/abstract/0022-3727/36/23/003, printed Jul. 14, 2009.

Egitto, F.D., et al., Plasma Modification of Polymer Surfaces, Society of Vacuum Coaters, 36th Annual Technical Conference Proceedings, 1993, ISBN 1-878068-12-1, pp. 10-21.

Erlat, A.G. et al., SIOx Gas Barrier Coatings on Polymer Substrates: Morphology and Gas Transport Considerations, ACS Publications, Journal of Physical Chemistry, published Jul. 2, 1999, http://pubs.acs.org/doi/abs/10.1021/jp990737e, printed Jul. 14, 2009.

Fayet, P., et al., Commercialism of Plasma Deposited Barrier Coatings for Liquid Food Packaging, 37th Annual Technical Conference Proceedings, 1995, ISBN 1-878068-13-X, pp. 15-16.

Felts, J., Hollow Cathode Based Multi-Component Depositions, Vacuum Technology & Coating, Mar. 2004, pp. 48-55.

Felts, J.T., Thickness Effects on Thin Film Gas Barriers: Silicon-Based Coatings, Society of Vacuum Coaters, 34th Annual Technical Conference Proceedings, 1991, ISBN 1-878068-10-5, pp. 99-104.

Felts, J.T., Transparent Barrier Coatings Update: Flexible Substrates, Society of Vacuum Coaters, 36th Annual Technical Conference Proceedings, 1993, ISBN 1-878068-12-1, pp. 324-331.

Felts, J.T., Transparent Gas Barrier Technologies, 33rd Annual Technical Conference Proceedings, 1990, ISBN 1-878068-09-1, pp. 184-193.

Finson, E., et al., Transparent SiO2 Barrier Coatings: Conversion and Production Status, 37th Annual Technical Conference Proceedings, 1994, ISBN 1-878068-13-X, pp. 139-143.

Flaherty, T. et al., Application of Spectral Reflectivity to the Measurement of Thin-Film Thickness, Opto-Ireland 2002: Optics and Photonics Technologies and Applications, Proceedings of SPIE vol. 4876, 2003, pp. 976-983.

Hora, R., et al., Plasma Polymerization: A New Technology for Functional Coatings on Plastics, 36th Annual Technical Conference Proceedings, 1993, ISBN 1-878068-12-1, pp. 51-55.

Izu, M., et al., High Performance Clear CoatTM Barrier Film, 36th Annual Technical Conference Proceedings, 1993, ISBN 1-878068-12-1, pp. 333-340.

Jost, S., Plasma Polymerized Organosilicon Thin Films on Reflective Coatings, 33rd Annual Technical Conference Proceedings, 1990, ISBN 1-878068-09-1, pp. 344-346.

Kaganowicz, G., et al., Plasma-Deposited Coatings—Properties and Applications, 23rd Annual Technical Conference Proceedings, 1980, pp. 24-30.

Kamineni, V. et al., Thickness Measurement of Thin Metal Films by Optical Metrology, College of Nanoscale Science and Engineering, University of Albany, Albany, NY.

Klemberg-Sapieha, J.E., et al., Transparent Gas Barrier Coatings Produced by Dual Frequency PECVD, 36th Annual Technical Conference Proceedings, 1993, ISBN 1-878068-12-1, pp. 445-449.

Krug, T., et al., New Developments in Transparent Barrier Coatings, 36th Annual Technical Conference Proceedings, 1993, ISBN 1-878068-12-1, pp. 302-305.

Kuhr, M. et al., Multifunktionsbeschichtungen für innovative Applikationen von Kunststoff-Substraten, HiCotec Smart Coating Solutions.

Kulshreshtha, D.S., Specifications of a Spectroscopic Ellipsometer, Department of Physics & Astrophysics, University of Delhi, Delhi-110007, Jan. 16, 2009.

Krug, T.G., Transparent Barriers for Food Packaging, 33rd Annual Technical Conference Proceedings, 1990, ISBN 1-878068-09-1, pp. 163-169.

(56) References Cited

OTHER PUBLICATIONS

Lee, K. et al., The Ellipsometric Measurements of a Curved Surface, Japanese Journal of Applied Physics, vol. 44, No. 32, 2005, pp. L1015-L1018.
Lelait, L. et al., Microstructural Investigations of EBPVD Thermal Barrier Coatings, Journal De Physique IV, Colloque C9, supplément au Journal de Physique III, vol. 3, Dec. 1993, pp. 645-654.
Masso, J.D., Evaluation of Scratch Resistant and Antireflective Coatings for Plastic Lenses, 32nd Annual Technical Conference Proceedings, 1989, p. 237-240.
Misiano, C., et al., New Colourless Barrier Coatings (Oxygen & Water Vapor Transmission Rate) on Plastic Substrates, 35th Annual Technical Conference Proceedings, 1992, ISBN 1-878068-11-3, pp. 28-40.
Misiano, C., et al., Silicon Oxide Barrier Improvements on Plastic Substrate, Society of Vacuum Coaters, 34th Annual Technical Conference Proceedings, 1991, ISBN 1-878068-10-5, pp. 105-112.
Mount, E., Measuring Pinhole Resistance of Packaging, Corotec Corporation website, http://www.convertingmagazine.com, printed Jul. 13, 2009.
Murray, L. et al., The Impact of Foil Pinholes and Flex Cracks on the Moisture and Oxygen Barrier of Flexible Packaging.
Nelson, R.J., et al., Double-Sided QLF® Coatings for Gas Barriers, Society of Vacuum Coaters, 34th Annual Technical Conference Proceedings, 1991, ISBN 1-878068-10-5, pp. 113-117.
Nelson, R.J., Scale-Up of Plasma Deposited SiOx Gas Diffusion Barrier Coatings, 35th Annual Technical Conference Proceedings, 1992, ISBN 1-878068-11-3, pp. 75-78.
Novotny, V. J., Ultrafast Ellipsometric Mapping of Thin Films, IBM Technical Disclosure Bulletin, vol. 37, No. 02A, Feb. 1994, pp. 187-188.
Rüger, M., Die Pulse Sind das Plus, PICVD—Beschichtungsverfahren.
Schultz, A. et al., Detection and Identification of Pinholes in Plasma-Polymerised Thin Film Barrier Coatings on Metal Foils, Surface & Coatings Technology 200, 2005, pp. 213-217.
Stchakovsky, M. et al., Characterization of Barrier Layers by Spectroscopic Ellipsometry for Packaging Applications, Horiba Jobin Yvon, Application Note, Spectroscopic Ellipsometry, SE 14, Nov. 2005.
Teboul, E., Thi-Film Metrology: Spectroscopic Ellipsometer Becomes Industrial Thin-Film Tool, LaserFocusWorld, http://www.laserfocusworld.com/display_article, printed Jul. 14, 2009.
Teyssedre, G. et al., Temperature Dependence of the Photoluminescence in Poly(Ethylene Terephthalate) Films, Polymer 42, 2001, pp. 8207-8216.
Tsung, L. et al., Development of Fast CCD Cameras for In-Situ Electron Microscopy, Microsc Microanal 14(Supp 2), 2008.
Wood, L. et al., A Comparison of SiO2 Barrier Coated Polypropylene to Other Coated Flexible Substrates, 35th Annual Technical Conference Proceedings, 1992, ISBN 1-878068-11-3, pp. 59-62.
Yang, et al., Microstructure and tribological properties of SiOx/DLC films grown by PECVD, Surface and Coatings Technology, vol. 194, Issue 1, Apr. 20, 2005, pp. 128-135.
AN 451, Accurate Thin Film Measurements by High-Resoluiton Transmission Electron Microscopy (HRTEM), Evans Alalytical Group, Version 1.0, Jun. 12, 2008, pp. 1-2.
Benefits of TriboGlide, TriboGlide Silicone-Free Lubrication Systems, http://www.triboglide.com/benfits.htm, printed Aug. 31, 2009.
Korean Patent Office, Office Action dated Jun. 21, 2016 in Patent Application No. 10-2011-7028713.
Mexican Patent Office, Office Action dated Jun. 7, 2016 in Patent Application No. MX/a/2011/012038 (3 pages).
Japanese Patent Office, Notice of Reasons for Refusal, Patent Application No. 2013-510276, dated Mar. 8, 2016 (15 pages).
European Patent Office, Communication pursuant to Article 94(3) EPC, in Application No. 13 726 337.2, dated Dec. 2, 2016 (6 pages).
Australian Government, IP Australia, Patent Examination Report No. 1, in Application No. 2010249031, dated Mar. 13, 2014. (4 pages).
Australian Government, IP Australia, Patent Examination Report No. 1, in Application No. 2013202893, dated Mar. 13, 2014. (4 pages).
European Patent Office, Communication pursuant to Article 93(3) EPC, in Application No. 11 731 554.9 dated Apr. 15, 2014. (7 pages).
PCT, Notification Concerning Transmittal of International Preliminary Report on Patentability, in International application No. PCT/US2012/064489, dated May 22, 2014. (10 pages).
PCT, Notification of Transmittal of the International Search Report and the Written Opinion of the International Searching Authority, or the Declaration, in International application No. PCT/US2013/071750, dated Apr. 4, 2014. (13 pages).
PCT, Notification of Transmittal of the International Search Report and the Written Opinion of the International Searching Authority, or the Declaration, in International application No. PCT/US2014/019684, dated May 23, 2014. (16 pages).
PCT, Notification of Transmittal of the International Search Report and the Written Opinion of the International Searching Authority, or the Declaration, in International application No. PCT/US2014/023813, dated May 22, 2014. (11 pages).
European Patent Office, Communication pursuant to Article 94(3) EPC, in Application No. 11 736 511.4, dated Mar. 28, 2014.
PCT, Notification Concerning Transmittal of International Preliminary Report on Patentability, in International application No. PCT/US2011/042387, dated Jan. 17, 2013. (7 pages).
State Intellectual Property Office of the People's Republic of China, Notification of the First Office Action, in Application No. 201180032145.4, dated Jan. 30, 2014. (16 pages).
PCT, Notification Concerning Transmittal of International Preliminary Report on Patentability, in International application No. PCT/US2011/044215, dated Jan. 31, 2013. (14 pages).
Da Silva Sobrinho A S et al., "Transparent barrier coatings on polyethylene terephthalate by single-and dual-frequency plasma-enhanced chemical vapor deposition", Journal of Vacuum Science and Technology; Part A, AVS/AIP, Melville, NY, US, vol. 16, No. 6, Nov. 1, 1998 (Nov. 1, 1998), pp. 3190-3198, XP01200471, ISSN: 0734-2101, DOI: 10.1116/1.581519 (9 pages).
State Intellectual Property Office of the People's Republic of China, Notification of the Third Office Action, in Application No. 201080029201.4, dated Jul. 7, 2014 (15 pages).
PCT, Notification of Transmittal of the International Search Report and the Written Opinion of the International Searching Authority, or the Declaration, in International application No. PCT/US2014/029531, dated Jun. 20, 2014 (12 pages).
State Intellectual Property Office of the People's Republic of China, Notification of the Third Office Action, with translation, in Application No. 201080029199.0, dated Jun. 27, 2014 (19 pages).
Intellectual Property Office of Singapore, Invitation to Respond to Written Opinion, in Application No. 2012083077, dated Jun. 30, 2014 (12 pages).
PCT, Notification of Transmittal of International Preliminary Report on Patentability, in International application No. PCT/US13/40368, dated Jul. 16, 2014 (6 pages).
Australian Government, IP Australia, Patent Examination Report No. 1, in Application No. 2012318242, dated Apr. 30, 2014. (6 pages).
State Intellectual Property Office of the People's Republic of China, Notification of the First Office Action, in Application No. 201180023461.5, dated May 21, 2014. (25 pages).
European Patent Office, Communication pursuant to Article 94(3) EPC, in Application No. 10162758.6 dated May 27, 2014. (7 pages).
Australian Government, IP Australia, Patent Examination Report No. 1, in Application No. 2011252925, dated Sep. 6, 2013 (3 pages).
Coating Syringes, http://www.triboglide.com/syringes.htm, printed Aug. 31, 2009.
Coating/Production Process, http://www.triboglide.com/process.htm, printed Aug. 31, 2009.
Munich Exp, Materialica 2005: Fundierte Einblicke in den Werkstofsektor, Seite 1, von 4, ME095-6.
Schott Developing Syringe Production in United States, Apr. 14, 2009, http://www.schott.com/pharmaceutical_packaging, printed Aug. 31, 2009.

(56) References Cited

OTHER PUBLICATIONS

Sterile Prefillable Glass and Polymer Syringes, Schott forma vitrum, http://www.schott.com/pharmaceutical_packaging.
Transparent and recyclingfähig, neue verpackung, Dec. 2002, pp. 54-57.
European Patent Office, Communication with European Search Report, in Application No. 10162758.6, dated Aug. 19, 2010.
Griesser, Hans J., et al., Elimination of Stick-Slip of Elastomeric Sutures by Radiofrequency Glow Discharge Deposited Coatings, Biomed Mater. Res. Appl Biomater, 2000, vol. 53, 235-243, John Wiley & Sons, Inc.
European Patent Office, Communication with extended Search Report, in Application No. EP 10162761.0, dated Feb. 10, 2011.
European Patent Office, Communication with partial Search Report, in Application No. EP 10162758.6, dated Aug. 19, 2010.
European Patent Office, Communication with extended Search Report, in Application No. EP 10162758.6, dated Dec. 21, 2010.
Yang, et al., Microstructure and tribological properties of SiOx/DLC films grown by PECVD, Surface and Coatings Technology, vol. 194 (2005), Apr. 20, 2005, pp. 128-135.
European Patent Office, Communication with extended European search report, in Application No. EP10162756.0, dated Nov. 17, 2010.
Prasad, G.R. et al., "Biocompatible Coatings with Silicon and Titanium Oxides Deposited by PECVD", 3rd Mikkeli International Industrial Coating Seminar, Mikkeli, Finland, Mar. 16-18, 2006.
European Patent Office, Communication with extended European search report, in Application No. EP10162757.8, dated Nov. 10, 2010.
Patent Cooperation Treaty, Notification of Transmittal of the International Search Report and the Written Opinion of the International Searching Authority, in PCT/US2010/034568, dated Jan. 21, 2011.
Patent Cooperation Treaty, Notification of Transmittal of the International Search Report and the Written Opinion of the International Searching Authority, in PCT/US2010/034571, dated Jan. 26, 2011.
Patent Cooperation Treaty, Notification of Transmittal of the International Search Report and the Written Opinion of the International Searching Authority, in PCT/US2010/034576, dated Jan. 25, 2011.
Patent Cooperation Treaty, Notification of Transmittal of the International Search Report and the Written Opinion of the International Searching Authority, in PCT/US2010/034577, dated Jan. 21, 2011.
Patent Cooperation Treaty, Notification of Transmittal of the International Search Report and the Written Opinion of the International Searching Authority, in PCT/US2010/034582, dated Jan. 24, 2011.
European Patent Office, Communication with Extended Search Report, in Application No. EP 10162755.2, dated Nov. 9, 2010.
European Patent Office, Communication with Extended Search Report, in Application No. EP 10162760.2, dated Nov. 12, 2010.
PCT, Written Opinion of the International Searching Authority with International Search Report in Application No. PCT/US2010/034586, dated Mar. 15, 2011.
Shimojima, Atsushi et al., Structure and Properties of Multilayered Siloxane-Organic Hybrid Films Prepared Using Long-Chain Organotrialkoxysilanes Containing C=C Double Bonds, Journal of Materials Chemistry, 2007, vol. 17, pp. 658-663, © The Royal Society of Chemistry, 2007.
Sone, Hayato et al., Picogram Mass Sensor Using Resonance Frequency Shift of Cantilever, Japanese Journal of Applied Physics, vol. 43, No. 6A, 2004, pp. 3648-3651, © The Japan Society of Applied Physics.
Sone, Hayato et al., Femtogram Mass Sensor Using Self-Sensing Cantilever for Allergy Check, Japanese Journal of Applied Physics, vol. 45, No. 3B, 2006, pp. 2301-2304, © The Japan Society of Applied Physics.
Mallikarjunan, Anupama et al, The Effect of Interfacial Chemistry on Metal Ion Penetration into Polymeric Films, Mat. Res. Soc. Symp. Proc. vol. 734, 2003, © Materials Research Society.
Schonher, H., et al., Friction and Surface Dynamics of Polymers on the Nanoscale by AFM, STM and AFM Studies on (Bio)molecular Systems: Unravelling the Nanoworld. Topics in Current Chemistry, 2008, vol. 285, pp. 103-156, © Springer-Verlag Berlin Heidelberg.
Lang, H.P., Gerber, C., Microcantilever Sensors, STM and AFM Studies on (Bio)molecular Systems: Unravelling the Nanoworld. Topics in Current Chemistry, 2008, vol. 285, pp. 1-28, © Springer-Verlag Berlin Heidelberg.
PCT, Written Opinion of the International Preliminary Examining Authority, in International application No. PCT/USUS13/048709, dated Sep. 30, 2014 (4 pages).
PCT, Notification of Transmittal of the International Preliminary Report on Patentability, in International application No. PCT/USUS13/048709, dated Oct. 15, 2014 (7 pages).
PCT, Written Opinion of the International Preliminary Examining Authority, in International application No. PCT/USUS13/064121, dated Nov. 19, 2014 (8 pages).
PCT, Written Opinion of the International Preliminary Examining Authority, in International application No. PCT/USUS13/064121, dated Nov. 21, 2014 (7 pages).
Intellectual Property Corporation of Malaysia, Substantive Examintion Adverse Report (section 30(1)/30(2)), in Application No. PI 2011005486, dated Oct. 31, 2014 (3 pages).
Patent Office of the Russian Federation, Official Action, in Application No. 2011150499, dated Sep. 25, 2014 (4 pages).
Instituto Mexicano de la Propiedad Indutrial, Official Action, in Appilcation No. MX/a/2012/013129, dated Sep. 22, 2014 (5 pages).
Australian Government, Patent Examination Report No. 2 in Application No. 2010249031 dated Apr. 21, 2015.
Japanese Patent Office, Notice of Reasons for Refusal in application No. 2013-510276, dated Mar. 31, 2015.
Bose, Sagarika and Constable, Kevin, Advanced Delivery Devices, Design & Evaluation of a Polymer-Based Prefillable Syringe for Biopharmaceuticals With Improved Functionality & Performance, JR Automation Technologies, May 2015.
Hopwood J ED—CRC Press: "Plasma-assisted deposition", Aug. 17, 1997 (Aug. 17, 1997), Handbook of Nanophase Materials, Chapter 6, pp. 141-197, XP008107730, ISBN: 978-0-8247-9469-9.
PCT, Written Opinion of the International Preliminary Examining Authority, International application No. PCT/SU2013/071752, dated May 6, 2015.
Hlobik, Plastic Pre-Fillable Syringe Systems (http://www.healthcarepackaging.com/package-type/Containers/plastic-prefillablesyringe-systems, Jun. 8, 2010).
PCT, Written Opinion of the International Preliminary Examining Authority, in International application No. PCT/US2013/071750, dated Jan. 20, 2015 (9 pages).
PCT, Written Opinion of the International Preliminary Examining Authority, in International application No. PCT/US2013/064121, dated Nov. 21, 2014 (7 pages).
Japanese Patent Office, Decision of Rejection in Application No. 2012-510983, dated Jan. 20, 2015 (4 pages).
Australian Government, IP Australia, Patent Examination Report No. 1, in Application No. 2010249033, dated Dec. 19, 2014 (7 pages).
Australian Government, IP Australia, Patent Examination Report No. 1, in Application No. 2011252925, dated Dec. 2, 2014 (3 pages).
State Intellectual Property Office of the People's Republic of China, Notification of the Fourth Office Action in Application No. 201080029199.0, dated Mar. 18, 2015 (15 pages).
Reh, et al., Evaluation of stationary phases for 2-dimensional HPLC of Proteins—Validation of commercial RP-columns, Published by Elsevier B.V., 2000.
L. Martinu, O. Zabeida, and J.E. Klemberg-Sapieha, "Plasma-Enhanced Chemical Vapor Deposition of Functional Coatings", Handbook of Deposition Technologies for Films and Coating, Chapter 9, pp. 392-464, 2010.

\* cited by examiner

CYCLIC OLEFIN POLYMER VESSELS AND VESSEL COATING METHODS

This application is a Continuation of U.S. patent application Ser. No. 13/240,797, filed Sep. 22, 2011 which claims the priority of U.S. Provisional Ser. No. 61/413,355, filed Nov. 12, 2010.

U.S. Provisional Ser. No. 61/177,984 filed May 13, 2009; 61/222,727, filed Jul. 2, 2009; 61/213,904, filed Jul. 24, 2009; 61/234,505, filed Aug. 17, 2009; 61/261,321, filed Nov. 14, 2009; 61/263,289, filed Nov. 20, 2009; 61/285,813, filed Dec. 11, 2009; 61/298,159, filed Jan. 25, 2010; 61/299,888, filed Jan. 29, 2010; 61/318,197, filed Mar. 26, 2010, and 61/333,625, filed May 11, 2010; 61/413,334, filed Nov. 12, 2010; 61/413,355, filed Nov. 12, 2010; U.S. Ser. No. 12/779,007, filed May 12, 2010; and PCT/US11/36097, filed May 11, 2011, are all incorporated here by reference in their entirety.

Also incorporated by reference in their entirety are the following European patent applications: EP10162755.2 filed May 12, 2010; EP10162760.2 filed May 12, 2010; EP10162756.0 filed May 12, 2010; EP10162758.6 filed May 12, 2010; EP10162761.0 filed May 12, 2010; and EP10162757.8 filed May 12, 2010.

BACKGROUND OF THE INVENTION

The present invention relates to the technical field of fabrication of coated vessels for storing proteins, peptides, DNA strands or fragments, other biologically active compounds, or blood. For example, the invention relates to a vessel processing system for coating of a vessel, vessel processing system for coating and inspection of a vessel, to a portable vessel holder for a vessel processing system, to a plasma enhanced chemical vapour deposition apparatus for coating an interior surface of a vessel, to a method for coating an interior surface of a vessel, to a method for coating and inspection of a vessel, to a method of processing a vessel, to the use of a vessel processing system, to a computer-readable medium and to a program element.

The present disclosure also relates to improved methods for processing vessels, for example multiple identical vessels used for venipuncture and other medical sample collection, pharmaceutical preparation storage and delivery, and other purposes. Such vessels are used in large numbers for these purposes, and must be relatively economical to manufacture and yet highly reliable in storage and use.

U.S. Pat. No. 6,680,091, issued to Buch-Rasmussen et al., discloses medicament containers made in whole or part of cyclic olefin copolymer (COC) resin and intended, for example, for containing one or more active medicaments comprising proteins, peptides, and/or DNA sequences; water; and at least one organic preservative, for example but not limited to a preservative for the active medicament selected from m-cresol, benzyl alcohol, and phenol. See also Example 1 and Table 2 of the '091 patent, showing as a comparative example a container said to be made of CZ resin. The '091 patent states at col. 8, lines 4-6, "The CZ-resin is studied as comparison, the ethylene content of CZ-resin being 0, whereby the cyclic component constitutes 100% of the polymer."

Prefilled syringes are commonly prepared and sold so the syringe does not need to be filled before use. The syringe can be prefilled with saline solution, a dye for injection, or a pharmaceutically active preparation, for some examples. Other suitable examples are prefilled syringes for storing proteins, peptides, DNA strands or fragments, other biologically active compounds, or blood. Vials and other containers for medicaments, and in particular for storing proteins, peptides, DNA strands or fragments, and other biologically active compounds, are also known.

Commonly, a prefilled syringe is capped at the distal end, as with a cap, and is closed at the proximal end by its drawn plunger. The prefilled syringe can be wrapped in a sterile package before use. To use the prefilled syringe, the packaging and cap are removed, optionally a hypodermic needle or another delivery conduit is attached to the distal end of the barrel, the delivery conduit or syringe is moved to a use position (such as by inserting the hypodermic needle into a patient's blood vessel or into apparatus to be rinsed with the contents of the syringe), and the plunger is advanced in the barrel to inject the contents of the barrel.

One important consideration in manufacturing pre-filled syringes is that the contents of the syringe desirably will have a substantial shelf life, during which it is important to isolate the material filling the syringe from the barrel wall containing it, to avoid leaching material from the barrel into the prefilled contents or vice versa.

Since many of these vessels are inexpensive and used in large quantities, for certain applications it will be useful to reliably obtain the necessary shelf life without increasing the manufacturing cost to a prohibitive level. It is also desirable for certain applications to move away from glass vessels, which can break and are expensive to manufacture, in favor of plastic vessels which are rarely broken in normal use (and if broken do not form sharp shards from remnants of the vessel, like a glass tube would). Glass vessels have been favored because glass is more gas tight and inert to pre-filled contents than untreated plastics. Also, due to its traditional use, glass is well accepted, as it is known to be relatively innocuous when contacted with medical samples or pharmaceutical preparations and the like.

A further consideration when regarding syringes is to ensure that the plunger can move at a constant speed and with a constant force when it is pressed into the barrel. For this purpose, a lubricity layer, either on one or on both of the barrel and the plunger, is desirable.

A non-exhaustive list of patents of possible relevance includes U.S. Pat. Nos. 6,068,884 and 4,844,986 and U.S. Published Applications 20060046006 and 20040267194.

SUMMARY OF THE INVENTION

Certain aspects of the present invention relate to the technical field of coated vessels made in whole or part of cyclic olefin polymer (COP), optionally suited for storing proteins, peptides, DNA strands or fragments, other biologically active compounds, or blood. Certain aspects of the invention relate to a method for coating an interior surface of a vessel or to a method for coating and inspection of a vessel.

The present disclosure also relates to improved methods for processing COP vessels, for example multiple identical vessels used for venipuncture and other medical sample collection, pharmaceutical preparation storage and delivery, and other purposes. Such vessels are used in large numbers for these purposes, and must be relatively economical to manufacture and yet highly reliable in storage and use.

An aspect of the invention is a package containing a pharmaceutical composition, the package including a container, a coating, and a composition.

The container comprises a wall defining a lumen. At least a portion of the wall defining the lumen is made of a cyclic olefin polymer.

The coating is present on at least a portion of the lumen. The coating includes a material having the atomic ratio $SiO_x$, in which x is from 1.5 to 2.9, or the atomic ratio $Si_wO_xC_y$, where w is 1, x in this formula is from about 0.5 to 2.4, and y is from about 0.6 to about 3. The atomic ratio is measured by X-ray photoelectron spectroscopy (XPS).

The composition contained in the lumen includes (A) one or more active medicaments which are proteins, peptides, and/or DNA sequences; (B) water; and (C) optionally, at least one organic preservative.

In certain optional embodiments, the container comprises a syringe barrel.

In certain optional embodiments, the coating comprises a barrier coating of $SiO_x$.

In certain optional embodiments, the package further includes, between the barrier coating and the lumen, a second coating or layer. The second coating or layer has the following atomic ratio, measured by X-ray photoelectron spectroscopy (XPS), $Si_wO_xC_y$ where w is 1, x in this formula is from about 0.5 to 2.4, and y is from about 0.6 to about 3.

In certain optional embodiments, the package further includes a stopper, plunger or piston located at least partially within the lumen and slidable in the lumen along the container wall.

In certain optional embodiments, the second coating or layer reduces the sliding friction between the container wall and the stopper, plunger or piston.

In certain optional embodiments, the second coating or layer is $Si_wO_xC_y$ applied by chemical vapor deposition, employing as the gaseous reactant or process gas, from 1 to 6 standard volumes of an organosilicon precursor, from 1 to 100, optionally from 5 to 100, optionally from 10-70 standard volumes of a carrier gas, and from 0.1 to 2, optionally from 0.2 to 1.5, optionally from 0.2 to 1, optionally from 0.5 to 1.5, optionally from 0.8 to 1.2 standard volumes of an oxidizing agent.

In certain optional embodiments, the package includes an organic preservative.

In certain optional embodiments, the organic preservative includes at least one of m-cresol, benzyl alcohol, and phenol.

In certain optional embodiments, the one or more active medicaments includes pharmaceutical insulin.

In certain optional embodiments, a plunger or piston is included. The plunger or piston has a front face, a side portion, and a back portion, the side portion being configured to movably seat within a syringe barrel, at least a portion of the front face made of cyclic olefin polymer resin.

Certain optional embodiments include a medical or diagnostic kit including the package of any embodiment above; a hypodermic needle, double-ended needle, or other delivery conduit; and optionally, an instruction sheet.

Certain optional embodiments include use of the second coating for coating a surface and thereby preventing or reducing mechanical and/or chemical effects of the surface on a compound or composition in contact with the coating.

Certain optional embodiments include use of the second coating as a lubricity layer.

Certain optional embodiments include use of the barrier coating, the second coating, or a combination including the two for protecting a compound or composition contacting the coating against mechanical and/or chemical effects of the surface of the uncoated vessel material.

Certain optional embodiments include use of the package for preventing or reducing precipitation and/or clotting or platelet activation of a compound or a component of the composition in contact with the coating.

Certain optional embodiments include the package described above, in which the one or more active medicaments includes insulin, and wherein precipitation of the insulin is prevented or reduced.

In certain optional embodiments, the one or more active medicaments include blood or a blood fraction, and blood clotting or platelet activation is prevented or reduced.

Certain optional embodiments include use of a package for storing insulin.

Other aspects of the invention will become apparent to a person of ordinary skill in the art after reviewing the present disclosure and claims.

BRIEF DESCRIPTION OF THE DRAWINGS

FIG. 11 also shows an alternative syringe barrel construction usable, for example, with the embodiments of FIGS. 1, 2, 3, 7, 8, and 9.

Figure 1:
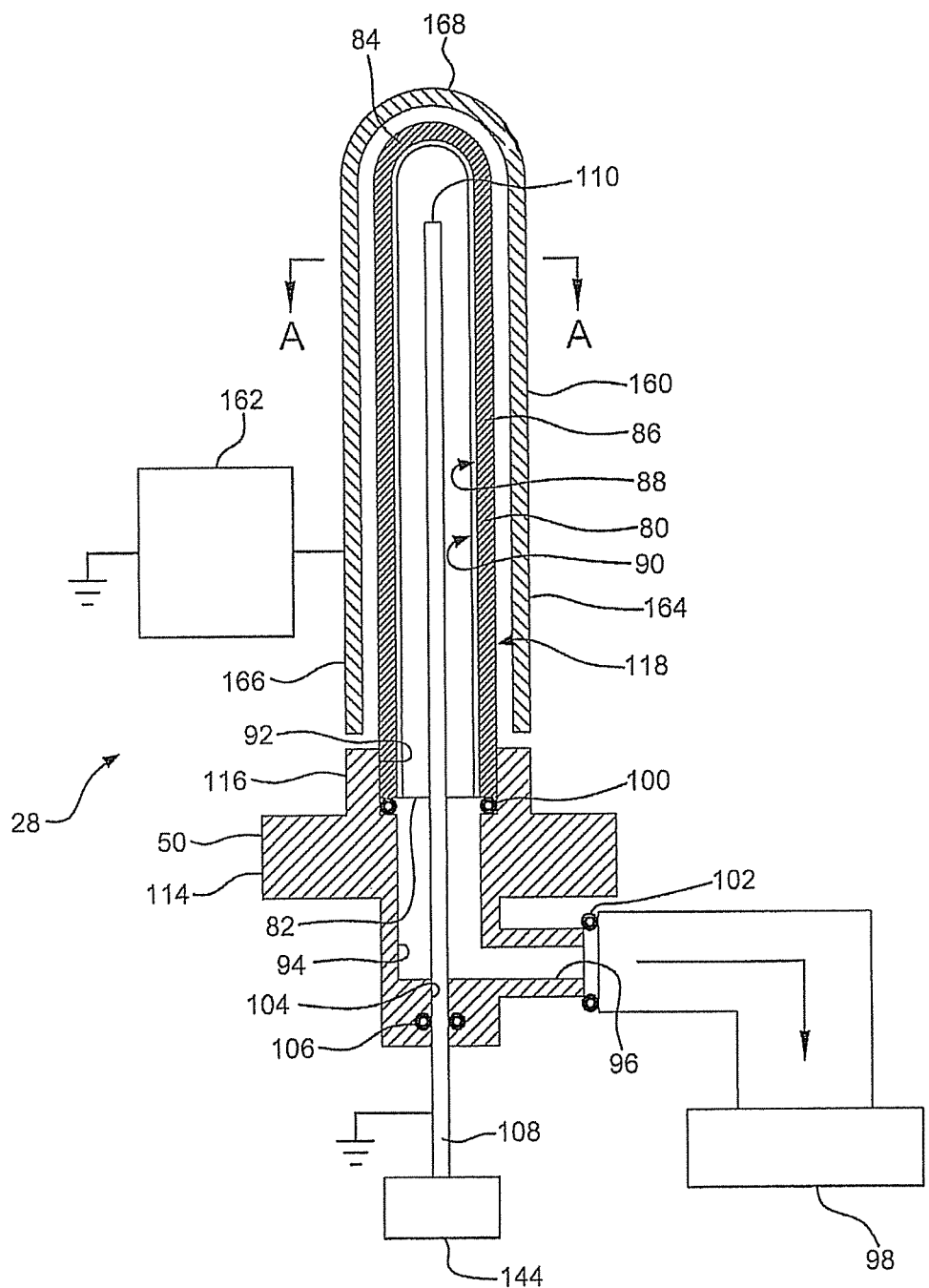
FIG. 1 is a schematic sectional view of a vessel holder in a coating station according to an embodiment of the disclosure.

The following reference characters are used in the drawing figures:

| | |
|---|---|
| 20 | Vessel processing system |
| 28 | Coating station |
| 38 | Vessel holder |
| 50 | Vessel holder |
| 70 | Conveyor |
| 72 | Transfer mechanism (on) |
| 74 | Transfer mechanism (off) |
| 80 | Vessel |
| 82 | Opening |
| 84 | Closed end |
| 86 | Wall |
| 88 | Interior surface |
| 90 | Barrier layer |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (counter electrode) |
| 110 | Gas delivery port (of 108) |
| 114 | Housing (of 50 or 112) |
| 116 | Collar |
| 118 | Exterior surface (of 80) |
| 144 | PECVD gas source |
| 152 | Pressure gauge |
| 160 | Electrode |
| 162 | Power supply |
| 164 | Sidewall (of 160) |
| 166 | Sidewall (of 160) |
| 168 | Closed end (of 160) |
| 200 | Electrode |
| 250 | Syringe barrel |
| 252 | Syringe |
| 254 | Interior surface (of 250) |
| 256 | Back end (of 250) |
| 258 | Plunger (of 252) |
| 260 | Front end (of 250) |
| 262 | Cap |
| 264 | Interior surface (of 262) |
| 268 | Vessel |
| 270 | Closure |
| 272 | Interior facing surface |
| 274 | Lumen |
| 276 | Wall-contacting surface |
| 278 | Inner surface (of 280) |
| 280 | Vessel wall |
| 282 | Stopper |
| 284 | Shield |
| 286 | Lubricity layer |
| 288 | Barrier layer |
| 290 | Apparatus for coating, for example, 250 |
| 292 | Inner surface (of 294) |
| 294 | Restricted opening (of 250) |
| 296 | Processing vessel |
| 298 | Outer surface (of 250) |
| 300 | Lumen (of 250) |
| 302 | Larger opening (of 250) |
| 304 | Processing vessel lumen |
| 306 | Processing vessel opening |
| 308 | Inner electrode |
| 310 | Interior passage (of 308) |
| 312 | Proximal end (of 308) |
| 314 | Distal end (of 308) |
| 316 | Distal opening (of 308) |
| 318 | Plasma |
| 332 | First fitting (male Luer taper) |
| 334 | Second fitting (female Luer taper) |
| 336 | Locking collar (of 332) |
| 338 | First abutment (of 332) |
| 340 | Second abutment (of 332) |
| 342 | O-ring |

-continued

Figure 10:
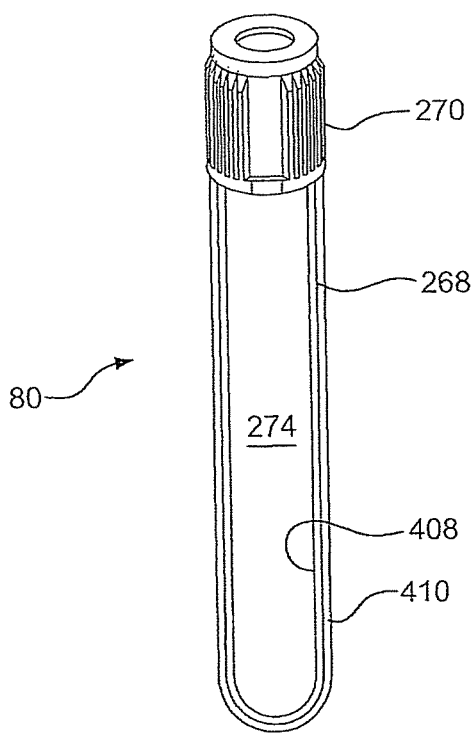
FIG. 10 is a perspective view of a double-walled blood collection tube assembly according to still another embodiment of the invention.

| | |
|---|---|
| 344 | Dog |
| 408 | Inner wall (FIG. 10) |
| 410 | Outer wall (FIG. 10) |
| 482 | Vessel holder body |
| 484 | Upper portion (of 482) |
| 486 | Base portion (of 482) |
| 488 | Joint (between 484 and 486) |
| 490 | O-ring |
| 492 | Annular pocket |
| 494 | Radially extending abutment surface |
| 496 | Radially extending wall |
| 498 | Screw |
| 500 | Screw |
| 502 | Vessel port |
| 504 | Second O-ring |
| 506 | Inner diameter (of 490) |
| 508 | Vacuum duct (of 482) |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Organosilicon liquid reservoir |
| 590 | Organosilicon feed line (capillary) |
| 592 | Organosilicon shut-off valve |
| 594 | Oxygen tank |
| 596 | Oxygen feed line |
| 598 | Mass flow controller |
| 600 | Oxygen shut-off valve |
| 614 | Headspace |
| 616 | Pressure source |
| 618 | Pressure line |
| 620 | Capillary connection |
| 5501 | First processing station |
| 5502 | Second processing station |
| 5503 | Third processing station |
| 5504 | Fourth processing station |
| 5505 | Processor |
| 5506 | User interface |
| 5507 | Bus |
| 5701 | PECVD apparatus |
| 5702 | First detector |
| 5703 | Second detector |
| 5704 | Detector |
| 5705 | Detector |
| 5706 | Detector |
| 5707 | Detector |
| 7001 | Conveyor exit branch |
| 7002 | Conveyor exit branch |
| 7003 | Conveyor exit branch |
| 7004 | Conveyor exit branch |

DETAILED DESCRIPTION OF THE PREFERRED EMBODIMENTS

The present invention will now be described more fully with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

Definition Section

In the context of the present invention, the following definitions and abbreviations are used:

RF is radio frequency; sccm is standard cubic centimeters per minute.

The term "at least" in the context of the present invention means "equal or more" than the integer following the term. The word "comprising" does not exclude other elements or steps, and the indefinite article "a" or "an" does not exclude a plurality unless indicated otherwise.

"First" and "second" or similar references to, e.g., coatings, layers, processing stations or processing devices refer to the minimum number of coatings, layers, processing stations or devices that are present, but do not necessarily represent the order or total number of processing stations and devices. These terms do not limit the number of processing stations or the particular processing carried out at the respective stations.

For purposes of the present invention, an "organosilicon precursor" is a compound having at least one of the linkage:

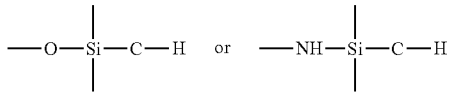

which is a tetravalent silicon atom connected to an oxygen or nitrogen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, a linear silazane, a monocyclic silazane, a polycyclic silazane, a polysilsesquiazane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, in the working examples the flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be any type of vessel with at least one opening and a wall defining an interior surface. The substrate can be the inside wall of a vessel having a lumen. Though the invention is not necessarily limited to vessels of a particular volume, vessels are contemplated in which the lumen has a void volume of from 0.5 to 50 mL, optionally from 1 to 10 mL, optionally from 0.5 to 5 mL, optionally from 1 to 3 mL. The substrate surface can be part or all of the inner surface of a vessel having at least one opening and an inner surface.

The term "at least" in the context of the present invention means "equal or more" than the integer following the term. Thus, a vessel in the context of the present invention has one or more openings. One or two openings, like the openings of a sample tube (one opening) or a syringe barrel (two openings) are preferred. If the vessel has two openings, they can be of same or different size. If there is more than one opening, one opening can be used for the gas inlet for a PECVD coating method according to the present invention, while the other openings are either capped or open. A vessel according to the present invention can be a sample tube, e.g. for collecting or storing biological fluids like blood or urine, a syringe (or a part thereof, for example a syringe barrel) for storing or delivering a biologically active compound or composition, e.g. a medicament or pharmaceutical composition, a vial for storing biological materials or biologically active compounds or compositions, a pipe, e.g. a catheter for transporting biological materials or biologically active compounds or compositions, or a cuvette for holding fluids, e.g. for holding biological materials or biologically active compounds or compositions.

A vessel can be of any shape, a vessel having a substantially cylindrical wall adjacent to at least one of its open ends being preferred. Generally, the interior wall of the vessel is cylindrically shaped, like, e.g. in a sample tube or a syringe barrel. Sample tubes and syringes or their parts (for example syringe barrels) are contemplated. Vials and other containers are also contemplated.

A "hydrophobic layer" in the context of the present invention means that the coating lowers the wetting tension of a surface coated with the coating, compared to the corresponding uncoated surface. Hydrophobicity is thus a function of both the uncoated substrate and the coating. The same applies with appropriate alterations for other contexts wherein the term "hydrophobic" is used. The term "hydrophilic" means the opposite, i.e. that the wetting tension is increased compared to reference sample. The present hydrophobic layers are primarily defined by their hydrophobicity and the process conditions providing hydrophobicity, and optionally can have a composition according to the empirical composition or sum formula $Si_wO_xC_yH_z$, for example where w is 1, x is from about 0.5 to about 2.4, y is from about 0.6 to about 3, and z is from about 2 to about 9, optionally where w is 1, x is from about 0.5 to 1, y is from about 2 to about 3, and z is from 6 to about 9. These values of w, x, y, and z are applicable to the empirical composition $Si_wO_xC_yH_z$ throughout this specification. The values of w, x, y, and z used throughout this specification should be understood as ratios or an empirical formula (e.g. for a coating), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$. If XPS analysis is used, the value of z is not determined, so these formulations can alternatively be expressed by omitting the $H_z$ term, and then the presence in any quantity or absence of hydrogen is not pertinent.

"Wetting tension" is a specific measure for the hydrophobicity or hydrophilicity of a surface. An optional wetting tension measurement method in the context of the present invention is ASTM D 2578 or a modification of the method described in ASTM D 2578. This method uses standard wetting tension solutions (called dyne solutions) to determine the solution that comes nearest to wetting a plastic film surface for exactly two seconds. This is the film's wetting tension. The procedure utilized is varied herein from ASTM D 2578 in that the substrates are not flat plastic films, but are tubes made according to the Protocol for Forming PET Tube and (except for controls) coated according to the Protocol for Coating Tube Interior with Hydrophobic Layer or coating (see Example 9).

A "lubricity layer" according to the present invention is a coating which has a lower frictional resistance than the uncoated surface. In other words, it reduces the frictional resistance of the coated surface in comparison to a reference surface that is uncoated. The present lubricity layers are primarily defined by their lower frictional resistance than the uncoated surface and the process conditions providing lower frictional resistance than the uncoated surface, and optionally can have a composition according to the empirical composition $Si_wO_xC_y$, as defined in this Definition Section. "Frictional resistance" can be static frictional resistance and/or kinetic frictional resistance.

One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer or coating in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" in the context of the present invention is the force required to maintain movement of a plunger in a syringe barrel, e.g. during aspiration or dispense. It can advantageously be determined using the ISO 7886-1:1993 test described herein and known in the art. A synonym for "plunger sliding force" often used in the art is "plunger force" or "pushing force".

The "breakout force" in the context of the present invention is the initial force required to move the plunger in a syringe, for example in a prefilled syringe.

Both "plunger sliding force" and "breakout force" and methods for their measurement are described in more detail in subsequent parts of this description.

Sliding force and breakout force are sometimes used herein to describe the forces required to advance a stopper or other closure into a vessel, such as a medical sample tube or a vial, to seat the stopper in a vessel to close the vessel. Its use is analogous to use in the context of a syringe and its plunger, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger, closure, or other removable part is permitted to slide in a syringe barrel or other vessel.

In the context of this invention, "substantially rigid" means that the assembled components (ports, duct, and housing, explained further below) can be moved as a unit by handling the housing, without significant displacement of any of the assembled components respecting the others. Specifically, none of the components are connected by hoses or the like that allow substantial relative movement among the parts in normal use. The provision of a substantially rigid relation of these parts allows the location of the vessel seated on the vessel holder to be nearly as well known and precise as the locations of these parts secured to the housing.

One Preferred Embodiment

One preferred embodiment of the invention has the following characteristics.

A package containing a pharmaceutical composition is provided. The package comprises a container, a coating, and a composition. The container comprises a wall defining a lumen, in which at least a portion of the wall defining the lumen is made of a cyclic olefin polymer. The coating is present on at least a portion of the lumen. The coating consists essentially of a barrier coating of a material comprising the atomic ratio $SiO_x$ measured by X-ray photoelectron spectroscopy (XPS), in which x is from 1.5 to 2.9. The barrier coating is applied by chemical vapor deposition.

The composition contained in the lumen comprises pharmaceutical insulin and water.

Between the barrier coating and the lumen, a second coating is provided having the following atomic ratio, measured by X-ray photoelectron spectroscopy (XPS), $Si_wO_xC_y$, where w is 1, x in this formula is from about 0.5 to 2.4, and y is from about 0.6 to about 3.

The second coating is applied by chemical vapor deposition, employing as the gaseous reactant or process gas,
  from 1 to 6 standard volumes of an organosilicon precursor,
  from 1 to 100 standard volumes of a carrier gas, and
  from 0.1 to 2 standard volumes of an oxidizing agent.

Optional Further Features of the One Preferred Embodiment

The composition contained in the lumen optionally further includes at least one organic preservative. The organic preservative can comprise at least one of m-cresol, benzyl alcohol, and phenol, optionally a combination of any two of them or all three of them.

The container optionally comprises a syringe barrel. If a syringe barrel is used, the package optionally further comprises a plunger or piston located at least partially within the lumen and slidable in the lumen along the container wall.

The second coating or layer optionally is a lubricity coating that reduces the sliding friction between the container wall and the plunger or piston.

The plunger or piston optionally has a front face, a side portion, and a back portion, the side portion being configured to movably seat within a syringe barrel. Optionally, at least a portion of the front face is made of cyclic olefin polymer resin.

The embodiment optionally is provided in the form of a medical or diagnostic syringe kit comprising the package; a hypodermic needle, double-ended needle, or other delivery conduit; and optionally, an instruction sheet.

More General Disclosure

More generally, the following technology can be practiced according to many variations without departing from the broad scope of the invention. Some of those variations follow.

Making Vessels

The vessels used in this disclosure can be made of any suitable material, in any suitable manner, for containing medicaments. Examples of suitable containers include blood collection tubes, closed-ended sample collection tubes; vials; conduits; cuvettes; ampoules, or vessel parts, for example a stopper; or a syringe, or a syringe part, for example a barrel or piston, for reception and/or storage and/or delivery of a compound or composition. Syringes as used here include autoinjectors, "pens," and other dispensing vessels having a piston and cylinder arrangement for dispensing a medicament through a needle, cannula, or other dispensing outlet. The piston can also be external to the vessel, and be applied to the vessel to complete a piston and cylinder arrangement. All such vessels known for containing and dispensing medicaments are contemplated for use according to the present disclosure. The central feature of any contemplated vessel is a lumen defined by a wall in which material to be dispensed can be contained. Optionally but not necessarily, the vessel can also include a further element, such as a stopper, septum, cap, plunger (as in a syringe), piston, or the like for closing the lumen to prevent the entry or escape of material into or from the lumen. This optional element is not essential if the material is maintained in an open lumen, as by gravity, or if the wall is a complete enclosure for the contents, as is commonly the case for an ampoule.

The vessels or their various parts can be made of any known material. Examples of suitable materials include but are not limited to polyesters, polyolefins, and other materials. Suitable polyesters include polyethylene terephthalate, polyethylene naphthalate, and others. Suitable polyolefins include polyethylene, polypropylene, and cyclic olefin polymers and copolymers.

In the present disclosure, it is preferred that at least some part of the vessel defining the lumen be made of a cyclic olefin polymer or COP. In particular, the cyclic olefin polymer to be used is defined as optionally containing less than 20%, optionally less than 10%, optionally less than 5%, optionally less than 1%, optionally free of a comonomer such as polyethylene.

Analogous to the explanation of COC copolymers in U.S. Pat. No. 6,680,091, the olefin portion of COP can be "composed of aliphatic cyclic or bicyclic hydrocarbons with 5 to 7 membered ring or rings and" the above-defined optional minor proportions of "ethylene or propylene, the material having a glass transition temperature above 50° C., measured by differential scanning calorimetry, by cutting pieces from the container walls and heating them in an aluminium pan from 10° C. to 270° C. at a scanning rate of 10° C./min, the glass transition temperature being determined as the temperature at the inflection point, and a density of 0.95 g/cm$_3$ or more."

The COP "material may comprise up to 5% by weight of additives in particular selected from antioxidants, lubricants such as stearates and silicones, surface active agents, nucleating and clarifying agents, and up to 30% by weight of inert fillers, such as glass particles having a refractive index about equal to the refractive index of the polymer material, the total amount of additives and fillers being up to 30% by weight."

One suitable cyclic olefin polymer preferred here is Crystal Zenith or "CZ" resin. CZ is a tradename of by Daikyo Gomu Seiko Ltd. (Tokyo, Japan).

The vessel may be made in any suitable or known manner, such as injection molding, blow molding, extrusion and fabrication from extruded tubing, dip molding, and others. Presently preferred is injection molding as it allows a high throughput, high uniformity, and high quality product at a relatively low cost.

VII.A.1.c. SiO$_x$ Barrier Coated Double Wall Plastic Vessel—COP, COC, PET, SiO$_x$ Layers VII.A.1.c. Other embodiments have an interior polymer layer or coating enclosed by an exterior polymer layer. One of the polymer layers is a layer or coating at least 0.1 mm thick of a cyclic olefin polymer (COP) resin. Another of the polymer layers is a layer or coating at least 0.1 mm thick of a polyester resin.

VII.A.1.c. The wall includes an oxygen barrier layer or coating of SiO$_x$ having a thickness of from about 10 to about 500 angstroms.

VII.A.1.c. In an embodiment, illustrated in FIG. 10, the vessel 80 can be a double-walled vessel having an inner wall 408 and an outer wall 410, respectively made of the same or different materials. One particular embodiment of this type can be made with one wall molded from a cyclic olefin polymer (COP) and the other wall molded from COC (cyclic olefin copolymer), for example as defined in U.S. Pat. No. 6,680,091, or a polyester such as polyethylene terephthalate (PET), in either case with an SiO$_x$ coating as previously described on the interior surface 412. As needed, a tie coating or layer or coating can be inserted between the inner and outer walls to promote adhesion between them. An advantage of this wall construction is that walls having different properties can be combined to form a composite having the respective properties of each wall.

VII.A.1.c. As one example, the inner wall 408 can be made of PET coated on the interior surface 412 with an SiO$_x$ barrier layer, and the outer wall 410 can be made of COP. PET coated with SiO$_x$, as shown elsewhere in this specification, is an excellent oxygen barrier, while COP is useful as barrier for water vapor, providing a low water vapor transition rate (WVTR). This composite vessel can have superior barrier properties for both oxygen and water vapor. This construction is contemplated, for example, for an evacuated medical sample collection tube that contains an aqueous reagent as manufactured, and has a substantial shelf life, so it should have a barrier preventing transfer of water vapor outward or transfer of oxygen or other gases inward through its composite wall during its shelf life.

VII.A.1.c. As another example, the inner wall 408 can be made of COP coated on the interior surface 412 with an SiO$_x$ barrier layer, and the outer wall 410 can be made of PET. This construction is contemplated, for example, for a pre-filled syringe that contains an aqueous sterile fluid as manufactured. The SiO$_x$ barrier will prevent oxygen from entering the syringe through its wall. The COP inner wall will prevent ingress or egress of other materials such as water, thus preventing the water in the aqueous sterile fluid from leaching materials from the wall material into the syringe. The COP inner wall is also contemplated to prevent water derived from the aqueous sterile fluid from passing out of the syringe (thus undesirably concentrating the aqueous sterile fluid), and will prevent non-sterile water or other fluids outside the syringe from entering through the syringe wall and causing the contents to become non-sterile. The COP inner wall is also contemplated to be useful for decreasing the breaking force or friction of the plunger against the inner wall of a syringe.

VII.A.1.d. Method of Making Double Wall Plastic Vessel—COP, COC, PET, $SiO_x$ Layers VII.A.1.d. Another embodiment is a method of making a vessel having a wall having an interior polymer layer or coating enclosed by an exterior polymer layer, one layer or coating made of COP and the other made of polyester. The vessel is made by a process including introducing COP and polyester resin layers into an injection mold through concentric injection nozzles.

VII.A.1.d. An optional additional step is applying an amorphous carbon coating to the vessel by PECVD, as an inside coating, an outside coating, or as an interlayer or coating located between the layers.

VII.A.1.d. An optional additional step is applying an $SiO_x$ barrier layer or coating to the inside of the vessel wall, where $SiO_x$ is defined as before. Another optional additional step is post-treating the $SiO_x$ layer or coating with a gaseous reactant or process gas consisting essentially of oxygen and essentially free of a volatile silicon compound.

VII.A.1.d. Optionally, the $SiO_x$ coating can be formed at least partially from a silazane feed gas.

VII.A.1.d. The vessel 80 shown in FIG. 10 can be made from the inside out, for one example, by injection molding the inner wall in a first mold cavity, then removing the core and molded inner wall from the first mold cavity to a second, larger mold cavity, then injection molding the outer wall against the inner wall in the second mold cavity. Optionally, a tie layer or coating can be provided to the exterior surface of the molded inner wall before over-molding the outer wall onto the tie layer.

VII.A.1.d. Or, the vessel 80 shown in FIG. 10 can be made from the outside in, for one example, by inserting a first core in the mold cavity, injection molding the outer wall in the mold cavity, then removing the first core from the molded first wall and inserting a second, smaller core, then injection molding the inner wall against the outer wall still residing in the mold cavity. Optionally, a tie layer or coating can be provided to the interior surface of the molded outer wall before over-molding the inner wall onto the tie layer.

VII.A.1.d. Or, the vessel 80 shown in FIG. 10 can be made in a two shot mold. This can be done, for one example, by injection molding material for the inner wall from an inner nozzle and the material for the outer wall from a concentric outer nozzle. Optionally, a tie layer or coating can be provided from a third, concentric nozzle disposed between the inner and outer nozzles. The nozzles can feed the respective wall materials simultaneously. One useful expedient is to begin feeding the outer wall material through the outer nozzle slightly before feeding the inner wall material through the inner nozzle. If there is an intermediate concentric nozzle, the order of flow can begin with the outer nozzle and continue in sequence from the intermediate nozzle and then from the inner nozzle. Or, the order of beginning feeding can start from the inside nozzle and work outward, in reverse order compared to the preceding description.

Figure 3:
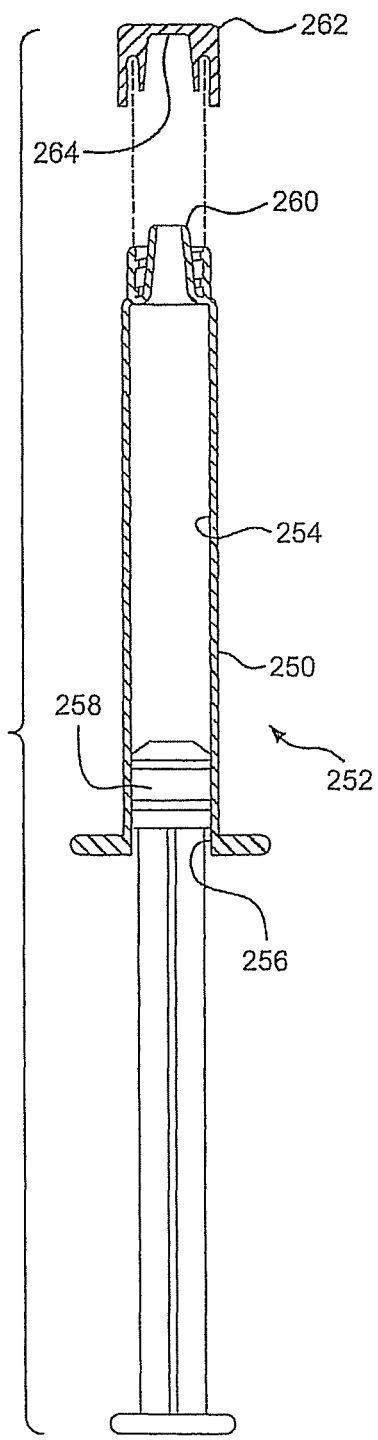
FIG. 3 is an exploded longitudinal sectional view of a syringe and cap adapted for use as a prefilled syringe.

An embodiment of the present invention can be made by applying a coating such as 90 to a substrate such as the vessel 80 (FIG. 1), the vessel 268 (FIG. 10), the stopper 282 (FIGS. 5-6), or the syringe 252 (FIG. 3). The method can be used with any disclosed embodiment. The method includes providing a substrate, for example any of those mentioned above; providing a vaporizable organosilicon precursor, for example any of those disclosed in this specification; and applying the precursor to the substrate by chemical vapor deposition. The precursor is applied, for example in the apparatus of FIG. 1, 26 or any other embodiment, under conditions effective to form a coating.

A gaseous reactant or process gas can be employed having a standard volume ratio of, for example:
    from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor;
    from 1 to 100 standard volumes, optionally from 5 to 100 standard volumes, optionally from 10 to 70 standard volumes, of a carrier gas;
    from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

Figure 6:
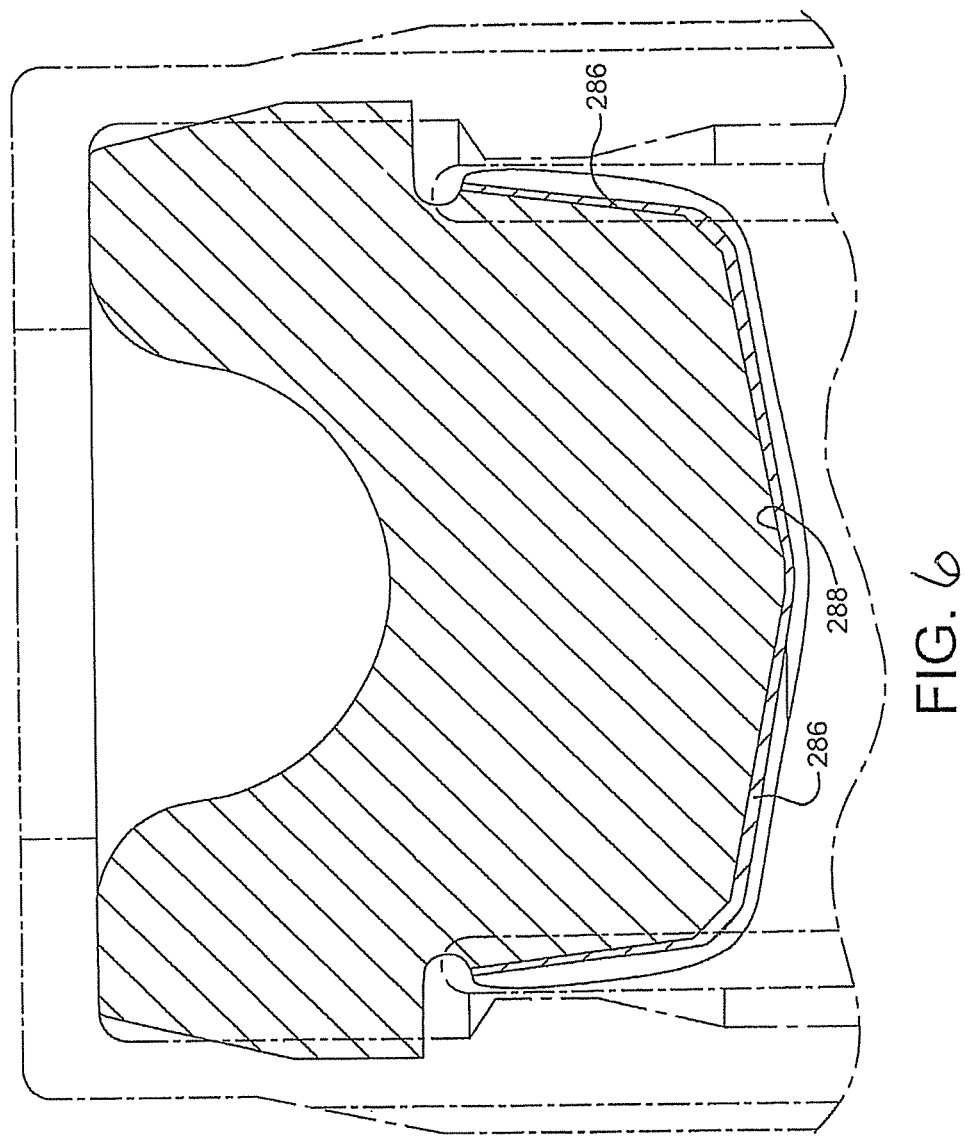
FIG. 6 is an isolated section of an elastomeric insert of a closure.

Another embodiment is a coating, for example 286 in FIG. 6 or a comparable coating in any embodiment, of the type made by the above process.

Another embodiment is a vessel such as the vessel 80 (FIG. 1), the vessel 268 (FIG. 10), or the syringe 252 (FIG. 3) including a lumen defined by a surface defining a substrate. A coating is present on at least a portion of the substrate. The coating is made by the previously defined process.

Figure 13:
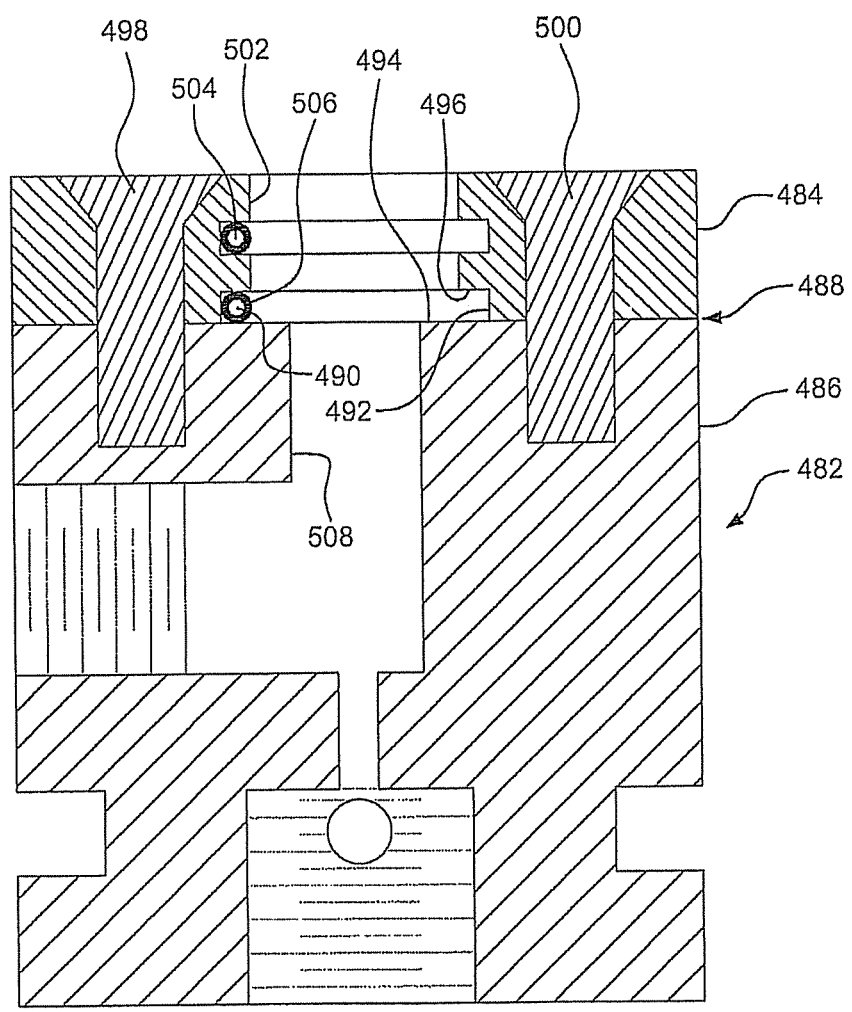
FIG. 13 is an alternative construction for a vessel holder useful with any embodiment of the invention, for example those of the other Figures.
Figure 14:
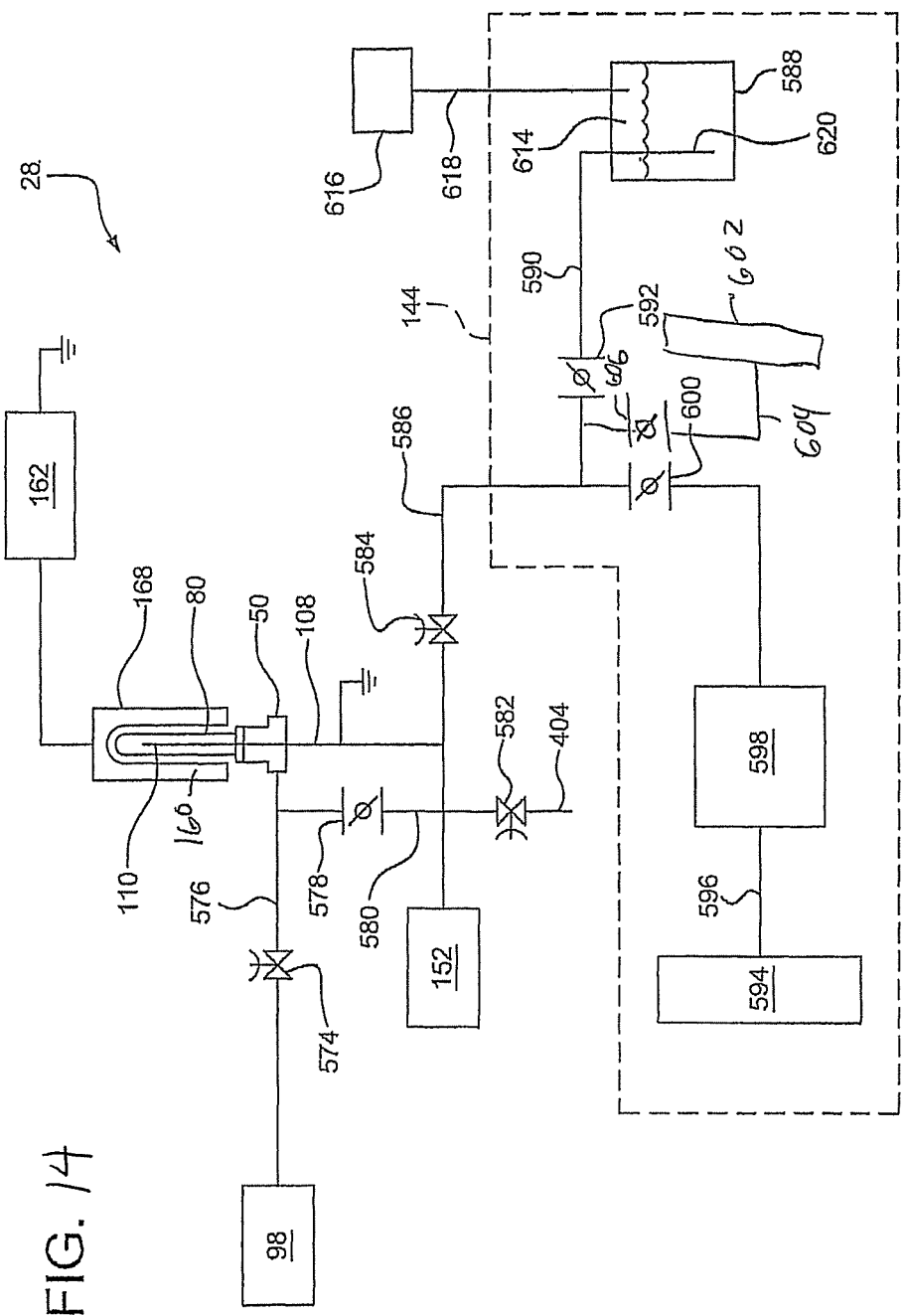
FIG. 14 is a schematic view of an assembly for treating vessels. The assembly is usable with the apparatus in any of the preceding figures.
Figure 15:
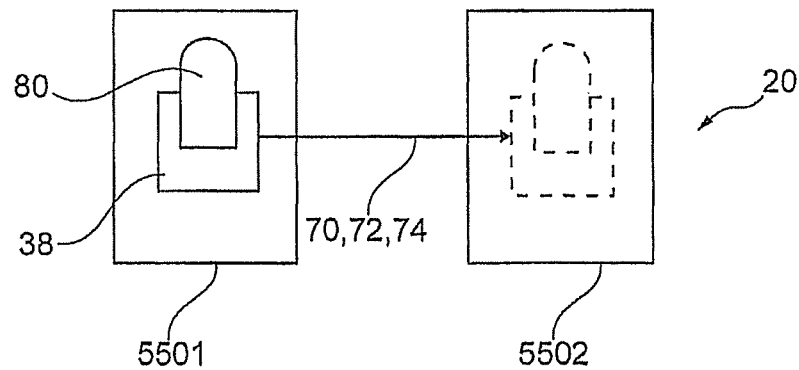
FIG. 15 shows a schematic representation of a vessel processing system according to an exemplary embodiment of the present invention.
Figure 16:
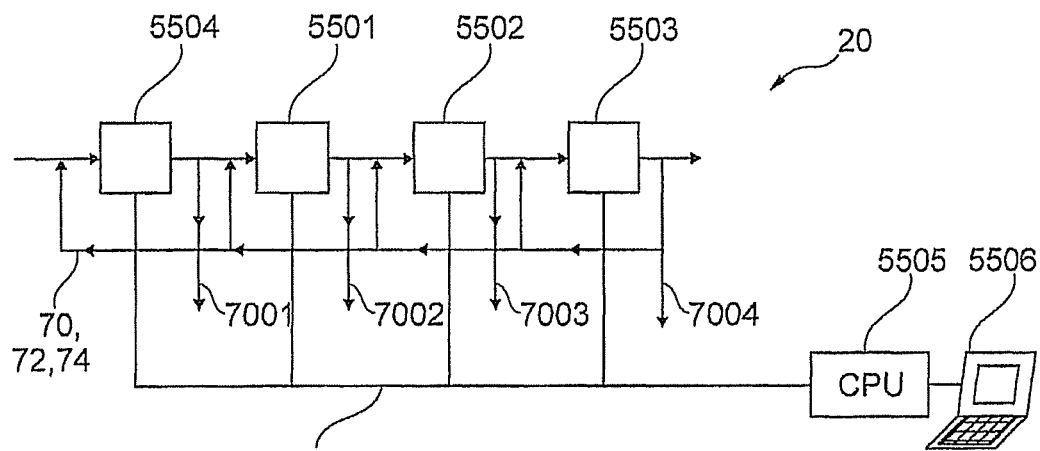
FIG. 16 shows a schematic representation of a vessel processing system according to another exemplary embodiment of the present invention.
Figure 17:
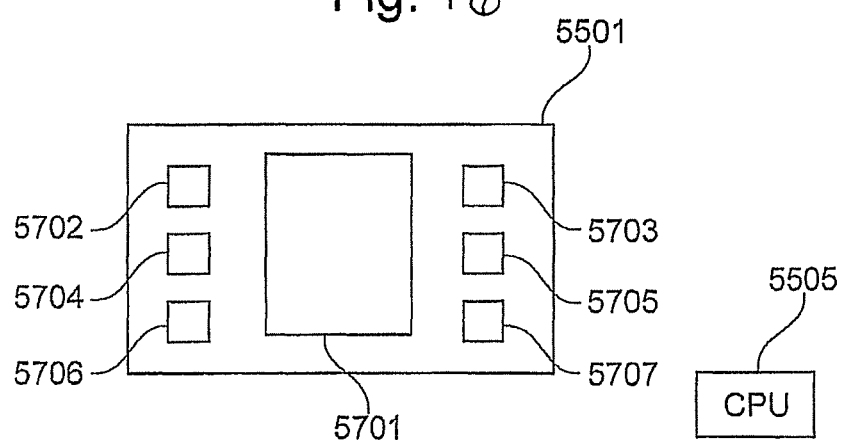
FIG. 17 shows a processing station of a vessel processing system according to an exemplary embodiment of the present invention.
Figure 18:
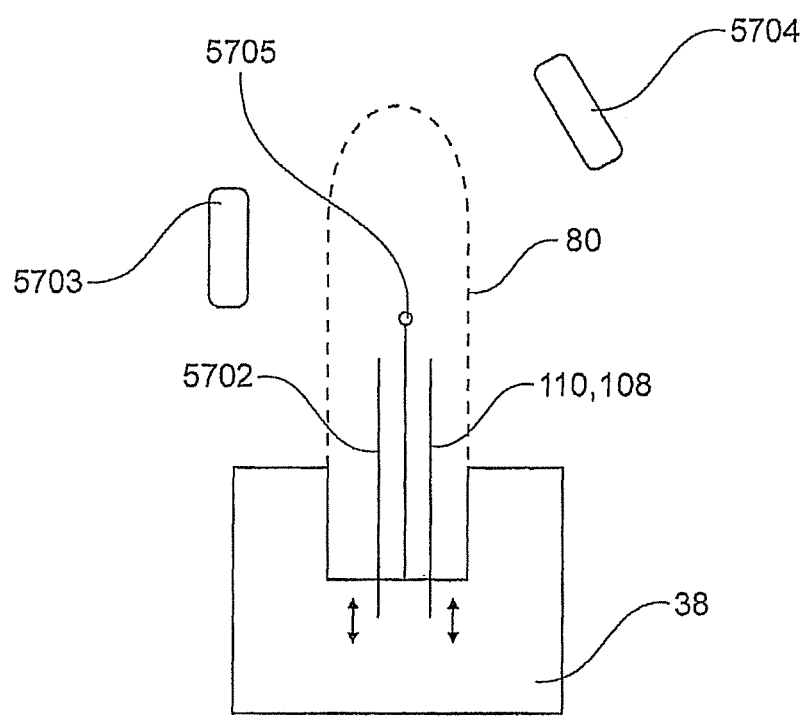
FIG. 18 shows a portable vessel holder according to an exemplary embodiment of the present invention.

Still another embodiment is a chemical vapor deposition apparatus such as the apparatus 28 illustrated in FIG. 14 (or any other illustrated coating apparatus, such as the apparatus illustrated in FIG. 1, 2, 7, 13, or 15-18), for applying a coating to a substrate. Referring now to FIG. 53, the chemical vapor deposition apparatus includes a source of an organosilicon precursor such as the reservoir 588, a source of a carrier gas such as 602, and a source of an oxidizing agent such as 594. The chemical vapor deposition apparatus still further includes one or more conduits, such as the conduits 108, 586, 590, 604, and 596, for conveying to the substrate a gaseous reactant or process gas comprising from 1 to 6 standard volumes of the precursor, from 5 to 100 standard volumes of the carrier gas, and from 0.1 to 2 standard volumes of the oxidizing agent. The chemical vapor deposition apparatus further includes a source 162 of microwave or radio frequency energy and an applicator or electrode such as 160 powered by the source of microwave or radio frequency energy for generating plasma in the gaseous reactant or process gas.

Yet another embodiment is a syringe such as 252 comprising a plunger 258, a barrel 250, and a coating on the interior surface 264. The barrel 250 is a vessel and has an interior surface 264 defining the vessel lumen 274 and receiving the plunger 258 for sliding. The vessel interior surface 264 is a substrate. The coating is a lubricity layer on the substrate 264, the plunger 258, or both, applied by chemical vapor deposition, employing as the gaseous reactant or process gas from 1 to 6 standard volumes of an organosilicon precursor, from 5 to 100 standard volumes of a carrier gas, and from 0.1 to 2 standard volumes of an oxidizing agent.

Even another embodiment is a plunger 258 for a syringe 252, comprising a piston or tip, a coating, and a push rod. The piston or tip has a front face, a generally cylindrical side face that slides within the barrel 250, comprising a substrate, and a back portion. The side face is configured to movably seat within a syringe barrel. The coating is on the substrate and is a lubricity layer interfacing with the side face. The lubricity layer is produced from a chemical vapor deposition (CVD) process employing the previously defined gaseous reactant or process gas. The push rod engages the back portion of the piston and is configured for advancing the piston in a syringe barrel.

Figure 5:
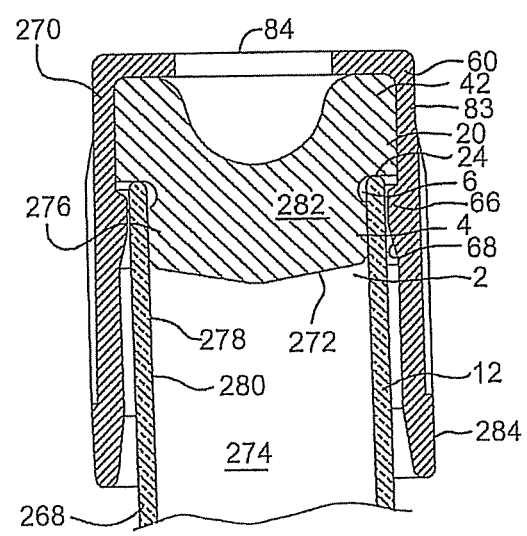
FIG. 5 is a fragmentary section of the blood collection tube and closure assembly of FIG. 4.

Another embodiment is a stopper such as 282 (FIGS. 5-6). The stopper 282 includes a sliding surface 276 defining a substrate and adapted to be received in an opening to be stopped. The substrate has on it a lubricity coating 288 made by providing a precursor comprising an organosilicon compound and applying the precursor to at least a portion of the sliding surface by chemical vapor deposition, employing a gaseous reactant or process gas as defined above.

Even another embodiment is a medical or diagnostic kit including a vessel having a coating as defined in any embodiment above on a substrate as defined in any embodiment above. Optionally, the kit additionally includes a medicament or diagnostic agent which is contained in the coated vessel in contact with the coating; and/or a hypodermic needle, double-ended needle, or other delivery conduit; and/or an instruction sheet.

Other aspects of the invention include any one or more of the following:

use of the coating according to any embodiment described above for coating a surface and thereby preventing or reducing mechanical and/or chemical effects of the surface on a compound or composition in contact with the coating;

use of the coating according to any described embodiment as a lubricity layer;

use of the coating according to any described embodiment for protecting a compound or composition contacting the coating against mechanical and/or chemical effects of the surface of the uncoated vessel material;

use of the coating according to any described embodiment for preventing or reducing precipitation and/or clotting or platelet activation of a compound or a component of the composition in contact with the coating.

As one option, the compound or a component of the composition is insulin, and precipitation of the insulin is prevented or reduced. As another option, the compound or a component of the composition is blood or a blood fraction, and blood clotting or platelet activation is prevented or reduced. As still another option, the coated vessel is a blood collection tube. Optionally, the blood collection tube can contain an agent for preventing blood clotting or platelet activation, for example ethylenediaminetetraacetic acid (EDTA), a sodium salt thereof, or heparin.

Additional options for use of the invention include any one or more of the following:

use of a coated substrate according to any described embodiment, for example a vessel such as a sample collection tube, for example a blood collection tube and/or a closed-ended sample collection tube; a vial; a conduit; a cuvette; or a vessel part, for example a stopper; or a syringe, or a syringe part, for example a barrel or piston, for reception and/or storage and/or delivery of a compound or composition.

The use of a coated substrate according to any described embodiment is contemplated for storing insulin.

The use of a coated substrate according to any described embodiment is contemplated for storing blood. Optionally, the stored blood is viable for return to the vascular system of a patient.

Use of a coating according to any described embodiment is contemplated as (i) a lubricity layer having a lower frictional resistance than the uncoated surface; and/or (ii) a hydrophobic layer that is more hydrophobic than the uncoated surface.

Other aspects of the invention include any of the uses defined above in the summary section.

The following is a more detailed description of the invention.

II. Vessel Holders

II.A. The portable vessel holders 38, 50, and 482 are provided for holding and conveying a vessel having an opening while the vessel is processed. The vessel holder includes a vessel port, a second port, a duct, and a conveyable housing.

II.A. The vessel port is configured to seat a vessel opening in a mutually communicating relation. The second port is configured to receive an outside gas supply or vent. The duct is configured for passing one or more gases between a vessel opening seated on the vessel port and the second port. The vessel port, second port, and duct are attached in substantially rigid relation to the conveyable housing. Optionally, the portable vessel holder weighs less than five pounds. An advantage of a lightweight vessel holder is that it can more readily be transported from one processing station to another.

II.A. In certain embodiments of the vessel holder the duct more specifically is a vacuum duct and the second port more specifically is a vacuum port. The vacuum duct is configured for withdrawing a gas via the vessel port from a vessel seated on the vessel port. The vacuum port is configured for communicating between the vacuum duct and an outside source of vacuum. The vessel port, vacuum duct, and vacuum port can be attached in substantially rigid relation to the conveyable housing.

II.A. The vessel holders are shown, for example, in FIG. 1. The vessel holder 50 has a vessel port 82 configured to receive and seat the opening of a vessel 80. The interior surface of a seated vessel 80 can be processed via the vessel port 82. The vessel holder 50 can include a duct, for example a vacuum duct 94, for withdrawing a gas from a vessel 80 seated on the vessel port 92. The vessel holder can include a second port, for example a vacuum port 96 communicating between the vacuum duct 94 and an outside source of vacuum, such as the vacuum pump 98. The vessel port 92 and vacuum port 96 can have sealing elements, for example O-ring butt seals, respectively 100 and 102, or side seals between an inner or outer cylindrical wall of the vessel port 82 and an inner or outer cylindrical wall of the vessel 80 to receive and form a seal with the vessel 80 or outside source of vacuum 98 while allowing communication through the port. Gaskets or other sealing arrangements can or also be used.

II.A. The vessel holder such as 50 can be made of any material, for example thermoplastic material and/or electrically nonconductive material. Or, the vessel holder such as 50 can be made partially, or even primarily, of electrically conductive material and faced with electrically nonconductive material, for example in the passages defined by the vessel port 92, vacuum duct 94, and vacuum port 96. Examples of suitable materials for the vessel holder 50 are: a polyacetal, for example Delrin® acetal material sold by E. I. du Pont De Nemours and Company, Wilmington Del.; polytetrafluoroethylene (PTFE), for example Teflon® PTFE sold by E. I. du Pont De Nemours and Company, Wilmington Del.; Ultra-High-Molecular-Weight Polyethylene (UHMWPE); High density Polyethylene (HDPE); or other materials known in the art or newly discovered.

II.A. FIG. 1 also illustrates that the vessel holder, for example 50, can have a collar 116 for centering the vessel 80 when it is approaching or seated on the port 92.

FIG. 13 is an alternative construction for a vessel holder 482 usable, for example, with the embodiments of any other Figure. The vessel holder 482 comprises an upper portion 484 and a base 486 joined together at a joint 488. A sealing element, for example an O-ring 490 (the right side of which is cut away to allow the pocket retaining it to be described) is captured between the upper portion 484 and the base 486 at the joint 488. In the illustrated embodiment, the O-ring 490 is received in an annular pocket 492 to locate the O-ring when the upper portion 484 is joined to the base 486.

Figure 11:
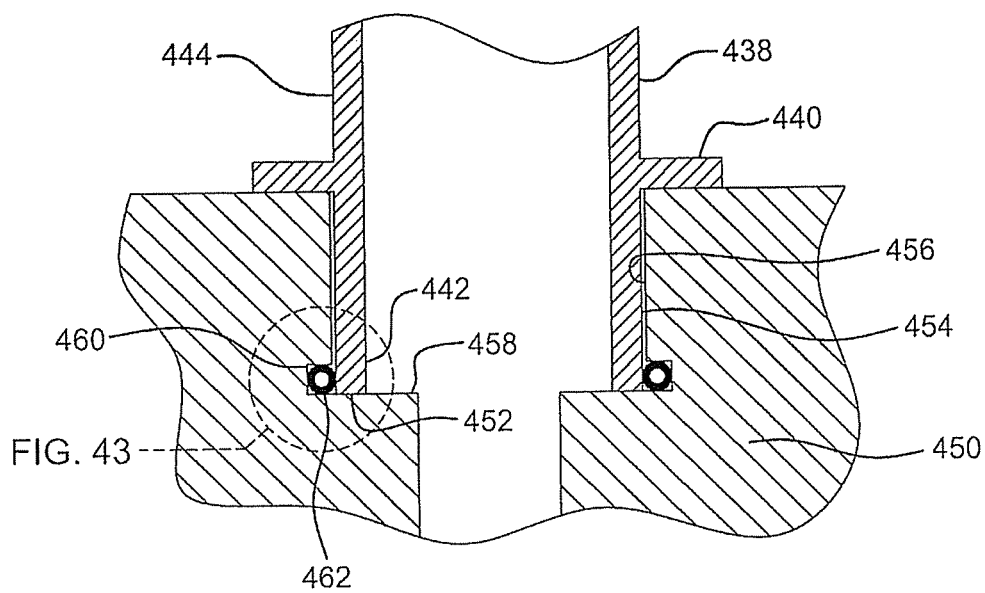
FIG. 11 is a fragmentary detail longitudinal section of an alternative sealing arrangement, usable for example, with the embodiments of FIGS. 1, 2, and 9, for seating a vessel on a vessel holder.

II.B. In this embodiment, the O-ring 490 is captured and bears against a radially extending abutment surface 494 and the radially extending wall 496 partially defining the pocket 492 when the upper portion 484 and the base 486 are joined, in this case by the screws 498 and 500. The O-ring 490 thus seats between the upper portion 484 and base 486. The O-ring 490 captured between the upper portion 484 and the base 486 also receives the vessel 80 (removed in this figure for clarity of illustration of other features) and forms a first O-ring seal of the vessel port 502 about the vessel 80 opening, analogous to the O-ring seal arrangement about the vessel back opening 442 in FIG. 11.

Figure 12:
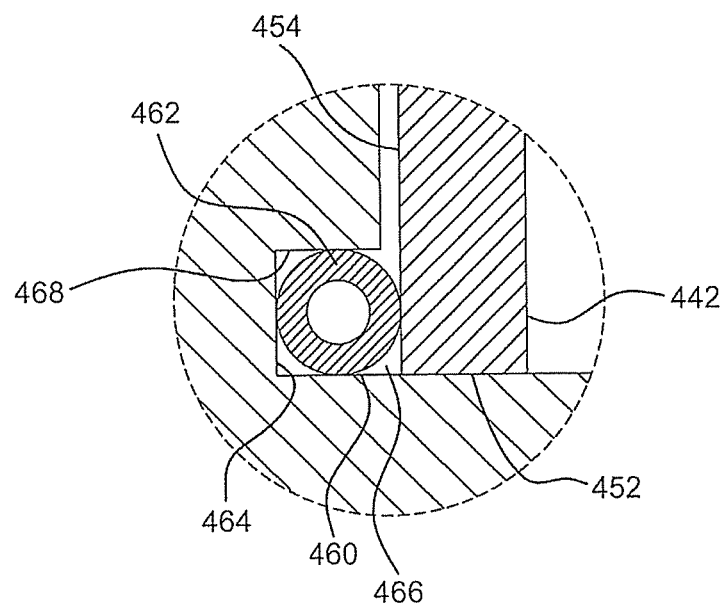
FIG. 12 is a further enlarged detail view of the sealing arrangement shown in FIG. 11.

II.B. In this embodiment, though not a requirement, the vessel port 502 has both the first O-ring 490 seal and a second axially spaced O-ring 504 seal, each having an inner diameter such as 506 sized to receive the outer diameter (analogous to the sidewall 454 in FIG. 12) of a vessel such as 80 for sealing between the vessel port 502 and a vessel such as 80. The spacing between the O-rings 490 and 504 provides support for a vessel such as 80 at two axially spaced points, preventing the vessel such as 80 from being skewed with respect to the O-rings 490 and 504 or the vessel port 502. In this embodiment, though not a requirement, the radially extending abutment surface 494 is located proximal of the O-ring 490 and 506 seals and surrounding the vacuum duct 508.

III. Processing Vessels Seated on Vessel Holders

III.A. FIG. 1 shows a method for processing a vessel 80. The method can be carried out as follows.

III.A. A vessel 80 can be provided having an opening 82 and a wall 86 defining an interior surface 88. As one embodiment, the vessel 80 can be formed in and then removed from a mold such as 22. Optionally within 60 seconds, or within 30 seconds, or within 25 seconds, or within 20 seconds, or within 15 seconds, or within 10 seconds, or within 5 seconds, or within 3 seconds, or within 1 second after removing the vessel from the mold, or as soon as the vessel 80 can be moved without distorting it during processing (assuming that it is made at an elevated temperature, from which it progressively cools), the vessel opening 82 can be seated on the vessel port 92. Quickly moving the vessel 80 from the mold 22 to the vessel port 92 reduces the dust or other impurities that can reach the surface 88 and occlude or prevent adhesion of the barrier or other type of coating 90. Also, the sooner a vacuum is drawn on the vessel 80 after it is made, the less chance any particulate impurities have of adhering to the interior surface 88.

III.A. A vessel holder such as 50 comprising a vessel port 92 can be provided. The opening 82 of the vessel 80 can be seated on the vessel port 92. Before, during, or after seating the opening 82 of the vessel 80 on the vessel port 92, the vessel holder such as 40 (for example in FIG. 6) can be transported into engagement with one or more of the bearing surfaces 220-240 to position the vessel holder 40 with respect to the processing device or station such as 24.

III.A. The interior surface 88 of the seated vessel 80 can be then processed via the vessel port 92 at the first processing station, which can be, as one example, the barrier application or other type of coating station 28 shown in FIG. 1. The vessel holder 50 and seated vessel 80 are transported from the first processing station 28 to the second processing station, for example the processing station 32. The interior surface 88 of the seated vessel 80 can be processed via the vessel port 92 at the second processing station such as 32.

III.A. Any of the above methods can include the further step of removing the vessel 80 from the vessel holder such as 66 following processing the interior surface 88 of the seated vessel 80 at the second processing station or device.

III.A. Any of the above methods can include the further step, after the removing step, of providing a second vessel 80 having an opening 82 and a wall 86 defining an interior surface 88. The opening 82 of the second vessel such as 80 can be seated on the vessel port 92 of another vessel holder such as 38. The interior surface of the seated second vessel 80 can be processed via the vessel port 92 at the first processing station or device such as 24. The vessel holder such as 38 and seated second vessel 80 can be transported from the first processing station or device 24 to the second processing station or device such as 26. The seated second vessel 80 can be processed via the vessel port 92 by the second processing station or device 26.

IV. PECVD Apparatus for Making Vessels

IV.A. PECVD Apparatus Including Vessel Holder, Internal Electrode, Vessel as Reaction Chamber IV.A. Another embodiment is a PECVD apparatus including a vessel holder, an inner electrode, an outer electrode, and a power supply. A vessel seated on the vessel holder defines a plasma reaction chamber, which optionally can be a vacuum chamber. Optionally, a source of vacuum, a reactant gas source, a gas feed or a combination of two or more of these can be supplied. Optionally, a gas drain, not necessarily including a source of vacuum, is provided to transfer gas to or from the interior of a vessel seated on the port to define a closed chamber.

IV.A. The PECVD apparatus can be used for atmospheric-pressure PECVD, in which case the plasma reaction chamber does not need to function as a vacuum chamber.

IV.A. In the embodiment illustrated in FIG. 1, the vessel holder 50 comprises a gas inlet port 104 for conveying a gas into a vessel seated on the vessel port. The gas inlet port 104 has a sliding seal provided by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted deep into the vessel 80 for providing one or more PECVD reactants and other gaseous reactant or process gases.

IV.A. FIG. 14 shows additional optional details of the coating station 28 that are usable, for example, with all the illustrated embodiments. The coating station 28 can also have a main vacuum valve 574 in its vacuum line 576 leading to the pressure sensor 152. A manual bypass valve 578 is provided in the bypass line 580. A vent valve 582 controls flow at the vent 404.

IV.A. Flow out of the PECVD gas or precursor source 144 is controlled by a main reactant gas valve 584 regulating flow through the main reactant feed line 586. One component of the gas source 144 is the organosilicon liquid reservoir 588. The contents of the reservoir 588 are drawn through the organosilicon capillary line 590, which is provided at a suitable length to provide the desired flow rate. Flow of organosilicon vapor is controlled by the organosilicon shut-off valve 592. Pressure is applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 is sealed and the capillary connection 620 is at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. Oxygen is provided from the oxygen tank 594 via an oxygen feed line 596 controlled by a mass flow controller 598 and provided with an oxygen shut-off valve 600.

IV.A. Referring especially to FIG. 1, the processing station 28 can include an electrode 160 fed by a radio frequency power supply 162 for providing an electric field for generating plasma within the vessel 80 during processing. In this embodiment, the probe 108 is also electrically conductive and is grounded, thus providing a counter-electrode within the vessel 80. Alternatively, in any embodiment the outer electrode 160 can be grounded and the probe 108 directly connected to the power supply 162.

Figure 2:
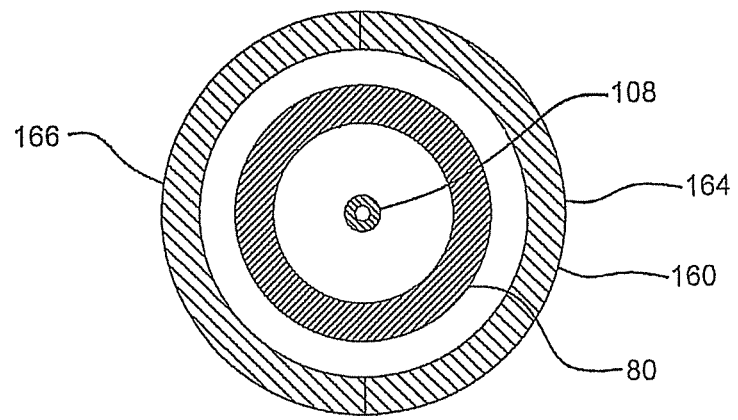
FIG. 2 is a section taken along section lines A-A of FIG. 1.
Figure 8:
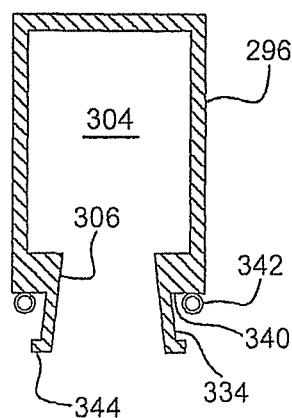
FIG. 8 is an enlarged detail view of the processing vessel of FIG. 7.
Figure 9:
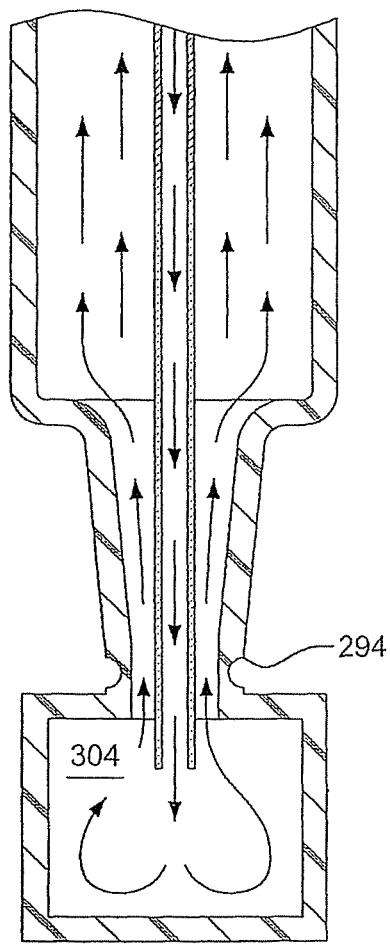
FIG. 9 is a longitudinal section of a combined syringe barrel and gas receiving volume according to another embodiment of the invention.

IV.A. In the embodiment of FIG. 1, the outer electrode 160 can either be generally cylindrical as illustrated in FIGS. 2 and 8 or a generally U-shaped elongated channel. Each illustrated embodiment has one or more sidewalls, such as 164 and 166, and optionally a top end 168, disposed about the vessel 80 in close proximity.

IV.A The electrode 160 shown in FIG. 1 can be shaped like a "U" channel with its length into the page and the puck or vessel holder 50 can move through the activated (powered) electrode during the treatment/coating process. Note that since external and internal electrodes are used, this apparatus can employ a frequency between 50 Hz and 1 GHz applied from a power supply 162 to the U channel electrode 160. The probe 108 can be grounded to complete the electrical circuit, allowing current to flow through the low-pressure gas(es) inside of the vessel 80. The current creates plasma to allow the selective treatment and/or coating of the interior surface 88 of the device.

IV.A The electrode in FIG. 1 can also be powered by a pulsed power supply. Pulsing allows for depletion of reactive gases and then removal of by-products prior to activation and depletion (again) of the reactive gases. Pulsed power systems are typically characterized by their duty cycle which determines the amount of time that the electric field (and therefore the plasma) is present. The power-on time is relative to the power-off time. For example a duty cycle of 10% can correspond to a power on time of 10% of a cycle where the power is off for 90% of the time. As a specific example, the power might be on for 0.1 second and off for 1 second. Pulsed power systems reduce the effective power input for a given power supply 162, since the off-time results in increased processing time. When the system is pulsed, the resulting coating can be very pure (no by-products or contaminants). Another result of pulsed systems is the possibility to achieve atomic layer or coating deposition (ALD). In this case, the duty cycle can be adjusted so that the power-on time results in the deposition of a single layer or coating of a desired material. In this manner, a single atomic layer or coating is contemplated to be deposited in each cycle. This approach can result in highly pure and highly structured coatings (although at the temperatures required for deposition on polymeric surfaces, temperatures optionally are kept low (<100° C.) and the low-temperature coatings can be amorphous).

IV.A. An alternative coating station employs a microwave cavity instead of an outer electrode. The energy applied can be a microwave frequency, for example 2.45 GHz.

V.1 Precursors for PECVD Coating

The precursor for the PECVD coating of the present invention is broadly defined as an organometallic precursor. An organometallic precursor is defined in this specification as comprehending compounds of metal elements from Group III and/or Group IV of the Periodic Table having organic residues, e.g. hydrocarbon, aminocarbon or oxycarbon residues. Organometallic compounds as presently defined include any precursor having organic moieties bonded to silicon or other Group III/IV metal atoms directly, or optionally bonded through oxygen or nitrogen atoms. The relevant elements of Group III of the Periodic Table are Boron, Aluminum, Gallium, Indium, Thallium, Scandium, Yttrium, and Lanthanum, Aluminum and Boron being preferred. The relevant elements of Group IV of the Periodic Table are Silicon, Germanium, Tin, Lead, Titanium, Zirconium, Hafnium, and Thorium, with Silicon and Tin being preferred. Other volatile organic compounds can also be contemplated. However, organosilicon compounds are preferred for performing present invention.

An organosilicon precursor is contemplated, where an "organosilicon precursor" is defined throughout this specification most broadly as a compound having at least one of the linkages:

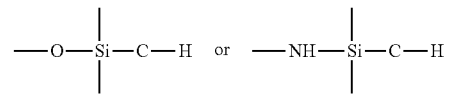

The first structure immediately above is a tetravalent silicon atom connected to an oxygen atom and an organic carbon atom (an organic carbon atom being a carbon atom bonded to at least one hydrogen atom). The second structure immediately above is a tetravalent silicon atom connected to an —NH— linkage and an organic carbon atom (an organic carbon atom being a carbon atom bonded to at least one hydrogen atom). Optionally, the organosilicon precursor is selected from the group consisting of a linear siloxane, a monocyclic siloxane, a polycyclic siloxane, a polysilsesquioxane, a linear silazane, a monocyclic silazane, a polycyclic silazane, a polysilsesquiazane, and a combination of any two or more of these precursors. Also contemplated as a precursor, though not within the two formulas immediately above, is an alkyl trimethoxysilane. If an oxygen-containing precursor (e.g. a siloxane) is used, a representative predicted empirical composition resulting from PECVD under conditions forming a hydrophobic or lubricating coating would be $Si_wO_xC_yH_z$ as defined in the Definition Section, while a representative predicted empirical composition resulting from PECVD under conditions forming a barrier coating would be $SiO_x$, where x in this formula is from about 1.5 to about 2.9. If a nitrogen-containing precursor (e.g. a silazane) is used, the predicted composition would be $Si_{w*}N_{x*}C_{y*}H_{z*}$, i.e. in $Si_wO_xC_yH_z$ as specified in the Definition Section, O is replaced by N and the indices are adapted to the higher valency of N as compared to O (3 instead of 2). The latter adaptation will generally follow the ratio of w, x, y and z in a siloxane to the corresponding indices in its aza counterpart. In a particular aspect of the invention, $Si_{w*}N_{x*}C_{y*}H_{z*}$ in which w*, x*, y*, and z* are defined the same as w, x, y, and z for the siloxane counterparts, but for an optional deviation in the number of hydrogen atoms.

One type of precursor starting material having the above empirical formula is a linear siloxane, for example a material having the following formula:

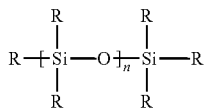

in which each R is independently selected from alkyl, for example methyl, ethyl, propyl, isopropyl, butyl, isobutyl, t-butyl, vinyl, alkyne, or others, and n is 1, 2, 3, 4, or greater, optionally two or greater. Several examples of contemplated linear siloxanes are
  hexamethyldisiloxane (HMDSO),
  octamethyltrisiloxane,
  decamethyltetrasiloxane,
  dodecamethylpentasiloxane,
or combinations of two or more of these. The analogous silazanes in which —NH— is substituted for the oxygen atom in the above structure are also useful for making analogous coatings. Several examples of contemplated linear silazanes are octamethyltrisilazane, decamethyltetrasilazane, or combinations of two or more of these.

V.C. Another type of precursor starting material is a monocyclic siloxane, for example a material having the following structural formula:

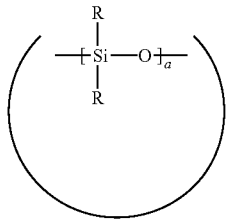

in which R is defined as for the linear structure and "a" is from 3 to about 10, or the analogous monocyclic silazanes. Several examples of contemplated hetero-substituted and unsubstituted monocyclic siloxanes and silazanes include
1,3,5-trimethyl-1,3,5-tris(3,3,3-trifluoropropyl)methyl]cyclotrisiloxane
2,4,6,8-tetramethyl-2,4,6,8-tetravinylcyclotetrasiloxane,
pentamethylcyclopentasiloxane,
pentavinylpentamethylcyclopentasiloxane,
hexamethylcyclotrisiloxane,
hexaphenylcyclotrisiloxane,
octamethylcyclotetrasiloxane (OMCTS),
octaphenylcyclotetrasiloxane,
decamethylcyclopentasiloxane
dodecamethylcyclohexasiloxane,
methyl(3,3,3-trifluoropropyl)cyclosiloxane,
Cyclic organosilazanes are also contemplated, such as
Octamethylcyclotetrasilazane,
1,3,5,7-tetravinyl-1,3,5,7-tetramethylcyclotetrasilazane
  hexamethylcyclotrisilazane,
octamethylcyclotetrasilazane,
decamethylcyclopentasilazane,
dodecamethylcyclohexasilazane, or
combinations of any two or more of these.

V.C. Another type of precursor starting material is a polycyclic siloxane, for example a material having one of the following structural formulas:

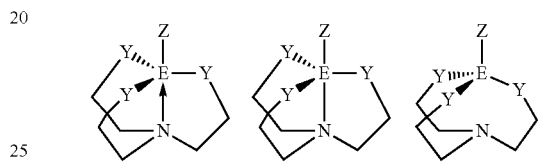

in which Y can be oxygen or nitrogen, E is silicon, and Z is a hydrogen atom or an organic substituent, for example alkyl such as methyl, ethyl, propyl, isopropyl, butyl, isobutyl, t-butyl, vinyl, alkyne, or others. When each Y is oxygen, the respective structures, from left to right, are a silatrane, a silquasilatrane, and a silproatrane. When Y is nitrogen, the respective structures are an azasilatrane, an azasilquasiatrane, and an azasilproatrane.

V.C. Another type of polycyclic siloxane precursor starting material is a polysilsesquioxane, with the empirical formula $RSiO_{1.5}$ and the structural formula:

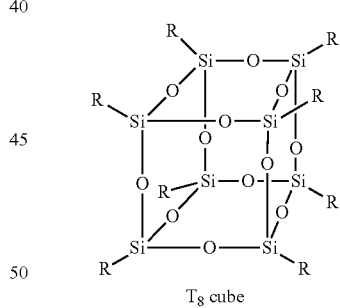

$T_8$ cube in which each R is a hydrogen atom or an organic substituent, for example alkyl such as methyl, ethyl, propyl, isopropyl, butyl, isobutyl, t-butyl, vinyl, alkyne, or others. Two commercial materials of this sort are SST-eM01 poly(methylsilsesquioxane), in which each R is methyl, and SST-3MH1.1 poly(Methyl-Hydridosilsesquioxane), in which 90% of the R groups are methyl, 10% are hydrogen atoms. This material is available in a 10% solution in tetrahydrofuran, for example. Combinations of two or more of these are also contemplated. Other examples of a contemplated precursor are methylsilatrane, CAS No. 2288-13-3, in which each Y is oxygen and Z is methyl, methylazasilatrane, SST-eM01 poly(methylsilsesquioxane), in which each R optionally can be methyl, SST-3MH1.1 poly(Methyl-Hydridosilsesquioxane), in which 90% of the R groups are methyl and 10% are hydrogen atoms, or a combination of any two or more of these.

V.C. The analogous polysilsesquiazanes in which —NH— is substituted for the oxygen atom in the above structure are also useful for making analogous coatings. Examples of contemplated polysilsesquiazanes are a poly (methylsilsesquiazane), in which each R is methyl, and a poly(Methyl-Hydridosilsesquiazane, in which 90% of the R groups are methyl, 10% are hydrogen atoms. Combinations of two or more of these are also contemplated.

V.C. One particularly contemplated precursor for the lubricity layer or coating according to the present invention is a monocyclic siloxane, for example is octamethylcyclotetrasiloxane.

One particularly contemplated precursor for the hydrophobic layer or coating according to the present invention is a monocyclic siloxane, for example is octamethylcyclotetrasiloxane.

One particularly contemplated precursor for the barrier coating according to the present invention is a linear siloxane, for example is HMDSO.

V.C. In any of the coating methods according to the present invention, the applying step optionally can be carried out by vaporizing the precursor and providing it in the vicinity of the substrate. E.g., OMCTS is usually vaporized by heating it to about 50° C. before applying it to the PECVD apparatus.

V.2 General PECVD Method

In the context of the present invention, the following PECVD method is generally applied, which contains the following steps:
(a) providing a process gas comprising a precursor as defined herein, an oxidizing gas, a carrier gas, and optionally a hydrocarbon; and
(b) generating a plasma from the process gas, thus forming a coating on the substrate surface by plasma enhanced chemical vapor deposition (PECVD).

The plasma coating technology used herein is based on Plasma Enhanced Chemical Vapor Deposition (PECVD). Methods and apparatus suitable to perform said PECVD coatings are described in EP10162755.2 filed May 12, 2010; EP10162760.2 filed May 12, 2010; EP10162756.0 filed May 12, 2010; EP10162758.6 filed May 12, 2010; EP10162761.0 filed May 12, 2010; and EP10162757.8 filed May 12, 2010. The PECVD methods and apparatus as described therein are suitable to perform the present invention and are therefore incorporated herein by reference.

An exemplary preferred embodiment of the PECVD technology will be described in the following sections.

The process utilizes a silicon containing vapor that can be combined with oxygen at reduced pressures (mTorr range—atmospheric pressure is 760 Torr) inside a container.

An electrical field generated at, e.g., 13.56 MHz [radio frequency range] is then applied between an external electrode and an internal grounded gas inlet to create a plasma. At the pressures and powers that are used to coat a container, the plasma process is driven by electron impact ionization, which means the electrons in the process are the driving force behind the chemistry. Specifically, the plasma drives the chemical reaction through electron impact ionization of the silicon containing material [e.g., hexamethyldisiloxane (HMDSO) or other reactants like octamethylcyclotetrasiloxane (OMCTS)] resulting in a silicon dioxide or $SiO_xC_yH_z$ coating deposited onto the interior surfaces of the container. These coatings are in a typical embodiment on the order of 20 or more nanometers in thickness. HMDSO consists of an Si—O—Si backbone with six (6) methyl groups attached to the silicon atoms. The process breaks the Si—C bonds and (at the surface of the tube or syringe) reacts with oxygen to create silicon dioxide. Since the coating is grown on an atomic basis, dense, conformal coatings with thicknesses of 20-30 nanometers can achieve significant barrier properties. The silicon oxide acts as a physical barrier to gases, moisture, and small organic molecules, and is of greater purity than commercial glasses. OMCTS results in coatings with lubricity or anti-adhesion properties.

The technology is unique in several aspects:

(a) The process utilizes the rigid container as the vacuum chamber. PECVD conventionally uses a secondary vacuum vessel into which the part(s) are loaded and coated. Utilizing the container as a vacuum chamber significantly simplifies the process apparatus and reduces cycle/processing time, and thus manufacturing cost and capital. This approach also reduces scale-up issues since scale-up is as simple as replicating the number of tubes or syringes required to meet the throughput requirements.

(b) Radio Frequency excitation of the plasma allows energy to be imparted to the ionized gas with little heating of the part. Unlike microwave excitation energies, typically used in PECVD, which will impart significant energy to water molecules in the part itself, radio frequency will not preferentially heat the polymeric tubes or syringes. Controlled heat absorption is critical to prevent substrate temperature increases approaching plastic glass transition temperatures, causing loss of dimensional integrity (collapse under vacuum).

(c) Single layer gas barrier coating—the new technology can generate a single layer of silicon dioxide directly on the interior surface of the part. Most other barrier technologies (thin film) require at least two layers.

(d) Combination barrier-lubricity coatings—the new technology utilizes a combination silicon dioxide/$SiO_xC_yH_z$ coating to provide multiple performance attributes (barrier/lubricity).

The plasma deposition technology in a preferred aspect utilizes a simple manufacturing configuration. The system is based on a "puck," which is used in transportation of tubes and syringes in and out of the coating station. The device-puck interface (see FIG. 6) is critical, since once coating/characterization conditions are established at the pilot scale, there are no scaling issues when moving to full scale production; one simply increases the number of pucks through the same process. The puck is manufactured from a polymeric material (e.g. Delrin™) to provide an electrically insulated base. The container (e.g. a tube as in FIG. 6) is mounted into the puck with the largest opening sealing against an o-ring (mounted in the puck itself). The o-ring provides the vacuum seal between the part and the puck so that the ambient air (principally nitrogen and oxygen with some water vapor) can be removed (pressure reduced) and the process gases introduced. The puck has several key features in addition to the o-ring seal. The puck provides a means of connection to the vacuum pump (which pumps away the atmospheric gases and the by-products of the silicon dioxide reaction), a means of accurately aligning the gas inlet in the part, and a means of providing a vacuum seal between the puck and gas inlet.

For SiO2 deposition, HMDSO and oxygen gases are then admitted into the container through the grounded gas inlet which extends up into the part. At this point, the puck and container are moved into the electrode area. The electrode is constructed from a conductive material (for example copper) and provides a tunnel through which the part passes. The electrode does not make physical contact with the container or the puck and is supported independently. An RF impedance matching network and power supply are connected directly to the electrode. The power supply provides energy (at 13.56 MHz) to the impedance matched network. The RF matching network acts to match the output impedance of the power supply to the complex (capacitive and inductive) impedance of the ionized gases. The matching network delivers maximum power delivery to the ionized gas which ensures deposition of the silicon dioxide coating.

Once the container is coated (as the puck moves the container through the electrode channel—which is stationary), the gases are stopped and atmospheric air (or pure nitrogen) is allowed inside the puck/container to bring it back to atmospheric pressure. At this time, the container can be removed from the puck and moved to the next processing station.

The above describes clearly the means of coating a container having just one opening. Syringes require an additional step before and after loading onto the puck. Since the syringes have openings at both ends (one for connection to a needle and the second for installation of a plunger), the needle end must be sealed prior to coating. The above process allows reaction gases to be admitted into the plastic part interior, an electrical current to pass through the gas inside of the part and a plasma to be established inside the part. The plasma (an ionized composition of the HMDSO or OMCTS and oxygen gases) is what drives the chemistry and the deposition of the plasma coating.

In the method, the coating characteristics are advantageously set by one or more of the following conditions: the plasma properties, the pressure under which the plasma is applied, the power applied to generate the plasma, the presence and relative amount of $O_2$ in the gaseous reactant, the plasma volume, and the organosilicon precursor. Optionally, the coating characteristics are set by the presence and relative amount of $O_2$ in the gaseous reactant and/or the power applied to generate the plasma.

In all embodiments of the present invention, the plasma is in an optional aspect a non-hollow-cathode plasma.

In a further preferred aspect, the plasma is generated at reduced pressure (as compared to the ambient or atmospheric pressure). Optionally, the reduced pressure is less than 300 mTorr, optionally less than 200 mTorr, even optionally less than 100 mTorr.

The PECVD optionally is performed by energizing the gaseous reactant containing the precursor with electrodes powered at a frequency at microwave or radio frequency, and optionally at a radio frequency. The radio frequency preferred to perform an embodiment of the invention will also be addressed as "RF frequency". A typical radio frequency range for performing the present invention is a frequency of from 10 kHz to less than 300 MHz, optionally from 1 to 50 MHz, even optionally from 10 to 15 MHz. A frequency of 13.56 MHz is most preferred, this being a government sanctioned frequency for conducting PECVD work.

There are several advantages for using a RF power source versus a microwave source: Since RF operates a lower power, there is less heating of the substrate/vessel. Because the focus of the present invention is putting a plasma coating on plastic substrates, lower processing temperature are desired to prevent melting/distortion of the substrate. To prevent substrate overheating when using microwave PECVD, the microwave PECVD is applied in short bursts, by pulsing the power. The power pulsing extends the cycle time for the coating, which is undesired in the present invention. The higher frequency microwave can also cause offgassing of volatile substances like residual water, oligomers and other materials in the plastic substrate. This offgassing can interfere with the PECVD coating. A major concern with using microwave for PECVD is delamination of the coating from the substrate. Delamination occurs because the microwaves change the surface of the substrate prior to depositing the coating layer. To mitigate the possibility of delamination, interface coating layers have been developed for microwave PECVD to achieve good bonding between the coating and the substrate. No such interface coating layer or coating is needed with RF PECVD as there is no risk of delamination. Finally, the lubricity layer or coating and hydrophobic layer or coating according to the present invention are advantageously applied using lower power. RF power operates at lower power and provides more control over the PECVD process than microwave power. Nonetheless, microwave power, though less preferred, is usable under suitable process conditions.

Furthermore, for all PECVD methods described herein, there is a specific correlation between the power (in Watts) used to generate the plasma and the volume of the lumen wherein the plasma is generated. Typically, the lumen is the lumen of a vessel coated according to the present invention. The RF power should scale with the volume of the vessel if the same electrode system is employed. Once the composition of a gaseous reactant, for example the ratio of the precursor to $O_2$, and all other parameters of the PECVD coating method but the power have been set, they will typically not change when the geometry of a vessel is maintained and only its volume is varied. In this case, the power will be directly proportional to the volume. Thus, starting from the power to volume ratios provided by present description, the power which has to be applied in order to achieve the same or a similar coating in a vessel of same geometry, but different size, can easily be found. The influence of the vessel geometry on the power to be applied is illustrated by the results of the Examples for tubes in comparison to the Examples for syringe barrels.

For any coating of the present invention, the plasma is generated with electrodes powered with sufficient power to form a coating on the substrate surface. For a lubricity layer or coating or hydrophobic layer, in the method according to an embodiment of the invention the plasma is optionally generated
  (i) with electrodes supplied with an electric power of from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W; and/or
  (ii) wherein the ratio of the electrode power to the plasma volume is less than 10 W/ml, optionally is from 5 W/ml to 0.1 W/ml, optionally is from 4 W/ml to 0.1 W/ml, optionally from 3 W/ml to 0.2 W/ml. optionally from 2 W/ml to 0.2 W/ml.

For a barrier coating or $SiO_x$ coating, the plasma is optionally generated
  (i) with electrodes supplied with an electric power of from 8 to 500 W, optionally from 20 to 400 W, optionally from 35 to 350 W, even optionally from 44 to 300 W, optionally from 44 to 70 W; and/or
  (ii) the ratio of the electrode power to the plasma volume is equal or more than 5 W/ml, optionally is from 6 W/ml to 150 W/ml, optionally is from 7 W/ml to 100 W/ml, optionally from 7 W/ml to 20 W/ml.

The vessel geometry can also influence the choice of the gas inlet used for the PECVD coating. In a particular aspect, a syringe can be coated with an open tube inlet, and a tube can be coated with a gas inlet having small holes which is extended into the tube.

The power (in Watts) used for PECVD also has an influence on the coating properties. Typically, an increase of the power will increase the barrier properties of the coating, and a decrease of the power will increase the lubricity and hydrophobicity of the coating.

A further parameter determining the coating properties is the ratio of $O_2$ (or another oxidizing agent) to the precursor (e.g. organosilicon precursor) in the gaseous reactant used for generating the plasma. Typically, an increase of the $O_2$ ratio in the gaseous reactant will increase the barrier properties of the coating, and a decrease of the $O_2$ ratio will increase the lubricity and hydrophobicity of the coating.

If a lubricity layer or coating is desired, then $O_2$ is optionally present in a volume-volume ratio to the gaseous reactant of from 0:1 to 5:1, optionally from 0:1 to 1:1, even optionally from 0:1 to 0.5:1 or even from 0:1 to 0.1:1.

If, on the other hand, a barrier or $SiO_x$ coating is desired, then the $O_2$ is optionally present in a volume:volume ratio to the gaseous reactant of from 1:1 to 100:1 in relation to the silicon containing precursor, optionally in a ratio of from 5:1 to 30:1, optionally in a ratio of from 10:1 to 20:1, even optionally in a ratio of 15:1.

V.A. PECVD to Apply $SiO_x$ Barrier Coating, Using Plasma that is Substantially Free of Hollow Cathode Plasma V.A. A specific embodiment is a method of applying a barrier coating of $SiO_x$, defined in this specification (unless otherwise specified in a particular instance) as a coating containing silicon, oxygen, and optionally other elements, in which x, the ratio of oxygen to silicon atoms, is from about 1.5 to about 2.9, or 1.5 to about 2.6, or about 2. These alternative definitions of x apply to any use of the term $SiO_x$ in this specification. The barrier coating is applied to the interior of a vessel, for example a sample collection tube, a syringe barrel, or another type of vessel. The method includes several steps.

V.A. A vessel wall is provided, as is a reaction mixture comprising plasma forming gas, i.e. an organosilicon compound gas, optionally an oxidizing gas, and optionally a hydrocarbon gas.

V.A. Plasma is formed in the reaction mixture that is substantially free of hollow cathode plasma. The vessel wall is contacted with the reaction mixture, and the coating of $SiO_x$ is deposited on at least a portion of the vessel wall.

V.A. In certain embodiments, the generation of a uniform plasma throughout the portion of the vessel to be coated is contemplated, as it has been found in certain instances to generate an $SiO_x$ coating providing a better barrier against oxygen. Uniform plasma means regular plasma that does not include a substantial amount of hollow cathode plasma (which has a higher emission intensity than regular plasma and is manifested as a localized area of higher intensity interrupting the more uniform intensity of the regular plasma).

V.A. The hollow cathode effect is generated by a pair of conductive surfaces opposing each other with the same negative potential with respect to a common anode. If the spacing is made (depending on the pressure and gas type) such that the space charge sheaths overlap, electrons start to oscillate between the reflecting potentials of the opposite wall sheaths leading to multiple collisions as the electrons are accelerated by the potential gradient across the sheath region. The electrons are confined in the space charge sheath overlap which results in very high ionization and high ion density plasmas. This phenomenon is described as the hollow cathode effect. Those skilled in the art are able to vary the processing conditions, such as the power level and the feed rates or pressure of the gases, to form uniform plasma throughout or to form plasma including various degrees of hollow cathode plasma.

V.A. In an alternate method, microwave energy can be used to generate the plasma in a PECVD process. The processing conditions can be different, however, as microwave energy applied to a thermoplastic vessel will excite (vibrate) water molecules. Since there is a small amount of water in all plastic materials, the microwaves will heat the plastic. As the plastic heats, the large driving force created by the vacuum inside of the device relative to atmospheric pressure outside the device will pull free or easily desorb materials to the interior surface 88 where they will either become volatile or will be weakly bound to the surface. The weakly bound materials will then create an interface that can hinder subsequent coatings (deposited from the plasma) from adhering to the plastic interior surface 88 of the device.

V.A. As one way to negate this coating hindering effect, a coating can be deposited at very low power (in the example above 5 to 20 Watts at 2.45 GHz) creating a cap onto which subsequent coatings can adhere. This results in a two-step coating process (and two coating layers). In the example above, the initial gas flows (for the capping layer) can be changed to 2 sccm ("standard cubic centimeters per minute") HMDSO and 20 sccm oxygen with a process power of 5 to 20 Watts for approximately 2-10 seconds. Then the gases can be adjusted to the flows in the example above and the power level increased to 20-50 Watts so that an $SiO_x$ coating, in which x in this formula is from about 1.5 to about 2.9, alternatively from about 1.5 to about 2.6, alternatively about 2, can be deposited. Note that the capping layer or coating might provide little to no functionality in certain embodiments, except to stop materials from migrating to the vessel interior surface 88 during the higher power $SiO_x$ coating deposition. Note also that migration of easily desorbed materials in the device walls typically is not an issue at lower frequencies such as most of the RF range, since the lower frequencies do not excite (vibrate) molecular species.

V.A. As another way to negate the coating hindering effect described above, the vessel 80 can be dried to remove embedded water before applying microwave energy. Desiccation or drying of the vessel 80 can be accomplished, for example, by thermally heating the vessel 80, as by using an electric heater or forced air heating. Desiccation or drying of the vessel 80 also can be accomplished by exposing the interior of the vessel 80, or gas contacting the interior of the vessel 80, to a desiccant. Other expedients for drying the vessel, such as vacuum drying, can also be used. These expedients can be carried out in one or more of the stations or devices illustrated or by a separate station or device.

V.A. Additionally, the coating hindering effect described above can be addressed by selection or processing of the resin from which the vessels 80 are molded to minimize the water content of the resin.

V.B. PECVD Coating Restricted Opening of Vessel (Syringe Capillary)

Figure 7:
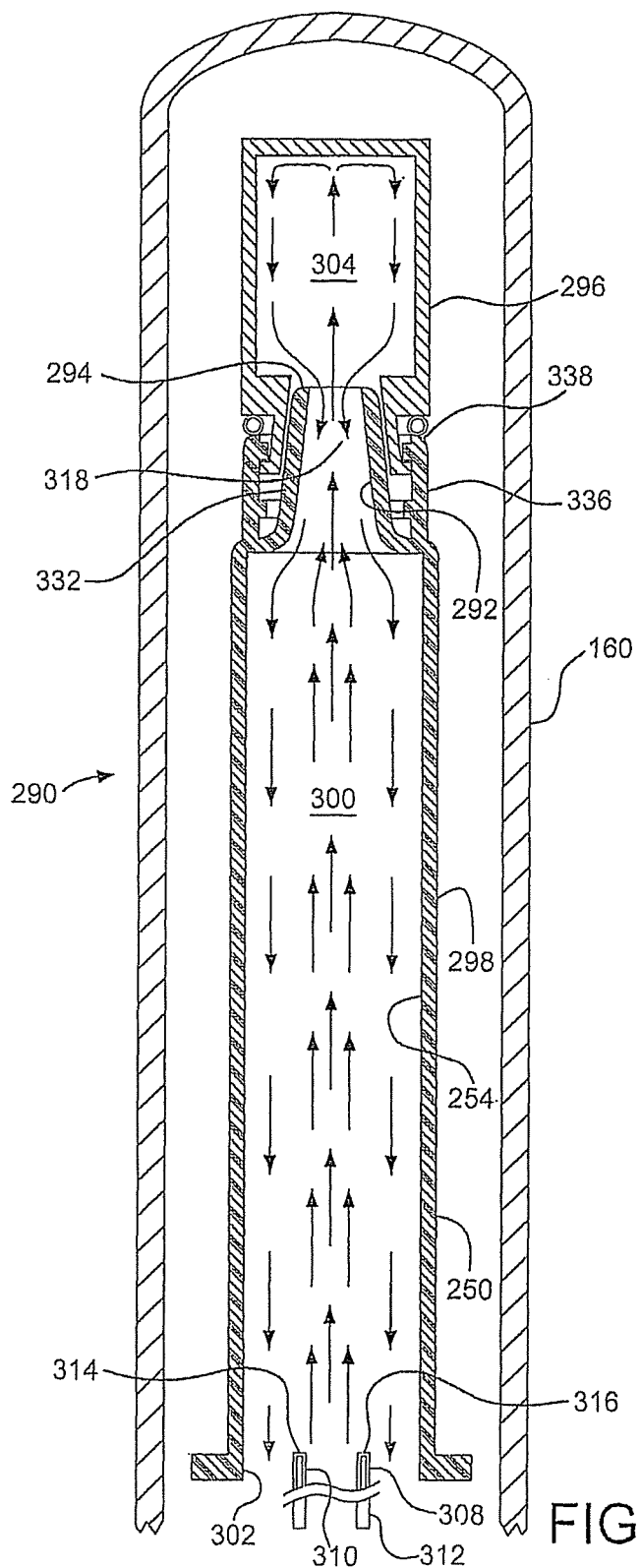
FIG. 7 is a view of another embodiment of the invention for processing syringe barrels and other vessels.

V.B. FIGS. 7 and 8 show a method and apparatus generally indicated at 290 for coating an inner surface 292 of a restricted opening 294 of a generally tubular vessel 250 to be processed, for example the restricted front opening 294 of a syringe barrel 250, by PECVD. The previously described process is modified by connecting the restricted opening 294 to a processing vessel 296 and optionally making certain other modifications.

V.B. The generally tubular vessel 250 to be processed includes an outer surface 298, an inner or interior surface 254 defining a lumen 300, a larger opening 302 having an inner diameter, and a restricted opening 294 that is defined by an inner surface 292 and has an inner diameter smaller than the inner diameter of the larger opening 302.

V.B. The processing vessel 296 has a lumen 304 and a processing vessel opening 306, which optionally is the only opening, although in other embodiments a second opening can be provided that optionally is closed off during processing. The processing vessel opening 306 is connected with the restricted opening 294 of the vessel 250 to be processed to establish communication between the lumen 300 of the vessel 250 to be processed and the processing vessel lumen via the restricted opening 294.

V.B. At least a partial vacuum is drawn within the lumen 300 of the vessel 250 to be processed and lumen 304 of the processing vessel 296. A PECVD reactant is flowed from the gas source 144 (see FIG. 7) through the first opening 302, then through the lumen 300 of the vessel 250 to be processed, then through the restricted opening 294, then into the lumen 304 of the processing vessel 296.

V.B. The PECVD reactant can be introduced through the larger opening 302 of the vessel 250 by providing a generally tubular inner electrode 308 having an interior passage 310, a proximal end 312, a distal end 314, and a distal opening 316, in an alternative embodiment multiple distal openings can be provided adjacent to the distal end 314 and communicating with the interior passage 310. The distal end of the electrode 308 can be placed adjacent to or into the larger opening 302 of the vessel 250 to be processed. A reactant gas can be fed through the distal opening 316 of the electrode 308 into the lumen 300 of the vessel 250 to be processed. The reactant will flow through the restricted opening 294, then into the lumen 304, to the extent the PECVD reactant is provided at a higher pressure than the vacuum initially drawn before introducing the PECVD reactant.

V.B. Plasma 318 is generated adjacent to the restricted opening 294 under conditions effective to deposit a coating of a PECVD reaction product on the inner surface 292 of the restricted opening 294. In the embodiment shown in FIG. 7, the plasma is generated by feeding RF energy to the generally U-shaped outer electrode 160 and grounding the inner electrode 308. The feed and ground connections to the electrodes could also be reversed, though this reversal can introduce complexity if the vessel 250 to be processed, and thus also the inner electrode 308, are moving through the U-shaped outer electrode while the plasma is being generated.

V.B. The plasma 318 generated in the vessel 250 during at least a portion of processing can include hollow cathode plasma generated inside the restricted opening 294 and/or the processing vessel lumen 304. The generation of hollow cathode plasma 318 can contribute to the ability to successfully apply a barrier coating at the restricted opening 294, although the invention is not limited according to the accuracy or applicability of this theory of operation. Thus, in one contemplated mode of operation, the processing can be carried out partially under conditions generating a uniform plasma throughout the vessel 250 and the gas inlet, and partially under conditions generating a hollow cathode plasma, for example adjacent to the restricted opening 294.

V.B. The process is desirably operated under such conditions, as explained here and shown in the drawings, that the plasma 318 extends substantially throughout the syringe lumen 300 and the restricted opening 294. The plasma 318 also desirably extends substantially throughout the syringe lumen 300, the restricted opening 294, and the lumen 304 of the processing vessel 296. This assumes that a uniform coating of the interior 254 of the vessel 250 is desired. In other embodiments non-uniform plasma can be desired.

V.B. It is generally desirable that the plasma 318 have a substantially uniform color throughout the syringe lumen 300 and the restricted opening 294 during processing, and optionally a substantially uniform color substantially throughout the syringe lumen 300, the restricted opening 294, and the lumen 304 of the processing vessel 296. The plasma desirably is substantially stable throughout the syringe lumen 300 and the restricted opening 294, and optionally also throughout the lumen 304 of the processing vessel 296.

V.B. The order of steps in this method is not contemplated to be critical.

V.B. In the embodiment of FIGS. 7 and 8, the restricted opening 294 has a first fitting 332 and the processing vessel opening 306 has a second fitting 334 adapted to seat to the first fitting 332 to establish communication between the lumen 304 of the processing vessel 296 and the lumen 300 of the vessel 250 to be processed.

V.B. In the embodiment of FIGS. 7 and 8, the first and second fittings are male and female Luer lock fittings 332 and 334, respectively integral with the structure defining the restricted opening 294 and the processing vessel opening 306. One of the fittings, in this case the male Luer lock fitting 332, comprises a locking collar 336 with a threaded inner surface and defining an axially facing, generally annular first abutment 338 and the other fitting 334 comprises an axially facing, generally annular second abutment 340 facing the first abutment 338 when the fittings 332 and 334 are engaged.

V.B. In the illustrated embodiment a seal, for example an O-ring 342 can be positioned between the first and second fittings 332 and 334. For example, an annular seal can be engaged between the first and second abutments 338 and 340. The female Luer fitting 334 also includes dogs 344 that engage the threaded inner surface of the locking collar 336 to capture the O-ring 342 between the first and second fittings 332 and 334. Optionally, the communication established between the lumen 300 of the vessel 250 to be processed and the lumen 304 of the processing vessel 296 via the restricted opening 294 is at least substantially leak proof.

V.B. As a further option, either or both of the Luer lock fittings 332 and 334 can be made of electrically conductive material, for example stainless steel. This construction material forming or adjacent to the restricted opening 294 might contribute to formation of the plasma in the restricted opening 294.

V.B. The desirable volume of the lumen 304 of the processing vessel 296 is contemplated to be a trade-off between a small volume that will not divert much of the reactant flow away from the product surfaces desired to be coated and a large volume that will support a generous reactant gas flow rate through the restricted opening 294 before filling the lumen 304 sufficiently to reduce that flow rate to a less desirable value (by reducing the pressure difference across the restricted opening 294). The contemplated volume of the lumen 304, in an embodiment, is less than three times the volume of the lumen 300 of the vessel 250 to be processed, or less than two times the volume of the lumen 300 of the vessel 250 to be processed, or less than the volume of the lumen 300 of the vessel 250 to be processed, or less than 50% of the volume of the lumen 300 of the vessel 250 to be processed, or less than 25% of the volume of the lumen 300 of the vessel 250 to be processed. Other effective relationships of the volumes of the respective lumens are also contemplated.

V.B. The inventors have found that the uniformity of coating can be improved in certain embodiments by repositioning the distal end of the electrode 308 relative to the vessel 250 so it does not penetrate as far into the lumen 300 of the vessel 250 as the position of the inner electrode shown in previous Figures. For example, although in certain embodiments the distal opening 316 can be positioned adjacent to the restricted opening 294, in other embodiments the distal opening 316 can be positioned less than ⅞ the distance, optionally less than ¾ the distance, optionally less than half the distance to the restricted opening 294 from the larger opening 302 of the vessel to be processed while feeding the reactant gas. Or, the distal opening 316 can be positioned less than 40%, less than 30%, less than 20%, less than 15%, less than 10%, less than 8%, less than 6%, less than 4%, less than 2%, or less than 1% of the distance to the restricted opening 294 from the larger opening of the vessel to be processed while feeding the reactant gas.

V.B. Or, the distal end of the electrode 308 can be positioned either slightly inside or outside or flush with the larger opening 302 of the vessel 250 to be processed while communicating with, and feeding the reactant gas to, the interior of the vessel 250. The positioning of the distal opening 316 relative to the vessel 250 to be processed can be optimized for particular dimensions and other conditions of treatment by testing it at various positions. One particular position of the electrode 308 contemplated for treating syringe barrels 250 is with the distal end 314 penetrating about a quarter inch (about 6 mm) into the vessel lumen 300 above the larger opening 302.

V.B. The inventors presently contemplate that it is advantageous to place at least the distal end 314 of the electrode 308 within the vessel 250 so it will function suitably as an electrode, though that is not necessarily a requirement. Surprisingly, the plasma 318 generated in the vessel 250 can be made more uniform, extending through the restricted opening 294 into the processing vessel lumen 304, with less penetration of the electrode 308 into the lumen 300 than has previously been employed. With other arrangements, such as processing a closed-ended vessel, the distal end 314 of the electrode 308 commonly is placed closer to the closed end of the vessel than to its entrance.

V.B. Or, the distal end 314 of the electrode 308 can be positioned at the restricted opening 294 or beyond the restricted opening 294. Various expedients can optionally be provided, such as shaping the processing vessel 296 to improve the gas flow through the restricted opening 294.

V.B. In yet another contemplated embodiment, the inner electrode 308, as in FIG. 7, can be moved during processing, for example, at first extending into the processing vessel lumen 304, then being withdrawn progressively proximally as the process proceeds. This expedient is particularly contemplated if the vessel 250, under the selected processing conditions, is long, and movement of the inner electrode facilitates more uniform treatment of the interior surface 254. Using this expedient, the processing conditions, such as the gas feed rate, the vacuum draw rate, the electrical energy applied to the outer electrode 160, the rate of withdrawing the inner electrode 308, or other factors can be varied as the process proceeds, customizing the process to different parts of a vessel to be treated.

V.B. Conveniently, as in the other processes described in this specification, the larger opening of the generally tubular vessel 250 to be processed can be placed on a vessel support 320, as by seating the larger opening 302 of the vessel 250 to be processed on a port 322 of the vessel support 320. Then the inner electrode 308 can be positioned within the vessel 250 seated on the vessel support 320 before drawing at least a partial vacuum within the lumen 300 of the vessel 250 to be processed.

V.C. Method of Applying a Lubricity Layer

V.C. Another embodiment is a method of applying a lubricity layer or coating derived from an organosilicon precursor. A "lubricity layer" or any similar term is generally defined as a coating that reduces the frictional resistance of the coated surface, relative to the uncoated surface. If the coated object is a syringe (or syringe part, e.g. syringe barrel) or any other item generally containing a plunger or movable part in sliding contact with the coated surface, the frictional resistance has two main aspects—breakout force and plunger sliding force.

The plunger sliding force test is a specialized test of the coefficient of sliding friction of the plunger within a syringe, accounting for the fact that the normal force associated with a coefficient of sliding friction as usually measured on a flat surface is addressed by standardizing the fit between the plunger or other sliding element and the tube or other vessel within which it slides. The parallel force associated with a coefficient of sliding friction as usually measured is comparable to the plunger sliding force measured as described in this specification. Plunger sliding force can be measured, for example, as provided in the ISO 7886-1:1993 test.

The plunger sliding force test can also be adapted to measure other types of frictional resistance, for example the friction retaining a stopper within a tube, by suitable variations on the apparatus and procedure. In one embodiment, the plunger can be replaced by a closure and the withdrawing force to remove or insert the closure can be measured as the counterpart of plunger sliding force.

Also or instead of the plunger sliding force, the breakout force can be measured. The breakout force is the force required to start a stationary plunger moving within a syringe barrel, or the comparable force required to unseat a seated, stationary closure and begin its movement. The breakout force is measured by applying a force to the plunger that starts at zero or a low value and increases until the plunger begins moving. The breakout force tends to increase with storage of a syringe, after the prefilled syringe plunger has pushed away the intervening lubricant or adhered to the barrel due to decomposition of the lubricant between the plunger and the barrel. The breakout force is the force needed to overcome "sticktion," an industry term for the adhesion between the plunger and barrel that needs to be overcome to break out the plunger and allow it to begin moving.

V.C. Some utilities of coating a vessel in whole or in part with a lubricity layer, such as selectively at surfaces contacted in sliding relation to other parts, is to ease the insertion or removal of a stopper or passage of a sliding element such as a piston in a syringe or a stopper in a sample tube. The vessel can be made, for example, in whole or in part of a polymer material such as a cyclic olefin polymer (COP), optionally also including other materials. Applying a lubricity layer or coating by PECVD can avoid or reduce the need to coat the vessel wall or closure with a sprayed, dipped, or otherwise applied organosilicon or other lubricant that commonly is applied in a far larger quantity than would be deposited by a PECVD process.

V.C. In any of the above embodiments V.C., a plasma, optionally a non-hollow-cathode plasma, optionally can be formed in the vicinity of the substrate In any of embodiments V.C., the precursor optionally can be provided in the substantial absence of nitrogen. V.C. In any of embodiments V.C., the precursor optionally can be provided at less than 1 Torr absolute pressure.

V.C. In any of embodiments V.C., the precursor optionally can be provided to the vicinity of a plasma emission.

V.C. In any of embodiments V.C., the coating optionally can be applied to the substrate at a thickness of 1 to 5000 nm, or 10 to 1000 nm, or 10-200 nm, or 20 to 100 nm thick. The thickness of this and other coatings can be measured, for example, by transmission electron microscopy (TEM).

V.C. The TEM can be carried out, for example, as follows. Samples can be prepared for Focused Ion Beam (FIB) cross-sectioning in two ways. Either the samples can be first coated with a thin layer or coating of carbon (50-100 nm thick) and then coated with a sputtered layer or coating of platinum (50-100 nm thick) using a K575X Emitech coating system, or the samples can be coated directly with the protective sputtered Pt layer. The coated samples can be placed in an FEI FIB200 FIB system. An additional layer or coating of platinum can be FIB-deposited by injection of an oregano-metallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using a proprietary in-situ FIB lift-out technique. The cross sections can be attached to a 200 mesh copper TEM grid using FIB-deposited platinum. One or two windows in each section, measuring ~8 μm wide, can be thinned to electron transparency using the gallium ion beam of the FEI FIB.

V.C. Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | #2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec.(×4) |

V.C. For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | #1 |
| Objective Lens Aperture for imaging | #3 |
| Selective Area Aperture for SAD | N/A |

V.C. In any of embodiments V.C., the substrate can comprise glass or a polymer, for example a polycarbonate polymer, an olefin polymer, a cyclic olefin polymer, a polypropylene polymer, a polyester polymer, a polyethylene terephthalate polymer or a combination of any two or more of these.

V.C. In any of embodiments V.C., the PECVD optionally can be performed by energizing the gaseous reactant containing the precursor with electrodes powered at a RF frequency as defined above, for example a frequency from 10 kHz to less than 300 MHz, optionally from 1 to 50 MHz, even optionally from 10 to 15 MHz, optionally a frequency of 13.56 MHz.

V.C. In any of embodiments V.C., the plasma can be generated by energizing the gaseous reactant comprising the precursor with electrodes supplied with electric power sufficient to form a lubricity layer. Optionally, the plasma is generated by energizing the gaseous reactant containing the precursor with electrodes supplied with an electric power of from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity coatings to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

V.C. In any of embodiments V.C., one preferred combination of process gases includes octamethylcyclotetrasiloxane (OMCTS) or another cyclic siloxane as the precursor, in the presence of oxygen as the oxidizing gas and argon as the carrier gas. Without being bound according to the accuracy of this theory, the inventors believe this particular combination is effective for the following reasons.

V.C. It is believed that the OMCTS or other cyclic siloxane molecule provides several advantages over other siloxane materials. First, its ring structure results in a less dense coating (as compared to coatings prepared from HMDSO). The molecule also allows selective ionization so that the final structure and chemical composition of the coating can be directly controlled through the application of the plasma power. Other organosilicon molecules are readily ionized (fractured) so that it is more difficult to retain the original structure of the molecule.

V.C. Since the addition of Argon gas improves the lubricity performance (see the working examples below), it is believed that additional ionization of the molecule in the presence of Argon contributes to providing lubricity. The Si—O—Si bonds of the molecule have a high bond energy followed by the Si—C, with the C—H bonds being the weakest. Lubricity appears to be achieved when a portion of the C—H bonds are broken. This allows the connecting (cross-linking) of the structure as it grows. Addition of oxygen (with the Argon) is understood to enhance this process. A small amount of oxygen can also provide C—O bonding to which other molecules can bond. The combination of breaking C—H bonds and adding oxygen all at low pressure and power leads to a chemical structure that is solid while providing lubricity.

V.C. One contemplated product optionally can be a syringe having a barrel treated by the method of any one or more of embodiments V.C.

V.D. Liquid-Applied Coatings

V.D. Another example of a suitable barrier or other type of coating, usable in conjunction with PECVD-applied coatings or other PECVD treatment as disclosed here, can be a liquid barrier, lubricant, surface energy tailoring, or other type of coating 90 applied to the interior surface of a vessel, either directly or with one or more intervening PECVD-applied coatings described in this specification, for example $SiO_x$, a lubricity layer or coating characterized as defined in the Definition Section, or both.

V.D. Suitable liquid barriers or other types of coatings 90 also optionally can be applied, for example, by applying a liquid monomer or other polymerizable or curable material to the interior surface of the vessel 80 and curing, polymerizing, or crosslinking the liquid monomer to form a solid polymer. Suitable liquid barrier or other types of coatings 90 can also be provided by applying a solvent-dispersed polymer to the surface 88 and removing the solvent.

V.D. Either of the above methods can include as a step forming a coating 90 on the interior 88 of a vessel 80 via the vessel port 92 at a processing station or device 28. One example is applying a liquid coating, for example of a curable monomer, prepolymer, or polymer dispersion, to the interior surface 88 of a vessel 80 and curing it to form a film that physically isolates the contents of the vessel 80 from its interior surface 88. The prior art describes polymer coating technology as suitable for coating plastic blood collection tubes. For example, the acrylic and polyvinylidene chloride (PVdC) coating materials and coating methods described in U.S. Pat. No. 6,165,566, which is hereby incorporated by reference, optionally can be used.

V.D. Either of the above methods can also or include as a step forming a coating on the exterior outer wall of a vessel 80. The coating optionally can be a barrier coating, optionally an oxygen barrier coating, or optionally a water barrier coating. One example of a suitable coating is polyvinylidene chloride, which functions both as a water barrier and an oxygen barrier. Optionally, the barrier coating can be applied as a water-based coating. The coating optionally can be applied by dipping the vessel in it, spraying it on the vessel, or other expedients. A vessel having an exterior barrier coating as described above is also contemplated.

VII. PECVD Treated Vessels

VII. Vessels are contemplated having a barrier coating 90 (shown in FIG. 1, for example), which can be an $SiO_x$ coating applied to a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated. The thickness of the $SiO_x$ or other coating can be measured, for example, by transmission electron microscopy (TEM), and its composition can be measured by X-ray photoelectron spectroscopy (XPS).

VII. It is contemplated that the choice of the material to be barred from permeating the coating and the nature of the $SiO_x$ coating applied can affect its barrier efficacy. For example, two examples of material commonly intended to be barred are oxygen and water/water vapor. Materials commonly are a better barrier to one than to the other. This is believed to be so at least in part because oxygen is transmitted through the coating by a different mechanism than water is transmitted.

VII. Oxygen transmission is affected by the physical features of the coating, such as its thickness, the presence of cracks, and other physical details of the coating. Water transmission, on the other hand, is believed to commonly be affected by chemical factors, i.e. the material of which the coating is made, more than physical factors. The inventors also believe that at least one of these chemical factors is a substantial concentration of OH moieties in the coating, which leads to a higher transmission rate of water through the barrier. An $SiO_x$ coating often contains OH moieties, and thus a physically sound coating containing a high proportion of OH moieties is a better barrier to oxygen than to water. A physically sound carbon-based barrier, such as amorphous carbon or diamond-like carbon (DLC) commonly is a better barrier to water than is a $SiO_x$ coating because the carbon-based barrier more commonly has a lower concentration of OH moieties.

VII. Other factors lead to a preference for an $SiO_x$ coating, however, such as its oxygen barrier efficacy and its close chemical resemblance to glass and quartz. Glass and quartz (when used as the base material of a vessel) are two materials long known to present a very high barrier to oxygen and water transmission as well as substantial inertness to many materials commonly carried in vessels. Thus, it is commonly desirable to optimize the water barrier properties such as the water vapor transmission rate (WVTR) of an $SiO_x$ coating, rather than choosing a different or additional type of coating to serve as a water transmission barrier.

VII. Several ways contemplated to improve the WVTR of an $SiO_x$ coating are as follow.

VII. The concentration ratio of organic moieties (carbon and hydrogen compounds) to OH moieties in the deposited coating can be increased. This can be done, for example, by increasing the proportion of oxygen in the feed gases (as by increasing the oxygen feed rate or by lowering the feed rate of one or more other constituents). The lowered incidence of OH moieties is believed to result from increasing the degree of reaction of the oxygen feed with the hydrogen in the silicone source to yield more volatile water in the PECVD exhaust and a lower concentration of OH moieties trapped or incorporated in the coating.

VII. Higher energy can be applied in the PECVD process, either by raising the plasma generation power level, by applying the power for a longer period, or both. An increase in the applied energy must be employed with care when used to coat a plastic tube or other device, as it also has a tendency to distort the vessel being treated, to the extent the tube absorbs the plasma generation power. This is why RF power is contemplated in the context of present application. Distortion of the medical devices can be reduced or eliminated by employing the energy in a series of two or more pulses separated by cooling time, by cooling the vessels while applying energy, by applying the coating in a shorter time (commonly thus making it thinner), by selecting a frequency of the applied coating that is absorbed minimally by the base material selected for being coated, and/or by applying more than one coating, with time in between the respective energy application steps. For example, high power pulsing can be used with a duty cycle of 1 millisecond on, 99 milliseconds off, while continuing to feed the gaseous reactant or process gas. The gaseous reactant or process gas is then the coolant, as it keeps flowing between pulses. Another alternative is to reconfigure the power applicator, as by adding magnets to confine the plasma increase the effective power application (the power that actually results in incremental coating, as opposed to waste power that results in heating or unwanted coating). This expedient results in the application of more coating-formation energy per total Watt-hour of energy applied. See for example U.S. Pat. No. 5,904,952.

VII. An oxygen post-treatment of the coating can be applied to remove OH moieties from the previously-deposited coating. This treatment is also contemplated to remove residual volatile organosilicon compounds or silicones or oxidize the coating to form additional $SiO_x$.

VII. The plastic base material tube can be preheated.

VII. A different volatile source of silicon, such as hexamethyldisilazane (HMDZ), can be used as part or all of the silicone feed. It is contemplated that changing the feed gas to HMDZ will address the problem because this compound has no oxygen moieties in it, as supplied. It is contemplated that one source of OH moieties in the HMDSO-sourced coating is hydrogenation of at least some of the oxygen atoms present in unreacted HMDSO.

VII. A composite coating can be used, such as a carbon-based coating combined with $SiO_x$. This can be done, for example, by changing the reaction conditions or by adding a substituted or unsubstituted hydrocarbon, such as an alkane, alkene, or alkyne, to the feed gas as well as an organosilicon-based compound. See for example U.S. Pat. No. 5,904,952, which states in relevant part: "For example, inclusion of a lower hydrocarbon such as propylene provides carbon moieties and improves most properties of the deposited films (except for light transmission), and bonding analysis indicates the film to be silicon dioxide in nature. Use of methane, methanol, or acetylene, however, produces films that are silicone in nature. The inclusion of a minor amount of gaseous nitrogen to the gas stream provides nitrogen moieties in the deposited films and increases the deposition rate, improves the transmission and reflection optical properties on glass, and varies the index of refraction in response to varied amounts of $N_2$. The addition of nitrous oxide to the gas stream increases the deposition rate and improves the optical properties, but tends to decrease the film hardness." Suitable hydrocarbons include methane, ethane, ethylene, propane, acetylene, or a combination of two or more of these.

VII. A diamond-like carbon (DLC) coating can be formed as the primary or sole coating deposited. This can be done, for example, by changing the reaction conditions or by feeding methane, hydrogen, and helium to a PECVD process. These reaction feeds have no oxygen, so no OH moieties can be formed. For one example, an $SiO_x$ coating can be applied on the interior of a tube or syringe barrel and an outer DLC coating can be applied on the exterior surface of a tube or syringe barrel. Or, the $SiO_x$ and DLC coatings can both be applied as a single layer or coating or plural layers of an interior tube or syringe barrel coating.

VII. Referring to FIG. 1, the barrier or other type of coating 90 reduces the transmission of atmospheric gases into the vessel 80 through its interior surface 88. Or, the barrier or other type of coating 90 reduces the contact of the contents of the vessel 80 with the interior surface 88. The barrier or other type of coating can comprise, for example, $SiO_x$, amorphous (for example, diamond-like) carbon, or a combination of these.

VII. Any coating described herein can be used for coating a surface, for example a plastic surface. It can further be used as a barrier layer, for example as a barrier against a gas or liquid, optionally against water vapor, oxygen and/or air. It can also be used for preventing or reducing mechanical and/or chemical effects which the coated surface would have on a compound or composition if the surface are uncoated. For example, it can prevent or reduce the precipitation of a compound or composition, for example insulin precipitation or blood clotting or platelet activation.

VII.A. Evacuated Blood Collection Vessels

VII.A.1. Tubes

VII.A.I. Referring to FIG. 1, more details of the vessel such as 80 are shown. The illustrated vessel 80 can be generally tubular, having an opening 82 at one end of the vessel, opposed by a closed end 84. The vessel 80 also has a wall 86 defining an interior surface 88. One example of the vessel 80 is a medical sample tube, such as an evacuated blood collection tube, as commonly is used by a phlebotomist for receiving a venipuncture sample of a patient's blood for use in a medical laboratory.

VII.A.1. The vessel 80 can be made, for example, of thermoplastic material. Some examples of suitable thermoplastic material are polyethylene terephthalate or a polyolefin such as polypropylene or a cyclic polyolefin copolymer.

VII.A.1. The vessel 80 can be made by any suitable method, such as by injection molding, by blow molding, by machining, by fabrication from tubing stock, or by other suitable means. PECVD can be used to form a coating on the internal surface of $SiO_x$.

VII.A.1. If intended for use as an evacuated blood collection tube, the vessel 80 desirably can be strong enough to withstand a substantially total internal vacuum substantially without deformation when exposed to an external pressure of 760 Torr or atmospheric pressure and other coating processing conditions. This property can be provided, in a thermoplastic vessel 80, by providing a vessel 80 made of suitable materials having suitable dimensions and a glass transition temperature higher than the processing temperature of the coating process, for example a cylindrical wall 86 having sufficient wall thickness for its diameter and material.

VII.A.1. Medical vessels or containers like sample collection tubes and syringes are relatively small and are injection molded with relatively thick walls, which renders them able to be evacuated without being crushed by the ambient atmospheric pressure. They are thus stronger than carbonated soft drink bottles or other larger or thinner-walled plastic containers. Since sample collection tubes designed for use as evacuated vessels typically are constructed to withstand a full vacuum during storage, they can be used as vacuum chambers.

VII.A.1. Such adaptation of the vessels to be their own vacuum chambers might eliminate the need to place the vessels into a vacuum chamber for PECVD treatment, which typically is carried out at very low pressure. The use of a vessel as its own vacuum chamber can result in faster processing time (since loading and unloading of the parts from a separate vacuum chamber is not necessary) and can lead to simplified equipment configurations. Furthermore, a vessel holder is contemplated, for certain embodiments, that will hold the device (for alignment to gas tubes and other apparatus), seal the device (so that the vacuum can be created by attaching the vessel holder to a vacuum pump) and move the device between molding and subsequent processing steps.

VII.A.1. A vessel 80 used as an evacuated blood collection tube should be able to withstand external atmospheric pressure, while internally evacuated to a reduced pressure useful for the intended application, without a substantial volume of air or other atmospheric gas leaking into the tube (as by bypassing the closure) or permeating through the wall 86 during its shelf life. If the as-molded vessel 80 cannot meet this requirement, it can be processed by coating the interior surface 88 with a barrier or other type of coating 90. It is desirable to treat and/or coat the interior surfaces of these devices (such as sample collection tubes and syringe barrels) to impart various properties that will offer advantages over existing polymeric devices and/or to mimic existing glass products. It is also desirable to measure various properties of the devices before and/or after treatment or coating.

VII.A.1.a. Coating Deposited from an Organosilicon Precursor Made by In Situ Polymerizing Organosilicon Precursor VII.A.1.a. A process is contemplated for applying a lubricity layer or coating characterized as defined in the Definition Section on a substrate, for example the interior of the barrel of a syringe, comprising applying one of the described precursors on or in the vicinity of a substrate at a thickness of 1 to 5000 nm, optionally 10 to 1000 nm, optionally 10-200 nm, optionally 20 to 100 nm thick and crosslinking or polymerizing (or both) the coating, optionally in a PECVD process, to provide a lubricated surface. The coating applied by this process is also contemplated to be new.

VII.A.1.a. A coating of $Si_wO_xC_yH_z$ as defined in the Definition Section can have utility as a hydrophobic layer. Coatings of this kind are contemplated to be hydrophobic, independent of whether they function as lubricity layers. A coating or treatment is defined as "hydrophobic" if it lowers the wetting tension of a surface, compared to the corresponding uncoated or untreated surface. Hydrophobicity is thus a function of both the untreated substrate and the treatment.

VII.A.1.a. The degree of hydrophobicity of a coating can be varied by varying its composition, properties, or deposition method. For example, a coating of $SiO_x$ having little or no hydrocarbon content is more hydrophilic than a coating of $Si_wO_xC_yH_z$ as defined in the Definition Section. Generally speaking, the higher the C—$H_x$ (e.g. CH, $CH_2$, or $CH_3$) moiety content of the coating, either by weight, volume, or molarity, relative to its silicon content, the more hydrophobic the coating.

VII.A.1.a. A hydrophobic layer or coating can be very thin, having a thickness of at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The coating can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick. Specific thickness ranges composed of any one of the minimum thicknesses expressed above, plus any equal or greater one of the maximum thicknesses expressed above, are expressly contemplated.

VII.A.1.a. One utility for such a hydrophobic layer or coating is to isolate a thermoplastic tube wall, made for example of polyethylene terephthalate (PET), from blood collected within the tube. The hydrophobic layer or coating can be applied on top of a hydrophilic $SiO_x$ coating on the internal surface of the tube. The $SiO_x$ coating increases the barrier properties of the thermoplastic tube and the hydrophobic layer or coating changes the surface energy of blood contact surface with the tube wall. The hydrophobic layer or coating can be made by providing a precursor selected from those identified in this specification. For example, the hydrophobic layer or coating precursor can comprise hexamethyldisiloxane (HMDSO) or octamethylcyclotetrasiloxane (OMCTS).

VII.A.1.a. Another use for a hydrophobic layer or coating is to prepare a glass cell preparation tube. The tube has a wall defining a lumen, a hydrophobic layer or coating in the internal surface of the glass wall, and contains a citrate reagent. The hydrophobic layer or coating can be made by providing a precursor selected from those identified elsewhere in this specification. For another example, the hydrophobic layer or coating precursor can comprise hexamethyldisiloxane (HMDSO) or octamethylcyclotetrasiloxane (OMCTS). Another source material for hydrophobic layers is an alkyl trimethoxysilane of the formula:

R—Si(OCH₃)₃ in which R is a hydrogen atom or an organic substituent, for example methyl, ethyl, propyl, isopropyl, butyl, isobutyl, t-butyl, vinyl, alkyne, epoxide, or others. Combinations of two or more of these are also contemplated.

VII.A.1.a. Combinations of acid or base catalysis and heating, using an alkyl trimethoxysilane precursor as described above, can condense the precursor (removing ROH by-products) to form crosslinked polymers, which can optionally be further crosslinked via an alternative method. One specific example is by Shimojima et. al. J. Mater. Chem., 2007, 17, 658-663.

VII.A.1.a. A lubricity layer, characterized as defined in the Definition Section, can be applied as a subsequent coating after applying an $SiO_x$ barrier coating to the interior surface 88 of the vessel 80 to provide a lubricity layer, particularly if the lubricity layer or coating is a liquid organosiloxane compound at the end of the coating process.

VII.A.1.a. Optionally, after the lubricity layer or coating is applied, it can be post-cured after the PECVD process. Radiation curing approaches, including UV-initiated (free radical or cationic), electron-beam (E-beam), and thermal as described in Development Of Novel Cycloaliphatic Siloxanes For Thermal And UV-Curable Applications (Ruby Chakraborty Dissertation, can 2008) be utilized.

VII.A.1.a. Another approach for providing a lubricity layer or coating is to use a silicone demolding agent when injection-molding the thermoplastic vessel to be lubricated. For example, it is contemplated that any of the demolding agents and latent monomers causing in-situ thermal lubricity layer or coating formation during the molding process can be used. Or, the aforementioned monomers can be doped into traditional demolding agents to accomplish the same result.

VII.A.1.a. A lubricity layer, characterized as defined in the Definition Section, is particularly contemplated for the internal surface of a syringe barrel as further described below. A lubricated internal surface of a syringe barrel can reduce the plunger sliding force needed to advance a plunger in the barrel during operation of a syringe, or the breakout force to start a plunger moving after the prefilled syringe plunger has pushed away the intervening lubricant or adhered to the barrel, for example due to decomposition of the lubricant between the plunger and the barrel. As explained elsewhere in this specification, a lubricity layer or coating also can be applied to the interior surface 88 of the vessel 80 to improve adhesion of a subsequent coating of $SiO_x$.

VII.A.1.a. Thus, the coating 90 can comprise a layer or coating of $SiO_x$ and a lubricity layer or coating and/or hydrophobic layer, characterized as defined in the Definition Section. The lubricity layer or coating and/or hydrophobic layer or coating of $Si_wO_xC_yH_z$ can be deposited between the layer or coating of $SiO_x$ and the interior surface of the vessel. Or, the layer or coating of $SiO_x$ can be deposited between the lubricity layer or coating and/or hydrophobic layer or coating and the interior surface of the vessel. Or, three or more layers, either alternating or graduated between these two coating compositions: (1) a layer or coating of $SiO_x$ and (2) the lubricity layer or coating and/or hydrophobic layer; can also be used. The layer or coating of $SiO_x$ can be deposited adjacent to the lubricity layer or coating and/or hydrophobic layer or coating or remotely, with at least one intervening layer or coating of another material. The layer or coating of $SiO_x$ can be deposited adjacent to the interior surface of the vessel. Or, the lubricity layer or coating and/or hydrophobic layer or coating can be deposited adjacent to the interior surface of the vessel.

VII.A.1.a. Another expedient contemplated here, for adjacent layers of $SiO_x$ and a lubricity layer or coating and/or hydrophobic layer, is a graded composite of $Si_wO_xC_yH_z$, as defined in the Definition Section. A graded composite can be separate layers of a lubricity layer or coating and/or hydrophobic layer or coating and $SiO_x$ with a transition or interface of intermediate composition between them, or separate layers of a lubricity layer or coating and/or hydrophobic layer or coating and $SiO_x$ with an intermediate distinct layer or coating of intermediate composition between them, or a single layer or coating that changes continuously or in steps from a composition of a lubricity layer or coating and/or hydrophobic layer or coating to a composition more like $SiO_x$, going through the coating in a normal direction.

VII.A.1.a. The grade in the graded composite can go in either direction. For example, the a lubricity layer or coating and/or hydrophobic layer or coating can be applied directly to the substrate and graduate to a composition further from the surface of $SiO_x$. Or, the composition of $SiO_x$ can be applied directly to the substrate and graduate to a composition further from the surface of a lubricity layer or coating and/or hydrophobic layer. A graduated coating is particularly contemplated if a coating of one composition is better for adhering to the substrate than the other, in which case the better-adhering composition can, for example, be applied directly to the substrate. It is contemplated that the more distant portions of the graded coating can be less compatible with the substrate than the adjacent portions of the graded coating, since at any point the coating is changing gradually in properties, so adjacent portions at nearly the same depth of the coating have nearly identical composition, and more widely physically separated portions at substantially different depths can have more diverse properties. It is also contemplated that a coating portion that forms a better barrier against transfer of material to or from the substrate can be directly against the substrate, to prevent the more remote coating portion that forms a poorer barrier from being contaminated with the material intended to be barred or impeded by the barrier.

VII.A.1.a. The coating, instead of being graded, optionally can have sharp transitions between one layer or coating and the next, without a substantial gradient of composition. Such coatings can be made, for example, by providing the gases to produce a layer or coating as a steady state flow in a non-plasma state, then energizing the system with a brief plasma discharge to form a coating on the substrate. If a subsequent coating is to be applied, the gases for the previous coating are cleared out and the gases for the next coating are applied in a steady-state fashion before energizing the plasma and again forming a distinct layer or coating on the surface of the substrate or its outermost previous coating, with little if any gradual transition at the interface.

VII.A.1.b. Citrate Blood Tube Having Wall Coated with Hydrophobic Layer or coating Deposited from an Organosilicon Precursor VII.A.1.b. Another embodiment is a cell preparation tube having a wall provided with a hydrophobic layer or coating on its inside surface and containing an aqueous sodium citrate reagent. The hydrophobic layer or coating can be also be applied on top of a hydrophilic $SiO_x$ coating on the internal surface of the tube. The $SiO_x$ coating increases the barrier properties of the thermoplastic tube and the hydrophobic layer or coating changes the surface energy of blood contact surface with the tube wall.

VII.A.1.b. The wall is made of thermoplastic material having an internal surface defining a lumen.

VII.A.1.b. A blood collection tube according to the embodiment VII.A.1.b can have a first layer or coating of $SiO_x$ on the internal surface of the tube, applied as explained in this specification, to function as an oxygen barrier and extend the shelf life of an evacuated blood collection tube made of thermoplastic material. A second layer or coating of a hydrophobic layer, characterized as defined in the Definition Section, can then be applied over the barrier layer or coating on the internal surface of the tube to provide a hydrophobic surface. The coating is effective to reduce the platelet activation of blood plasma treated with a sodium citrate additive and exposed to the inner surface, compared to the same type of wall uncoated.

VII.A.1.b. PECVD is used to form a hydrophobic layer or coating on the internal surface, characterized as defined in the Definition Section. Unlike conventional citrate blood collection tubes, the blood collection tube having a hydrophobic layer, characterized as defined in the Definition Section does not require a coating of baked on silicone on the vessel wall, as is conventionally applied to make the surface of the tube hydrophobic.

VII.A.1.b. Both layers can be applied using the same precursor, for example HMDSO or OMCTS, and different PECVD reaction conditions.

VII.A.1.b. A sodium citrate anticoagulation reagent is then placed within the tube and it is evacuated and sealed with a closure to produce an evacuated blood collection tube. The components and formulation of the reagent are known to those skilled in the art. The aqueous sodium citrate reagent is disposed in the lumen of the tube in an amount effective to inhibit coagulation of blood introduced into the tube.

VII.A.1.e. Barrier Coating Made of Glass

VII.A.1.e. Another embodiment is a vessel including a vessel, a barrier coating, and a closure. The vessel is generally tubular and made of thermoplastic material. The vessel has a mouth and a lumen bounded at least in part by a wall having an inner surface interfacing with the lumen. There is an at least essentially continuous barrier coating made of glass on the inner surface of the wall. A closure covers the mouth and isolates the lumen of the vessel from ambient air.

VII.A.1.e. The vessel 80 can also be made, for example of glass of any type used in medical or laboratory applications, such as soda-lime glass, borosilicate glass, or other glass formulations. Other vessels having any shape or size, made of any material, are also contemplated for use in the system 20. One function of coating a glass vessel can be to reduce the ingress of ions in the glass, either intentionally or as impurities, for example sodium, calcium, or others, from the glass to the contents of the vessel, such as a reagent or blood in an evacuated blood collection tube. Another function of coating a glass vessel in whole or in part, such as selectively at surfaces contacted in sliding relation to other parts, is to provide lubricity to the coating, for example to ease the insertion or removal of a stopper or passage of a sliding element such as a piston in a syringe. Still another reason to coat a glass vessel is to prevent a reagent or intended sample for the vessel, such as blood, from sticking to the wall of the vessel or an increase in the rate of coagulation of the blood in contact with the wall of the vessel.

VII.A.1.e.i. A related embodiment is a vessel as described in the previous paragraph, in which the barrier coating is made of soda lime glass, borosilicate glass, or another type of glass.

VII.A.2. Stoppers

Figure 4:
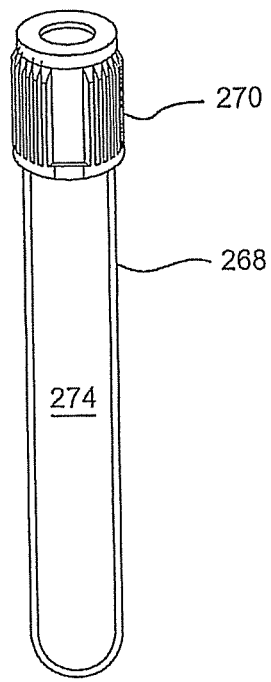
FIG. 4 is a perspective view of a blood collection tube assembly having a closure according to still another embodiment of the invention.

VII.A.2. FIGS. 4-6 illustrate a vessel 268, which can be an evacuated blood collection tube, having a closure 270 to isolate the lumen 274 from the ambient environment. The closure 270 comprises a interior-facing surface 272 exposed to the lumen 274 of the vessel 268 and a wall-contacting surface 276 that is in contact with the inner surface 278 of the vessel wall 280. In the illustrated embodiment the closure 270 is an assembly of a stopper 282 and a shield 284.

VII.A.2.a. Method of Applying Lubricity Layer or Coating to Stopper in Vacuum Chamber VII.A.2.a. Another embodiment is a method of applying a coating on an elastomeric stopper such as 282. The stopper 282, separate from the vessel 268, is placed in a substantially evacuated chamber. A reaction mixture is provided including plasma forming gas, i.e. an organosilicon compound gas, optionally an oxidizing gas, and optionally a hydrocarbon gas. Plasma is formed in the reaction mixture, which is contacted with the stopper. A lubricity and/or hydrophobic layer, characterized as defined in the Definition Section, is deposited on at least a portion of the stopper.

VII.A.2.a. In the illustrated embodiment, the wall-contacting surface 276 of the closure 270 is coated with a lubricity layer or coating 286.

VII.A.2.a. In some embodiments, the lubricity and/or hydrophobic layer, characterized as defined in the Definition Section, is effective to reduce the transmission of one or more constituents of the stopper, such as a metal ion constituent of the stopper, or of the vessel wall, into the vessel lumen. Certain elastomeric compositions of the type useful for fabricating a stopper 282 contain trace amounts of one or more metal ions. These ions sometimes should not be able to migrate into the lumen 274 or come in substantial quantities into contact with the vessel contents, particularly if the sample vessel 268 is to be used to collect a sample for trace metal analysis. It is contemplated for example that coatings containing relatively little organic content, i.e. where y and z of $Si_wO_xC_yH_z$ as defined in the Definition Section are low or zero, are particularly useful as a metal ion barrier in this application. Regarding silica as a metal ion barrier see, for example, Anupama Mallikarjunan, Jasbir Juneja, Guangrong Yang, Shyam P. Murarka, and Toh-Ming Lu, The Effect of Interfacial Chemistry on Metal Ion Penetration into Polymeric Films, Mat. Res. Soc. Symp. Proc., Vol. 734, pp. B9.60.1 to B9.60.6 (Materials Research Society, 2003); U.S. Pat. Nos. 5,578,103 and 6,200,658, and European Appl. EP0697378 A2, which are all incorporated here by reference. It is contemplated, however, that some organic content can be useful to provide a more elastic coating and to adhere the coating to the elastomeric surface of the stopper 282.

VII.A.2.a. In some embodiments, the lubricity and/or hydrophobic layer, characterized as defined in the Definition Section, can be a composite of material having first and second layers, in which the first or inner layer or coating 288 interfaces with the elastomeric stopper 282 and is effective to reduce the transmission of one or more constituents of the stopper 282 into the vessel lumen. The second layer or coating 286 can interface with the inner wall 280 of the vessel and is effective as a lubricity layer or coating to reduce friction between the stopper 282 and the inner wall 280 of the vessel when the stopper 282 is seated on or in the vessel 268. Such composites are described in connection with syringe coatings elsewhere in this specification.

VII.A.2.a. Or, the first and second layers 288 and 286 are defined by a coating of graduated properties, in which the values of y and z defined in the Definition Section are greater in the first layer or coating than in the second layer.

VII.A.2.a. The lubricity and/or hydrophobic layer or coating can be applied, for example, by PECVD substantially as previously described. The lubricity and/or hydrophobic layer or coating can be, for example, between 0.5 and 5000 nm (5 to 50,000 Angstroms) thick, or between 1 and 5000 nm thick, or between 5 and 5000 nm thick, or between 10 and 5000 nm thick, or between 20 and 5000 nm thick, or between 50 and 5000 nm thick, or between 100 and 5000 nm thick, or between 200 and 5000 nm thick, or between 500 and 5000 nm thick, or between 1000 and 5000 nm thick, or between 2000 and 5000 nm thick, or between 3000 and 5000 nm thick, or between 4000 and 10,000 nm thick.

VII.A.2.a. Certain advantages are contemplated for plasma coated lubricity layers, versus the much thicker (one micron or greater) conventional spray applied silicone lubricants. Plasma coatings have a much lower migratory potential to move into blood versus sprayed or micron-coated silicones, both because the amount of plasma coated material is much less and because it can be more intimately applied to the coated surface and better bonded in place.

VII.A.2.a. Nanocoatings, as applied by PECVD, are contemplated to offer lower resistance to sliding of an adjacent surface or flow of an adjacent fluid than micron coatings, as the plasma coating tends to provide a smoother surface.

VII.A.2.a. Still another embodiment is a method of applying a coating of a lubricity and/or hydrophobic layer or coating on an elastomeric stopper. The stopper can be used, for example, to close the vessel previously described. The method includes several parts. A stopper is placed in a substantially evacuated chamber. A reaction mixture is provided comprising plasma forming gas, i.e. an organosilicon compound gas, optionally an oxidizing gas, and optionally a hydrocarbon gas. Plasma is formed in the reaction mixture. The stopper is contacted with the reaction mixture, depositing the coating of a lubricity and/or hydrophobic layer or coating on at least a portion of the stopper.

VII.A.2.a. In practicing this method, to obtain higher values of y and z as defined in the Definition Section, it is contemplated that the reaction mixture can comprise a hydrocarbon gas, as further described above and below. Optionally, the reaction mixture can contain oxygen, if lower values of y and z or higher values of x are contemplated. Or, particularly to reduce oxidation and increase the values of y and z, the reaction mixture can be essentially free of an oxidizing gas.

VII.A.2.a. In practicing this method to coat certain embodiments of the stopper such as the stopper 282, it is contemplated to be unnecessary to project the reaction mixture into the concavities of the stopper. For example, the wall-contacting and interior facing surfaces 276 and 272 of the stopper 282 are essentially convex, and thus readily treated by a batch process in which a multiplicity of stoppers such as 282 can be located and treated in a single substantially evacuated reaction chamber. It is further contemplated that in some embodiments the coatings 286 and 288 do not need to present as formidable a barrier to oxygen or water as the barrier coating on the interior surface 280 of the vessel 268, as the material of the stopper 282 can serve this function to a large degree.

VII.A.2.a. Many variations of the stopper and the stopper coating process are contemplated. The stopper 282 can be contacted with the plasma. Or, the plasma can be formed upstream of the stopper 282, producing plasma product, and the plasma product can be contacted with the stopper 282. The plasma can be formed by exciting the reaction mixture with electromagnetic energy and/or microwave energy.

VII.A.2.a. Variations of the reaction mixture are contemplated. The plasma forming gas can include an inert gas, also referred to herein as a carrier gas. The inert gas can be, for example, argon, helium, xenon, neon, krypton, or any mixture of two or more of these. In particular, the inert gas can be neon, argon or helium. The organosilicon compound gas can be, or include, HMDSO, OMCTS, any of the other organosilicon compounds mentioned in this disclosure, or a combination of two or more of these. The oxidizing gas can be oxygen or the other gases mentioned in this disclosure, or a combination of two or more of these. The hydrocarbon gas can be, for example, methane, methanol, ethane, ethylene, ethanol, propane, propylene, propanol, acetylene, or a combination of two or more of these.

VII.A.2.b. Applying by PECVD a Coating of Group III or IV Element and Carbon on a Stopper VII.A.2.b. Another embodiment is a method of applying a coating of a composition including carbon and one or more elements of Groups III or IV on an elastomeric stopper. To carry out the method, a stopper is located in a deposition chamber.

VII.A.2.b. A reaction mixture is provided in the deposition chamber, including a plasma forming gas with a gaseous source of a Group III element, a Group IV element, or a combination of two or more of these. The reaction mixture optionally contains an oxidizing gas and optionally contains a gaseous compound having one or more C—H bonds. Plasma is formed in the reaction mixture, and the stopper is contacted with the reaction mixture. A coating of a Group III element or compound, a Group IV element or compound, or a combination of two or more of these is deposited on at least a portion of the stopper.

VII.A.3. Stoppered Plastic Vessel Having Barrier Coating Effective to Provide 95% Vacuum Retention for 24 Months VII.A.3. Another embodiment is a vessel including a vessel, a barrier coating, and a closure. The vessel is generally tubular and made of thermoplastic material. The vessel has a mouth and a lumen bounded at least in part by a wall. The wall has an inner surface interfacing with the lumen. An at least essentially continuous barrier coating is applied on the inner surface of the wall. The barrier coating is effective to provide a substantial shelf life. A closure is provided covering the mouth of the vessel and isolating the lumen of the vessel from ambient air.

VII.A.3. Referring to FIGS. 4-6, a vessel 268 such as an evacuated blood collection tube or other vessel is shown.

VII.A.3. The vessel is, in this embodiment, a generally tubular vessel having an at least essentially continuous barrier coating and a closure. The vessel is made of thermoplastic material having a mouth and a lumen bounded at least in part by a wall having an inner surface interfacing with the lumen. The barrier coating is deposited on the inner surface of the wall, and is effective to maintain at least 95%, or at least 90%, of the initial vacuum level of the vessel for a shelf life of at least 24 months, optionally at least 30 months, optionally at least 36 months. The closure covers the mouth of the vessel and isolates the lumen of the vessel from ambient air.

VII.A.3. The closure, for example the closure 270 illustrated in the Figures or another type of closure, is provided to maintain a partial vacuum and/or to contain a sample and limit or prevent its exposure to oxygen or contaminants. FIGS. 4-6 are based on figures found in U.S. Pat. No. 6,602,206, but the present discovery is not limited to that or any other particular type of closure.

VII.A.3. The closure 270 comprises a interior-facing surface 272 exposed to the lumen 274 of the vessel 268 and a wall-contacting surface 276 that is in contact with the inner surface 278 of the vessel wall 280. In the illustrated embodiment the closure 270 is an assembly of a stopper 282 and a shield 284.

VII.A.3. In the illustrated embodiment, the stopper 282 defines the wall-contacting surface 276 and the inner surface 278, while the shield is largely or entirely outside the stoppered vessel 268, retains and provides a grip for the stopper 282, and shields a person removing the closure 270 from being exposed to any contents expelled from the vessel 268, such as due to a pressure difference inside and outside of the vessel 268 when the vessel 268 is opened and air rushes in or out to equalize the pressure difference.

VII.A.3. It is further contemplated that the coatings on the vessel wall 280 and the wall contacting surface 276 of the stopper can be coordinated. The stopper can be coated with a lubricity silicone layer, and the vessel wall 280, made for example of PET or glass, can be coated with a harder $SiO_x$ layer, or with an underlying $SiO_x$ layer or coating and a lubricity overcoat.

VII.B. Syringes

VII.B. The foregoing description has largely addressed applying a barrier coating to a tube with one permanently closed end, such as a blood collection tube or, more generally, a specimen receiving tube 80. The apparatus is not limited to such a device.

VII.B. Another example of a suitable vessel, shown in FIGS. 20-22, is a syringe barrel 250 for a medical syringe 252. Such syringes 252 are sometimes supplied prefilled with saline solution, a pharmaceutical preparation, or the like for use in medical techniques. Pre-filled syringes 252 are also contemplated to benefit from an $SiO_x$ barrier or other type of coating on the interior surface 254 to keep the contents of the prefilled syringe 252 out of contact with the plastic of the syringe, for example of the syringe barrel 250 during storage. The barrier or other type of coating can be used to avoid leaching components of the plastic into the contents of the barrel through the interior surface 254.

VII.B. A syringe barrel 250 as molded commonly can be open at both the back end 256, to receive a plunger 258, and at the front end 260, to receive a hypodermic needle, a nozzle, or tubing for dispensing the contents of the syringe 252 or for receiving material into the syringe 252. But the front end 260 can optionally be capped and the plunger 258 optionally can be fitted in place before the prefilled syringe 252 is used, closing the barrel 250 at both ends. A cap 262 can be installed either for the purpose of processing the syringe barrel 250 or assembled syringe, or to remain in place during storage of the prefilled syringe 252, up to the time the cap 262 is removed and (optionally) a hypodermic needle or other delivery conduit is fitted on the front end 260 to prepare the syringe 252 for use.

VII.B.1.a. Syringe Having Barrel Coated with Lubricity Layer or Coating Deposited from an Organosilicon Precursor VII.B.1.a. Still another embodiment is a vessel having a lubricity layer, characterized as defined in the Definition Section, of the type made by the following process.

VII.B.1.a. A precursor is provided as defined above.

VII.B.1.a. The precursor is applied to a substrate under conditions effective to form a coating. The coating is polymerized or crosslinked, or both, to form a lubricated surface having a lower plunger sliding force or breakout force than the untreated substrate.

VII.B.1.a. Respecting any of the Embodiments VII and sub-parts, optionally the applying step is carried out by vaporizing the precursor and providing it in the vicinity of the substrate.

VII.B.1.a. Respecting any of the Embodiments VII.A.1.a.i, optionally a plasma, optionally a non-hollow-cathode plasma, is formed in the vicinity of the substrate. Optionally, the precursor is provided in the substantial absence of nitrogen. Optionally, the precursor is provided at less than 1 Torr absolute pressure. Optionally, the precursor is provided to the vicinity of a plasma emission. Optionally, the precursor its reaction product is applied to the substrate at a thickness of 1 to 5000 nm thick, or 10 to 1000 nm thick, or 10-200 nm thick, or 20 to 100 nm thick. Optionally, the substrate comprises glass. Optionally, the substrate comprises a polymer, optionally a polycarbonate polymer, optionally an olefin polymer, optionally a cyclic olefin polymer, optionally a polypropylene polymer, optionally a polyester polymer, optionally a polyethylene terephthalate polymer.

VII.B.1.a. Optionally, the plasma is generated by energizing the gaseous reactant containing the precursor with electrodes powered, for example, at a RF frequency as defined above, for example a frequency of from 10 kHz to less than 300 MHz, optionally from 1 to 50 MHz, even optionally from 10 to 15 MHz, optionally a frequency of 13.56 MHz.

VII.B.1.a. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. Another embodiment is a lubricity layer, characterized as defined in the Definition Section, on the inner wall of a syringe barrel. The coating is produced from a PECVD process using the following materials and conditions. A cyclic precursor is optionally employed, selected from a monocyclic siloxane, a polycyclic siloxane, or a combination of two or more of these, as defined elsewhere in this specification for lubricity layers. One example of a suitable cyclic precursor comprises octamethylcyclotetrasiloxane (OMCTS), optionally mixed with other precursor materials in any proportion. Optionally, the cyclic precursor consists essentially of octamethycyclotetrasiloxane (OMCTS), meaning that other precursors can be present in amounts which do not change the basic and novel properties of the resulting lubricity layer, i.e. its reduction of the plunger sliding force or breakout force of the coated surface.

VII.B.1.a. A sufficient plasma generation power input, for example any power level successfully used in one or more working examples of this specification or described in the specification, is provided to induce coating formation.

VII.B.1.a. The materials and conditions employed are effective to reduce the syringe plunger sliding force or breakout force moving through the syringe barrel at least 25 percent, alternatively at least 45 percent, alternatively at least 60 percent, alternatively greater than 60 percent, relative to an uncoated syringe barrel. Ranges of plunger sliding force or breakout force reduction of from 20 to 95 percent, alternatively from 30 to 80 percent, alternatively from 40 to 75 percent, alternatively from 60 to 70 percent, are contemplated.

VII.B.1.a. Another embodiment is a vessel having a hydrophobic layer, characterized as defined in the Definition Section, on the inside wall. The coating is made as explained for the lubricant coating of similar composition, but under conditions effective to form a hydrophobic surface having a higher contact angle than the untreated substrate.

VII.B.1.a. Respecting any of the Embodiments VII.A.1.a.ii, optionally the substrate comprises glass or a polymer. The glass optionally is borosilicate glass. The polymer is optionally a polycarbonate polymer, optionally an olefin polymer, optionally a cyclic olefin polymer, optionally a polypropylene polymer, optionally a polyester polymer, optionally a polyethylene terephthalate polymer.

VII.B.1.a. Another embodiment is a syringe including a plunger, a syringe barrel, and a lubricity layer, characterized as defined in the Definition Section. The syringe barrel includes an interior surface receiving the plunger for sliding. The lubricity layer or coating is disposed on the interior surface of the syringe barrel. The lubricity layer or coating optionally can be less than 1000 nm thick and effective to reduce the breakout force or the plunger sliding force necessary to move the plunger within the barrel. Reducing the plunger sliding force is alternatively expressed as reducing the coefficient of sliding friction of the plunger within the barrel or reducing the plunger force; these terms are regarded as having the same meaning in this specification.

VII.B.1.a. The syringe 544 comprises a plunger 546 and a syringe barrel 548. The syringe barrel 548 has an interior surface 552 receiving the plunger for sliding 546. The interior surface 552 of the syringe barrel 548 further comprises a lubricity layer or coating 554, characterized as defined in the Definition Section. The lubricity layer or coating is less than 1000 nm thick, optionally less than 500 nm thick, optionally less than 200 nm thick, optionally less than 100 nm thick, optionally less than 50 nm thick, and is effective to reduce the breakout force necessary to overcome adhesion of the plunger after storage or the plunger sliding force necessary to move the plunger within the barrel after it has broken away. The lubricity layer or coating is characterized by having a plunger sliding force or breakout force lower than that of the uncoated surface.

VII.B.1.a. Any of the above precursors of any type can be used alone or in combinations of two or more of them to provide a lubricity layer.

VII.B.1.a. In addition to utilizing vacuum processes, low temperature atmospheric (non-vacuum) plasma processes can also be utilized to induce molecular ionization and deposition through precursor monomer vapor delivery optionally in a non-oxidizing atmosphere such as helium or argon. Separately, thermal CVD can be considered via flash thermolysis deposition.

VII.B.1.a. The approaches above are similar to vacuum PECVD in that the surface coating and crosslinking mechanisms can occur simultaneously.

VII.B.1.a. Yet another expedient contemplated for any coating or coatings described here is a coating that is not uniformly applied over the entire interior 88 of a vessel. For example, a different or additional coating can be applied selectively to the cylindrical portion of the vessel interior, compared to the hemispherical portion of the vessel interior at its closed end 84, or vice versa. This expedient is particularly contemplated for a syringe barrel or a sample collection tube as described below, in which a lubricity layer or coating might be provided on part or all of the cylindrical portion of the barrel, where the plunger or piston or closure slides, and not elsewhere.

VII.B.1.a. Optionally, the precursor can be provided in the presence, substantial absence, or absence of nitrogen. In one contemplated embodiment, the precursor alone is delivered to the substrate and subjected to PECVD to apply and cure the coating.

VII.B.1.a. Optionally, the precursor can be provided at less than 1 Torr absolute pressure.

VII.B.1.a. Optionally, the precursor can be provided to the vicinity of a plasma emission.

VII.B.1.a. Optionally, the precursor its reaction product can be applied to the substrate at a thickness of 1 to 5000 nm, or 10 to 1000 nm., or 10-200 nm, or 20 to 100 nm.

VII.B.1.a. In any of the above embodiments, the substrate can comprise glass, or a polymer, for example one or more of a polycarbonate polymer, an olefin polymer (for example a cyclic olefin polymer or a polypropylene polymer), or a polyester polymer (for example, a polyethylene terephthalate polymer).

VII.B.1.a. In any of the above embodiments, the plasma is generated by energizing the gaseous reactant containing the precursor with electrodes powered at a RF frequency as defined in this description.

VII.B.1.a. In any of the above embodiments, the plasma is generated by energizing the gaseous reactant containing the precursor with electrodes supplied with sufficient electric power to generate a lubricity layer. Optionally, the plasma is generated by energizing the gaseous reactant containing the precursor with electrodes supplied with an electric power of from 0.1 to 25 W, optionally from 1 to 22 W, optionally from 3 to 17 W, even optionally from 5 to 14 W, optionally from 7 to 11 W, optionally 8 W. The ratio of the electrode power to the plasma volume can be less than 10 W/ml, optionally is from 5 W/ml to 0.1 W/ml, optionally is from 4 W/ml to 0.1 W/ml, optionally from 2 W/ml to 0.2 W/ml. These power levels are suitable for applying lubricity layers to syringes and sample tubes and vessels of similar geometry having a void volume of 1 to 3 mL in which PECVD plasma is generated. It is contemplated that for larger or smaller objects the power applied should be increased or reduced accordingly to scale the process to the size of the substrate.

VII.B.1.a. The coating can be cured, as by polymerizing or crosslinking the coating, or both, to form a lubricated surface having a lower plunger sliding force or breakout force than the untreated substrate. Curing can occur during the application process such as PECVD, or can be carried out or at least completed by separate processing.

VII.B.1.a. Although plasma deposition has been used herein to demonstrate the coating characteristics, alternate deposition methods can be used as long as the chemical composition of the starting material is preserved as much as possible while still depositing a solid film that is adhered to the base substrate.

VII.B.1.a. For example, the coating material can be applied onto the syringe barrel (from the liquid state) by spraying the coating or dipping the substrate into the coating, where the coating is either the neat precursor a solvent-diluted precursor (allowing the mechanical deposition of a thinner coating). The coating optionally can be crosslinked using thermal energy, UV energy, electron beam energy, plasma energy, or any combination of these.

VII.B.1.a. Application of a silicone precursor as described above onto a surface followed by a separate curing step is also contemplated. The conditions of application and curing can be analogous to those used for the atmospheric plasma curing of pre-coated polyfluoroalkyl ethers, a process practiced under the trademark TriboGlide®. More details of this process can be found at http://www.triboglide.com/process.htm.

VII.B.1.a. In such a process, the area of the part to be coated can optionally be pre-treated with an atmospheric plasma. This pretreatment cleans and activates the surface so that it is receptive to the lubricant that is sprayed in the next step.

VII.B.1.a. The lubrication fluid, in this case one of the above precursors or a polymerized precursor, is then sprayed on to the surface to be treated. For example, IVEK precision dispensing technology can be used to accurately atomize the fluid and create a uniform coating.

VII.B.1.a. The coating is then bonded or crosslinked to the part, again using an atmospheric plasma field. This both immobilizes the coating and improves the lubricant's performance.

VII.B.1.a. Optionally, the atmospheric plasma can be generated from ambient air in the vessel, in which case no gas feed and no vacuum drawing equipment is needed. Optionally, however, the vessel is at least substantially closed while plasma is generated, to minimize the power requirement and prevent contact of the plasma with surfaces or materials outside the vessel.

VII.B.1.a.i. Lubricity layer: $SiO_x$ Barrier, Lubricity Layer, Surface Treatment Surface treatment VII.B.1.a.i. Another embodiment is a syringe comprising a barrel defining a lumen and having an interior surface slidably receiving a plunger, i.e. receiving a plunger for sliding contact to the interior surface.

VII.B.1.a.i. The syringe barrel is made of thermoplastic base material.

VII.B.1.a.i. Optionally, the interior surface of the barrel is coated with an $SiO_x$ barrier layer or coating as described elsewhere in this specification.

VII.B.1.a.i. A lubricity layer or coating is applied to the barrel interior surface, the plunger, or both, or to the previously applied $SiO_x$ barrier layer. The lubricity layer or coating can be provided, applied, and cured as set out in embodiment VII.B.1.a or elsewhere in this specification.

VII.B.1.a.i. For example, the lubricity layer or coating can be applied, in any embodiment, by PECVD. The lubricity layer or coating is deposited from an organosilicon precursor, and is less than 1000 nm thick.

VII.B.1.a.i. A surface treatment is carried out on the lubricity layer or coating in an amount effective to reduce the leaching or extractables of the lubricity layer, the thermoplastic base material, or both. The treated surface can thus act as a solute retainer. This surface treatment can result in a skin coating, e.g. a skin coating which is at least 1 nm thick and less than 100 nm thick, or less than 50 nm thick, or less than 40 nm thick, or less than 30 nm thick, or less than 20 nm thick, or less than 10 nm thick, or less than 5 nm thick, or less than 3 nm thick, or less than 2 nm thick, or less than 1 nm thick, or less than 0.5 nm thick.

VII.B.1.a.i. As used herein, "leaching" refers to material transferred out of a substrate, such as a vessel wall, into the contents of a vessel, for example a syringe. Commonly, leachables are measured by storing the vessel filled with intended contents, then analyzing the contents to determine what material leached from the vessel wall into the intended contents. "Extraction" refers to material removed from a substrate by introducing a solvent or dispersion medium other than the intended contents of the vessel, to determine what material can be removed from the substrate into the extraction medium under the conditions of the test.

VII.B.1.a.i. The surface treatment resulting in a solute retainer optionally can be a $SiO_x$ layer or coating as previously defined in this specification or a hydrophobic layer, characterized as defined in the Definition Section. In one embodiment, the surface treatment can be applied by PECVD deposit of $SiO_x$ or a hydrophobic layer. Optionally, the surface treatment can be applied using higher power or stronger oxidation conditions than used for creating the lubricity layer, or both, thus providing a harder, thinner, continuous solute retainer 539. Surface treatment can be less than 100 nm deep, optionally less than 50 nm deep, optionally less than 40 nm deep, optionally less than 30 nm deep, optionally less than 20 nm deep, optionally less than 10 nm deep, optionally less than 5 nm deep, optionally less than 3 nm deep, optionally less than 1 nm deep, optionally less than 0.5 nm deep, optionally between 0.1 and 50 nm deep in the lubricity layer.

VII.B.1.a.i. The solute retainer is contemplated to provide low solute leaching performance to the underlying lubricity and other layers, including the substrate, as required. This retainer would only need to be a solute retainer to large solute molecules and oligomers (for example siloxane monomers such as HMDSO, OMCTS, their fragments and mobile oligomers derived from lubricants, for example a "leachables retainer") and not a gas ($O_2/N_2/CO_2$/water vapor) barrier layer. A solute retainer can, however, also be a gas barrier (e.g. the $SiO_x$ coating according to present invention. One can create a good leachable retainer without gas barrier performance, either by vacuum or atmospheric-based PECVD processes. It is desirable that the "leachables barrier" will be sufficiently thin that, upon syringe plunger movement, the plunger will readily penetrate the "solute retainer" exposing the sliding plunger nipple to the lubricity layer or coating immediately below to form a lubricated surface having a lower plunger sliding force or breakout force than the untreated substrate.

VII.B.1.a.i. In another embodiment, the surface treatment can be performed by oxidizing the surface of a previously applied lubricity layer, as by exposing the surface to oxygen in a plasma environment. The plasma environment described in this specification for forming $SiO_x$ coatings can be used. Or, atmospheric plasma conditions can be employed in an oxygen-rich environment.

VII.B.1.a.i. The lubricity layer or coating and solute retainer, however formed, optionally can be cured at the same time. In another embodiment, the lubricity layer or coating can be at least partially cured, optionally fully cured, after which the surface treatment can be provided, applied, and the solute retainer can be cured.

VII.B.1.a.i. The lubricity layer or coating and solute retainer are composed, and present in relative amounts, effective to provide a breakout force, plunger sliding force, or both that is less than the corresponding force required in the absence of the lubricity layer or coating and surface treatment. In other words, the thickness and composition of the solute retainer are such as to reduce the leaching of material from the lubricity layer or coating into the contents of the syringe, while allowing the underlying lubricity layer or coating to lubricate the plunger. It is contemplated that the solute retainer will break away easily and be thin enough that the lubricity layer or coating will still function to lubricate the plunger when it is moved.

VII.B.1.a.i. In one contemplated embodiment, the lubricity and surface treatments can be applied on the barrel interior surface. In another contemplated embodiment, the lubricity and surface treatments can be applied on the plunger. In still another contemplated embodiment, the lubricity and surface treatments can be applied both on the barrel interior surface and on the plunger. In any of these embodiments, the optional $SiO_x$ barrier layer or coating on the interior of the syringe barrel can either be present or absent.

VII.B.1.a.i. One embodiment contemplated is a plural-layer, e.g. a 3-layer, configuration applied to the inside surface of a syringe barrel. Layer or coating 1 can be an $SiO_x$ gas barrier made by PECVD of HMDSO, OMCTS, or both, in an oxidizing atmosphere. Such an atmosphere can be provided, for example, by feeding HMDSO and oxygen gas to a PECVD coating apparatus as described in this specification. Layer or coating 2 can be a lubricity layer or coating using OMCTS applied in a non-oxidizing atmosphere. Such a non-oxidizing atmosphere can be provided, for example, by feeding OMCTS to a PECVD coating apparatus as described in this specification, optionally in the substantial or complete absence of oxygen. A subsequent solute retainer can be formed by a treatment forming a thin skin layer or coating of $SiO_x$ or a hydrophobic layer or coating as a solute retainer using higher power and oxygen using OMCTS and/or HMDSO.

VII.B.1.a.i. Certain of these plural-layer or coating coatings are contemplated to have one or more of the following optional advantages, at least to some degree. They can address the reported difficulty of handling silicone, since the solute retainer can confine the interior silicone and prevent if from migrating into the contents of the syringe or elsewhere, resulting in fewer silicone particles in the deliverable contents of the syringe and less opportunity for interaction between the lubricity layer or coating and the contents of the syringe. They can also address the issue of migration of the lubricity layer or coating away from the point of lubrication, improving the lubricity of the interface between the syringe barrel and the plunger. For example, the break-free force can be reduced and the drag on the moving plunger can be reduced, or optionally both.

VII.B.1.a.i. It is contemplated that when the solute retainer is broken, the solute retainer will continue to adhere to the lubricity layer or coating and the syringe barrel, which can inhibit any particles from being entrained in the deliverable contents of the syringe.

VII.B.1.a.i. Certain of these coatings will also provide manufacturing advantages, particularly if the barrier coating, lubricity layer or coating and surface treatment are applied in the same apparatus, for example the illustrated PECVD apparatus. Optionally, the $SiO_x$ barrier coating, lubricity layer, and surface treatment can all be applied in one PECVD apparatus, thus greatly reducing the amount of handling necessary.

Further advantages can be obtained by forming the barrier coating, lubricity layer, and solute retainer using the same precursors and varying the process. For example, an $SiO_x$ gas barrier layer or coating can be applied using an OMCTS precursor under high power/high $O_2$ conditions, followed by applying a lubricity layer or coating applied using an OMCTS precursor under low power and/or in the substantial or complete absence of oxygen, finishing with a surface treatment using an OMCTS precursor under intermediate power and oxygen.

VII.B.2. Plungers

VII.B.2.a. With Barrier Coated Piston Front Face

VII.B.2.a. Another embodiment is a plunger for a syringe, including a piston and a push rod. The piston has a front face, a generally cylindrical side face, and a back portion, the side face being configured to movably seat within a syringe barrel. The front face has a barrier coating. The push rod engages the back portion and is configured for advancing the piston in a syringe barrel.

VII.B.2.b. With Lubricity layer or coating Interfacing With Side Face

VII.B.2.b. Yet another embodiment is a plunger for a syringe, including a piston, a lubricity layer, and a push rod. The piston has a front face, a generally cylindrical side face, and a back portion. The side face is configured to movably seat within a syringe barrel. The lubricity layer or coating interfaces with the side face. The push rod engages the back portion of the piston and is configured for advancing the piston in a syringe barrel.

VII.B.3. Two Piece Syringe and Luer Fitting

VII.B.3. Another embodiment is a syringe including a plunger, a syringe barrel, and a Luer fitting. The syringe includes a barrel having an interior surface receiving the plunger for sliding. The Luer fitting includes a Luer taper having an internal passage defined by an internal surface. The Luer fitting is formed as a separate piece from the syringe barrel and joined to the syringe barrel by a coupling. The internal passage of the Luer taper has a barrier coating of $SiO_x$.

VII.B.4. Lubricant Compositions—Lubricity layer or coating Deposited from an Organosilicon Precursor Made By In Situ Polymerizing Organosilicon Precursor VII.B.4.a. Product By Process and Lubricity VII.B.4.a. Still another embodiment is a lubricity layer. This coating can be of the type made by the following process.

VII.B.4.a. Any of the precursors mentioned elsewhere in this specification can be used, alone or in combination. The precursor is applied to a substrate under conditions effective to form a coating. The coating is polymerized or crosslinked, or both, to form a lubricated surface having a lower plunger sliding force or breakout force than the untreated substrate.

VII.B.4.a. Another embodiment is a method of applying a lubricity layer. An organosilicon precursor is applied to a substrate under conditions effective to form a coating. The coating is polymerized or crosslinked, or both, to form a lubricated surface having a lower plunger sliding force or breakout force than the untreated substrate.

VII.B.4.b. Product by Process and Analytical Properties

VII.B.4.b. Even another aspect of the invention is a lubricity layer or coating deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has a density between 1.25 and 1.65 g/cm³ optionally between 1.35 and 1.55 g/cm³, optionally between 1.4 and 1.5 g/cm³, optionally between 1.44 and 1.48 g/cm³ as determined by X-ray reflectivity (XRR).

VII.B.4.b. Still another aspect of the invention is a lubricity layer or coating deposited by PECVD from a feed gas comprising an organometallic precursor, optionally an organosilicon precursor, optionally a linear siloxane, a linear silazane, a monocyclic siloxane, a monocyclic silazane, a polycyclic siloxane, a polycyclic silazane, or any combination of two or more of these. The coating has as an outgas component one or more oligomers containing repeating -(Me)$_2$SiO— moieties, as determined by gas chromatography/mass spectrometry. Optionally, the coating meets the limitations of any of embodiments VII.B.4.a or VII.B.4.b.A.585h. Optionally, the coating outgas component as determined by gas chromatography/mass spectrometry is substantially free of trimethylsilanol.

VII.B.4.b. Optionally, the coating outgas component can be at least 10 ng/test of oligomers containing repeating -(Me)$_2$SiO— moieties, as determined by gas chromatography/mass spectrometry using the following test conditions:

GC Column: 30 m×0.25 mm DB-5MS (J&W Scientific), 0.25 μm film thickness

Flow rate: 1.0 ml/min, constant flow mode

Detector: Mass Selective Detector (MSD)

Injection Mode: Split injection (10:1 split ratio)

Outgassing Conditions: 1½" (37 mm) Chamber, purge for three hour at 85° C., flow 60 ml/min Oven temperature: 40° C. (5 min.) to 300° C. at 10° C./min.; hold for 5 min. at 300° C.

VII.B.4.b. Optionally, the outgas component can include at least 20 ng/test of oligomers containing repeating -(Me)$_2$SiO— moieties.

VII.B.4.b. Optionally, the feed gas comprises a monocyclic siloxane, a monocyclic silazane, a polycyclic siloxane, a polycyclic silazane, or any combination of two or more of these, for example a monocyclic siloxane, a monocyclic silazane, or any combination of two or more of these, for example octamethylcyclotetrasiloxane.

VII.B.4.b. The lubricity layer or coating of any embodiment can have a thickness measured by transmission electron microscopy (TEM) between 1 and 500 nm, optionally between 10 and 500 nm, optionally between 20 and 200 nm, optionally between 20 and 100 nm, optionally between 30 and 100 nm.

VII.B.4.b. Another aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas. Optionally, the coating meets the limitations of embodiments VII.B.4.a or VII.B.4.b.A.

VII.B.4.b. Optionally, the atomic concentration of carbon increases by from 1 to 80 atomic percent (as calculated and based on the XPS conditions in Example 15), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

VII.B.4.b. An additional aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. Optionally, the coating meets the limitations of embodiments VII.B.4.a or VII.B.4.b.A.

VII.B.4.b. Optionally, the atomic concentration of silicon decreases by from 1 to 80 atomic percent (as calculated and based on the XPS conditions in Example 15), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

VII.B.4.b. Lubricity layers having combinations of any two or more properties recited in Section VII.B.4 are also expressly contemplated.

VII.C. Vessels Generally

VII.C. A coated vessel or container as described herein and/or prepared according to a method described herein can be used for reception and/or storage and/or delivery of a compound or composition. The compound or composition can be sensitive, for example air-sensitive, oxygen-sensitive, sensitive to humidity and/or sensitive to mechanical influences. It can be a biologically active compound or composition, for example a medicament like insulin or a composition comprising insulin. In another aspect, it can be a biological fluid, optionally a bodily fluid, for example blood or a blood fraction. In certain aspects of the present invention, the compound or composition is a product to be administered to a subject in need thereof, for example a product to be injected, like blood (as in transfusion of blood from a donor to a recipient or reintroduction of blood from a patient back to the patient) or insulin.

VII.C. A coated vessel or container as described herein and/or prepared according to a method described herein can further be used for protecting a compound or composition contained in its interior space against mechanical and/or chemical effects of the surface of the uncoated vessel material. For example, it can be used for preventing or reducing precipitation and/or clotting or platelet activation of the compound or a component of the composition, for example insulin precipitation or blood clotting or platelet activation.

VII.C. It can further be used for protecting a compound or composition contained in its interior against the environment outside of the vessel, for example by preventing or reducing the entry of one or more compounds from the environment surrounding the vessel into the interior space of the vessel. Such environmental compound can be a gas or liquid, for example an atmospheric gas or liquid containing oxygen, air, and/or water vapor.

VII.C. A coated vessel as described herein can also be evacuated and stored in an evacuated state. For example, the coating allows better maintenance of the vacuum in comparison to a corresponding uncoated vessel. In one aspect of this embodiment, the coated vessel is a blood collection tube. The tube can also contain an agent for preventing blood clotting or platelet activation, for example EDTA or heparin.

VII.C. Any of the above-described embodiments can be made, for example, by providing as the vessel a length of tubing from about 1 cm to about 200 cm, optionally from about 1 cm to about 150 cm, optionally from about 1 cm to about 120 cm, optionally from about 1 cm to about 100 cm, optionally from about 1 cm to about 80 cm, optionally from about 1 cm to about 60 cm, optionally from about 1 cm to about 40 cm, optionally from about 1 cm to about 30 cm long, and processing it with a probe electrode as described below. Particularly for the longer lengths in the above ranges, it is contemplated that relative motion between the probe and the vessel can be useful during coating formation. This can be done, for example, by moving the vessel with respect to the probe or moving the probe with respect to the vessel.

VII.C. In these embodiments, it is contemplated that the coating can be thinner or less complete than can be preferred for a barrier coating, as the vessel in some embodiments will not require the high barrier integrity of an evacuated blood collection tube.

VII.C. As an optional feature of any of the foregoing embodiments the vessel has a central axis.

VII.C. As an optional feature of any of the foregoing embodiments the vessel wall is sufficiently flexible to be flexed at least once at 20° C., without breaking the wall, over a range from at least substantially straight to a bending radius at the central axis of not more than 100 times as great as the outer diameter of the vessel.

VII.C. As an optional feature of any of the foregoing embodiments the bending radius at the central axis is not more than 90 times as great as, or not more than 80 times as great as, or not more than 70 times as great as, or not more than 60 times as great as, or not more than 50 times as great as, or not more than 40 times as great as, or not more than 30 times as great as, or not more than 20 times as great as, or not more than 10 times as great as, or not more than 9 times as great as, or not more than 8 times as great as, or not more than 7 times as great as, or not more than 6 times as great as, or not more than 5 times as great as, or not more than 4 times as great as, or not more than 3 times as great as, or not more than 2 times as great as, or not more than, the outer diameter of the vessel.

VII.C. As an optional feature of any of the foregoing embodiments the vessel wall can be a fluid-contacting surface made of flexible material.

VII.C. As an optional feature of any of the foregoing embodiments the vessel lumen can be the fluid flow passage of a pump.

VII.C. As an optional feature of any of the foregoing embodiments the vessel can be a blood bag adapted to maintain blood in good condition for medical use.

VII.C., VII.D. As an optional feature of any of the foregoing embodiments the polymeric material can be a silicone elastomer or a thermoplastic polyurethane, as two examples, or any material suitable for contact with blood, or with insulin.

VII.C., VII.D. In an optional embodiment, the vessel has an inner diameter of at least 2 mm, or at least 4 mm.

VII.C. As an optional feature of any of the foregoing embodiments the vessel is a tube.

VII.C. As an optional feature of any of the foregoing embodiments the lumen has at least two open ends.

VII.C.1. Vessel Containing Viable Blood, Having a Coating Deposited from an Organosilicon Precursor VII.C.1. Even another embodiment is a blood containing vessel. Several non-limiting examples of such a vessel are a blood transfusion bag, a blood sample collection vessel in which a sample has been collected, the tubing of a heart-lung machine, a flexible-walled blood collection bag, or tubing used to collect a patient's blood during surgery and reintroduce the blood into the patient's vasculature. If the vessel includes a pump for pumping blood, a particularly suitable pump is a centrifugal pump or a peristaltic pump. The vessel has a wall; the wall has an inner surface defining a lumen. The inner surface of the wall has an at least partial coating of a hydrophobic layer, characterized as defined in the Definition Section. The coating can be as thin as monomolecular thickness or as thick as about 1000 nm. The vessel contains blood viable for return to the vascular system of a patient disposed within the lumen in contact with the hydrophobic layer.

VII.C.1. An embodiment is a blood containing vessel including a wall and having an inner surface defining a lumen. The inner surface has an at least partial coating of a hydrophobic layer. The coating can also comprise or consist essentially of $SiO_x$, where x is as defined in this specification. The thickness of the coating is within the range from monomolecular thickness to about 1000 nm thick on the inner surface. The vessel contains blood viable for return to the vascular system of a patient disposed within the lumen in contact with the hydrophobic layer or coating.

VII.C.2. Coating Deposited from an Organosilicon Precursor Reduces Clotting or platelet activation of Blood in the Vessel VII.C.2. Another embodiment is a vessel having a wall. The wall has an inner surface defining a lumen and has an at least partial coating of a hydrophobic layer, where optionally w, x, y, and z are as previously defined in the Definition Section. The thickness of the coating is from monomolecular thickness to about 1000 nm thick on the inner surface. The coating is effective to reduce the clotting or platelet activation of blood exposed to the inner surface, compared to the same type of wall uncoated with a hydrophobic layer.

VII.C.2. It is contemplated that the incorporation of a hydrophobic layer or coating will reduce the adhesion or clot forming tendency of the blood, as compared to its properties in contact with an unmodified polymeric or $SiO_x$ surface. This property is contemplated to reduce or potentially eliminate the need for treating the blood with heparin, as by reducing the necessary blood concentration of heparin in a patient undergoing surgery of a type requiring blood to be removed from the patient and then returned to the patient, as when using a heart-lung machine during cardiac surgery. It is contemplated that this will reduce the complications of surgery involving the passage of blood through such a vessel, by reducing the bleeding complications resulting from the use of heparin.

VII.C.2. Another embodiment is a vessel including a wall and having an inner surface defining a lumen. The inner surface has an at least partial coating of a hydrophobic layer, the thickness of the coating being from monomolecular thickness to about 1000 nm thick on the inner surface, the coating being effective to reduce the clotting or platelet activation of blood exposed to the inner surface.

VII.C.3. Vessel Containing Viable Blood, Having a Coating of Group III or IV Element VII.C.3. Another embodiment is a blood containing vessel having a wall having an inner surface defining a lumen. The inner surface has an at least partial coating of a composition comprising one or more elements of Group III, one or more elements of Group IV, or a combination of two or more of these. The thickness of the coating is between monomolecular thickness and about 1000 nm thick, inclusive, on the inner surface. The vessel contains blood viable for return to the vascular system of a patient disposed within the lumen in contact with the hydrophobic layer.

VII.C.4. Coating of Group III or IV Element Reduces Clotting or Platelet Activation of Blood in the Vessel VII.C.4. Optionally, in the vessel of the preceding paragraph, the coating of the Group III or IV Element is effective to reduce the clotting or platelet activation of blood exposed to the inner surface of the vessel wall.

VII.D. Pharmaceutical Delivery Vessels

VII.D. A coated vessel or container as described herein can be used for preventing or reducing the escape of a compound or composition contained in the vessel into the environment surrounding the vessel.

Further uses of the coating and vessel as described herein, which are apparent from any part of the description and claims, are also contemplated.

VII.D.1. Vessel Containing Insulin, Having a Coating Deposited from an Organosilicon Precursor VII.D.1. Another embodiment is an insulin containing vessel including a wall having an inner surface defining a lumen. The inner surface has an at least partial coating of a hydrophobic layer, characterized as defined in the Definition Section. The coating can be from monomolecular thickness to about 1000 nm thick on the inner surface. Insulin is disposed within the lumen in contact with the $Si_wO_xC_yH_z$ coating.

VII.D.1. Still another embodiment is an insulin containing vessel including a wall and having an inner surface defining a lumen. The inner surface has an at least partial coating of a hydrophobic layer, characterized as defined in the Definition Section, the thickness of the coating being from monomolecular thickness to about 1000 nm thick on the inner surface. Insulin, for example pharmaceutical insulin FDA approved for human use, is disposed within the lumen in contact with the hydrophobic layer.

VII.D.1. It is contemplated that the incorporation of a hydrophobic layer, characterized as defined in the Definition Section, will reduce the adhesion or precipitation forming tendency of the insulin in a delivery tube of an insulin pump, as compared to its properties in contact with an unmodified polymeric surface. This property is contemplated to reduce or potentially eliminate the need for filtering the insulin passing through the delivery tube to remove a solid precipitate.

VII.D.2. Coating Deposited from an Organosilicon Precursor Reduces Precipitation of Insulin in the Vessel VII.D.2. Optionally, in the vessel of the preceding paragraph, the coating of a hydrophobic layer or coating is effective to reduce the formation of a precipitate from insulin contacting the inner surface, compared to the same surface absent the hydrophobic layer.

VII.D.2. Even another embodiment is a vessel again comprising a wall and having an inner surface defining a lumen. The inner surface includes an at least partial coating of a hydrophobic layer. The thickness of the coating is in the range from monomolecular thickness to about 1000 nm thick on the inner surface. The coating is effective to reduce the formation of a precipitate from insulin contacting the inner surface.

VII.D.3. Vessel Containing Insulin, Having a Coating of Group III or IV Element

VII.D.3. Another embodiment is an insulin containing vessel including a wall having an inner surface defining a lumen. The inner surface has an at least partial coating of a composition comprising carbon, one or more elements of Group III, one or more elements of Group IV, or a combination of two or more of these. The coating can be from monomolecular thickness to about 1000 nm thick on the inner surface. Insulin is disposed within the lumen in contact with the coating.

VII.D.4. Coating of Group III or IV Element Reduces Precipitation of Insulin in the Vessel VII.D.4. Optionally, in the vessel of the preceding paragraph, the coating of a composition comprising carbon, one or more elements of Group III, one or more elements of Group IV, or a combination of two or more of these, is effective to reduce the formation of a precipitate from insulin contacting the inner surface, compared to the same surface absent the coating.

Common Conditions for all Embodiments

In any embodiment contemplated here, many common conditions can be used, for example any of the following, in any combination. Alternatively, any different conditions described elsewhere in this specification or claims can be employed.

I. Substrate Disclosure of any Embodiment

I.A. Vessel of any Embodiment

The vessel can be a sample collection tube, for example a blood collection tube, or a syringe, or a syringe part, for example a barrel or piston or plunger; a vial; a conduit; or a cuvette. The substrate can be a closed-ended tube, for example a medical sample collection tube. The substrate can be the inside wall of a vessel having a lumen, the lumen having a void volume of from 0.5 to 50 mL, optionally from 1 to 10 mL, optionally from 0.5 to 5 mL, optionally from 1 to 3 mL. The substrate surface can be part or all of the inner surface of a vessel having at least one opening and an inner surface, and wherein the gaseous reactant fills the interior lumen of the vessel and the plasma can be generated in part or all of the interior lumen of the vessel.

I.B. Syringe and Parts

The substrate can be a syringe barrel. The syringe barrel can have a plunger sliding surface and the coating can be disposed on at least a portion of the plunger sliding surface. The coating can be a lubricity layer. The lubricity layer or coating can be on the barrel interior surface. The lubricity layer or coating can be on the plunger.

I.C. Vessel to Receive Stopper

The substrate can be a stopper receiving surface in the mouth of a vessel. The substrate can be a generally conical or cylindrical inner surface of an opening of a vessel adapted to receive a stopper.

I.D. Stopper

The substrate can be a sliding surface of a stopper. The substrates can be coated by providing a multiplicity of the stoppers located in a single substantially evacuated vessel. The chemical vapor deposition can be plasma-enhanced chemical vapor deposition and the stopper can be contacted with the plasma. The chemical vapor deposition can be plasma-enhanced chemical vapor deposition. The plasma can be formed upstream of the stopper, producing plasma product, and the plasma product can be contacted with the stopper.

A closure can define a substrate coated with a coating, optionally a stopper coated with a lubricity layer. The substrate can be a closure seated in a vessel defining a lumen and a surface of the closure facing the lumen can be coated with the coating.

The coating can be effective to reduce the transmission of a metal ion constituent of the stopper into the lumen of the vessel.

I.E. The Substrate of any Embodiment

The substrate can be a vessel wall. A portion of the vessel wall in contact with a wall-contacting surface of a closure can be coated with the coating. The coating can be a composite of material having first and second layers. The first layer or coating can interface with the elastomeric stopper. The first layer of the coating can be effective to reduce the transmission of one or more constituents of the stopper into the vessel lumen. The second layer or coating can interface with the inner wall of the vessel. The second layer can be effective to reduce friction between the stopper and the inner wall of the vessel when the stopper can be seated on the vessel.

Alternatively, the first and second layers of any embodiment can be defined by a coating of graduated properties containing carbon and hydrogen, in which the proportions of carbon and hydrogen are greater in the first layer or coating than in the second layer.

The coating of any embodiment can be applied by plasma enhanced chemical vapor deposition.

The coating of any embodiment can be between 0.5 and 5000 nm thick, alternatively between 100 and 5000 nm thick, alternatively between 200 and 5000 nm thick, alternatively between 500 and 5000 nm thick, alternatively between 1000 and 5000 nm thick, alternatively between 2000 and 5000 nm thick, alternatively between 3000 and 5000 nm thick, alternatively between 4000 and 10,000 nm thick.

The substrate of any embodiment can comprise glass, alternatively a polymer, alternatively a polycarbonate polymer, alternatively an olefin polymer, alternatively a cyclic olefin polymer, alternatively a polypropylene polymer, alternatively a polyester polymer, alternatively a polyethylene terephthalate polymer, alternatively a polyethylene naphthalate polymer, alternatively a combination, composite or blend of any two or more of the above materials.

II. Gaseous Reactant or Process Gas Limitations of any Embodiment

II.A Deposition Conditions of any Embodiment

The plasma for PECVD, if used, can be generated at reduced pressure and the reduced pressure can be less than 300 mTorr, optionally less than 200 mTorr, even optionally less than 100 mTorr. The physical and chemical properties of the coating can be set by setting the ratio of $O_2$ to the organosilicon precursor in the gaseous reactant, and/or by setting the electric power used for generating the plasma.

II.B. Relative Proportions of Gases of any Embodiment

The process gas can contain this ratio of gases:
from 1 to 6 standard volumes of the precursor;
from 1 to 100 standard volumes of a carrier gas,
from 0.1 to 2 standard volumes of an oxidizing agent.
alternatively this ratio:
from 2 to 4 standard volumes, of the precursor;
from 1 to 100 standard volumes of a carrier gas,
from 0.1 to 2 standard volumes
of an oxidizing agent.
alternatively this ratio:
from 1 to 6 standard volumes of the precursor;
from 3 to 70 standard volumes, of a carrier gas,
from 0.1 to 2 standard volumes of an oxidizing agent.
alternatively this ratio:
from 2 to 4 standard volumes, of the precursor;
from 3 to 70 standard volumes of a carrier gas,
from 0.1 to 2 standard volumes of an oxidizing agent.
alternatively this ratio:
from 1 to 6 standard volumes of the precursor;
from 1 to 100 standard volumes of a carrier gas,
from 0.2 to 1.5 standard volumes of an oxidizing agent.
alternatively this ratio:
from 2 to 4 standard volumes, of the precursor;
from 1 to 100 standard volumes of a carrier gas,
from 0.2 to 1.5 standard volumes of an oxidizing agent.
alternatively this ratio:
from 1 to 6 standard volumes of the precursor;
from 3 to 70 standard volumes of a carrier gas,
from 0.2 to 1.5 standard volumes of an oxidizing agent.
alternatively this ratio:
from 2 to 4 standard volumes of the precursor;
from 3 to 70 standard volumes of a carrier gas,
from 0.2 to 1.5 standard volumes of an oxidizing agent.
alternatively this ratio:
from 1 to 6 standard volumes of the precursor;
from 1 to 100 standard volumes of a carrier gas,
from 0.2 to 1 standard volumes of an oxidizing agent.
alternatively this ratio:
from 2 to 4 standard volumes of the precursor;
from 1 to 100 standard volumes of a carrier gas,
from 0.2 to 1 standard volumes of an oxidizing agent.
alternatively this ratio:
from 1 to 6 standard volumes of the precursor;
from 3 to 70 standard volumes of a carrier gas,
from 0.2 to 1 standard volumes of an oxidizing agent.
alternatively this ratio:
2 to 4 standard volumes, of the precursor;
from 3 to 70 standard volumes of a carrier gas,
from 0.2 to 1 standard volumes of an oxidizing agent.
alternatively this ratio:
from 1 to 6 standard volumes of the precursor;
from 5 to 100 standard volumes of a carrier gas,
from 0.1 to 2 standard volumes of an oxidizing agent.
alternatively this ratio:
from 2 to 4 standard volumes, of the precursor;
from 5 to 100 standard volumes of a carrier gas,
from 0.1 to 2 standard volumes
of an oxidizing agent.
alternatively this ratio:
from 1 to 6 standard volumes of the precursor;
from 10 to 70 standard volumes, of a carrier gas,
from 0.1 to 2 standard volumes of an oxidizing agent.
alternatively this ratio:
from 2 to 4 standard volumes, of the precursor;
from 10 to 70 standard volumes of a carrier gas,
from 0.1 to 2 standard volumes of an oxidizing agent.
alternatively this ratio:
from 1 to 6 standard volumes of the precursor;
from 5 to 100 standard volumes of a carrier gas,
from 0.5 to 1.5 standard volumes of an oxidizing agent.
alternatively this ratio:
from 2 to 4 standard volumes, of the precursor;
from 5 to 100 standard volumes of a carrier gas,
from 0.5 to 1.5 standard volumes of an oxidizing agent.
alternatively this ratio:
from 1 to 6 standard volumes of the precursor;
from 10 to 70 standard volumes, of a carrier gas,
from 0.5 to 1.5 standard volumes of an oxidizing agent.
alternatively this ratio:
from 2 to 4 standard volumes of the precursor;
from 10 to 70 standard volumes of a carrier gas,
from 0.5 to 1.5 standard volumes of an oxidizing agent.
alternatively this ratio:
from 1 to 6 standard volumes of the precursor;
from 5 to 100 standard volumes of a carrier gas,
from 0.8 to 1.2 standard volumes of an oxidizing agent.
alternatively this ratio:
from 2 to 4 standard volumes of the precursor;
from 5 to 100 standard volumes of a carrier gas,
from 0.8 to 1.2 standard volumes of an oxidizing agent.
alternatively this ratio:
from 1 to 6 standard volumes of the precursor;
from 10 to 70 standard volumes of a carrier gas,
from 0.8 to 1.2 standard volumes of an oxidizing agent.
alternatively this ratio:
2 to 4 standard volumes, of the precursor;
from 10 to 70 standard volumes of a carrier gas,
from 0.8 to 1.2 standard volumes of an oxidizing agent.

II.C. Precursor of any Embodiment

The organosilicon compound has previously been described, and can be a linear siloxane, a linear silazane, a monocyclic siloxane, a monocyclic silazane, a polycyclic siloxane, a polycyclic silazane, a polysilsesquioxane a polysilsesquiazane, a silatrane, a silquasilatrane, a silproatrane, an azasilatrane, an azasilquasiatrane, an azasilproatrane, or any combination of two or more of these.

The organosilicon compound can be a monocyclic siloxane, a monocyclic silazane, a polycyclic siloxane, a polycyclic silazane, or any combination of two or more of these.

The organosilicon compound can be a monocyclic siloxane, a monocyclic silazane, or any combination of two or more of these.

The organosilicon compound can be a monocyclic siloxane or any combination of two or more of these.

The organosilicon compound can be hexamethyldisiloxane, octamethyltrisiloxane, decamethyl-tetrasiloxane, hexamethylcyclotrisiloxane, octamethylcyclotetrasiloxane, deca-methylcyclopentasiloxane dodecamethylcyclohexasiloxane, SST-eM01 poly-(methylsilsesquioxane), in which each R can be methyl, SST-3MH1.1 poly(Methyl-Hydridosilsesquioxane), in which 90% of the R groups are methyl and 10% are hydrogen atoms, or a combination of any two or more of these.

The organosilicon compound can comprise octamethylcyclotetrasiloxane (OMCTS). The organosilicon compound for any embodiment can consist essentially of octamethycyclotetrasiloxane (OMCTS). The organosilicon compound for any embodiment can be comprises hexamethyldisiloxane.

The precursor can also include a hydrocarbon. The hydrocarbon can comprise methane, ethane, ethylene, propane, acetylene, or a combination of two or more of these.

The precursor can be delivered at a rate of equal to or less than 6 sccm, optionally equal to or less than 2.5 sccm, optionally equal to or less than 1.5 sccm, optionally equal to or less than 1.25 sccm. Larger vessels or other changes in conditions or scale may require more or less of the precursor. The precursor can be provided at less than 1 Torr absolute pressure.

II.D. Carrier Gas of any Embodiment

The carrier gas can comprise an inert gas, for example argon, helium, xenon, neon, another gas that is inert to the other constituents of the process gas under the deposition conditions, or any combination of two or more of these.

II.E. Oxidizing Gas of any Embodiment

The oxidizing gas can comprise oxygen ($O_2$ and/or $O_3$ (commonly known as ozone)), nitrous oxide, or any other gas that oxidizes the precursor during PECVD at the conditions employed. The oxidizing gas comprises about 1 standard volume of oxygen. The gaseous reactant or process gas can be at least substantially free of nitrogen.

III. Plasma of any Embodiment

The plasma of any PECVD embodiment can be formed in the vicinity of the substrate. The plasma can be a non-hollow-cathode plasma. The non-hollow-cathode plasma can be formed in the vicinity of the substrate. The plasma can be formed from the gaseous reactant at reduced pressure. Sufficient plasma generation power input can be provided to induce coating formation on the substrate.

IV. RF Power of any Embodiment

The precursor can be contacted with a plasma made by energizing the vicinity of the precursor with electrodes powered at a frequency of 10 kHz to 2.45 GHz, alternatively from about 13 to about 14 MHz.

The precursor can be contacted with a plasma made by energizing the vicinity of the precursor with electrodes powered at radio frequency, optionally at a frequency of from 10 kHz to less than 300 MHz, optionally from 1 to 50 MHz, even optionally from 10 to 15 MHz, optionally at 13.56 MHz.

The precursor can be contacted with a plasma made by energizing the vicinity of the precursor with electrodes supplied with electric power at from 0.1 to 25 W, optionally from 1 to 22 W, optionally from 1 to 10 W, even optionally from 1 to 5 W, optionally from 2 to 4 W, for example of 3 W, optionally from 3 to 17 W, even optionally from 5 to 14 W, for example 6 or 7.5 W, optionally from 7 to 11 W, for example of 8 W.

The precursor can be contacted with a plasma made by energizing the vicinity of the precursor with electrodes supplied with electric power density at less than 10 W/ml. of plasma volume, alternatively from 5 W/ml. to 0.1 W/ml. of plasma volume, alternatively from 4 W/ml. to 0.1 W/ml. of plasma volume, alternatively from 2 W/ml to 0.2 W/ml. of plasma volume.

The plasma can be formed by exciting the reaction mixture with electromagnetic energy, alternatively microwave energy.

V. Other Process Options of any Embodiment

The applying step for applying a coating to the substrate can be carried out by vaporizing the precursor and providing it in the vicinity of the substrate.

The chemical vapor deposition employed can be PECVD and the deposition time can be from 1 to 30 sec, alternatively from 2 to 10 sec, alternatively from 3 to 9 sec. The purposes for optionally limiting deposition time can be to avoid overheating the substrate, to increase the rate of production, and to reduce the use of process gas and its constituents. The purposes for optionally extending deposition time can be to provide a thicker coating for particular deposition conditions.

VI. Coating Properties of any Embodiment

VI.A. Lubricity Properties of any Embodiment

An embodiment can be carried out under conditions effective to form a lubricated surface of the substrate having a lower sliding force or breakout force (or optionally both) than the untreated substrate. Optionally, the materials and conditions can be effective to reduce the sliding force or breakout force at least at least 25 percent, alternatively at least 45 percent, alternatively at least 60 percent, alternatively more than 60 percent relative to an uncoated syringe barrel. Expressed otherwise, the coating can have a lower frictional resistance than the uncoated surface, wherein optionally the frictional resistance can be reduced by at least 25%, optionally by at least 45%, even optionally by at least 60% in comparison to the uncoated surface.

VI.B. Hydrophobicity Properties of any Embodiment

An embodiment can be carried out under conditions effective to form a hydrophobic layer or coating on the substrate. Optionally, the hydrophobic characteristics of the coating can be set by setting the ratio of the $O_2$ to the organosilicon precursor in the gaseous reactant, and/or by setting the electric power used for generating the plasma. Optionally, the coating can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the coating can be more hydrophobic than the uncoated surface.

VI.C. Thickness of any Embodiment

Optionally, the coating can have a thickness determined by transmission electron microscopy (TEM), of any amount stated in this disclosure.

VI.D. Composition of any Embodiment

Optionally, the coating can be composed of $Si_wO_xC_yH_z$ or $Si_wN_xC_yH_z$, where w can be 1, x can be from about 0.5 to 2.4, y can be from about 0.6 to about 3, and z can be from 2 to about 9. Alternatively, w can be 1, x can be from about 0.5 to 1, y can be from about 2 to about 3, and z can be from 6 to about 9. Alternatively, the coating can have atomic concentrations normalized to 100% carbon, oxygen, and silicon, as determined by X-ray photoelectron spectroscopy (XPS) of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon, normalized to 100% of carbon, oxygen, and silicon, as determined by X-ray photoelectron spectroscopy (XPS), can be greater than the atomic concentration of carbon in the atomic formula for the feed gas. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the coating can be increased in comparison to the organosilicon precursor, and/or the atomic ratio of oxygen to silicon can be decreased in comparison to the organosilicon precursor.

Optionally, the coating can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a coating is contemplated that can be characterized by a sum formula wherein the atomic ratio C:O can be increased and/or the atomic ratio Si:O can be decreased in comparison to the sum formula of the organosilicon precursor.

VI.E. Outgassing Species of any Embodiment

The lubricity coating can have as an outgas component one or more oligomers containing repeating -(Me)2SiO— moieties, as determined by gas chromatography/mass spectrometry. The coating outgas component can be determined by gas chromatography/mass spectrometry. For example, the coating outgas component can have at least 10 ng/test of oligomers containing repeating -(Me)2SiO— moieties, alternatively at least 20 ng/test of oligomers containing repeating -(Me)2SiO— moieties, as determined using the following test conditions:

3. GC Column: 30 m×0.25 mm DB-5MS (J&W Scientific), 0.25 μm film thickness
Flow rate 1.0 ml/min, constant flow mode
Detector: Mass Selective Detector (MSD)
Injection Mode: Split injection (10:1 split ratio)
Outgassing Conditions: 1½" (37 mm) Chamber, purge for three hour at 85° C., flow 60 ml/min
Oven temperature: 40° C. (5 min.) to 300° C. @10° C./min.; hold for 5 min. at 300° C.

Optionally, the lubricity coating can have an outgas component at least substantially free of trimethylsilanol.

VI.E. Other Coating Properties of any Embodiment

The coating can have a density between 1.25 and 1.65 g/cm3, alternatively between 1.35 and 1.55 g/cm3, alternatively between 1.4 and 1.5 g/cm3, alternatively between 1.4 and 1.5 g/cm3, alternatively between 1.44 and 1.48 g/cm3, as determined by X-ray reflectivity (XRR). Optionally, the organosilicon compound can be octamethylcyclotetrasiloxane and the coating can have a density which can be higher than the density of a coating made from HMDSO as the organosilicon compound under the same PECVD reaction conditions.

The coating optionally can prevent or reduce the precipitation of a compound or component of a composition in contact with the coating, for example a coating containing a protein, peptide, or DNA strand, and in particular can prevent or reduce insulin precipitation or blood clotting, in comparison to the uncoated surface and/or to a barrier coated surface using HMDSO as precursor.

The substrate can be a vessel, for protecting a compound or composition contained or received in the coated vessel against mechanical and/or chemical effects of the surface of the uncoated substrate.

The substrate can be a vessel, for preventing or reducing precipitation and/or clotting of a compound or a component of the composition in contact with the interior surface of the vessel. The compound or composition can be a biologically active compound or composition, for example a medicament, for example the compound or composition can comprise insulin, wherein insulin precipitation can be reduced or prevented. Alternatively, the compound or composition can be a biological fluid, for example a bodily fluid, for example blood or a blood fraction wherein blood clotting can be reduced or prevented.

VII. Plus $SiO_x$ Coating, Optional for any Embodiment

The coating on a substrate, for example a vessel wall, as well as comprising a lubricity coating, additionally can comprise at least one layer or coating of $SiO_x$, wherein x can be from 1.5 to 2.9, adjacent to the coating on the substrate, alternatively between the coating and the substrate, alternatively on the opposite side of the coating as the substrate. Optionally, the layers of $SiO_x$ and the coating can either form a sharp interface or a graded composite of $Si_wO_xC_yH_z$ to $SiO_x$ or vice versa. The substrate coated with a lubricity coating can further comprise a surface treatment of the coating in an amount effective to reduce the leaching of the coating, the substrate, or both. For example, the coating and surface treatment can be composed and present in relative amounts effective to provide a breakout force, sliding force, or both less than the corresponding force required in the absence of the coating and surface treatment. Optionally, the surface treatment can be less than 100 nm deep, alternatively less than 50 nm deep, alternatively less than 40 nm deep, alternatively less than 30 nm deep, alternatively less than 20 nm deep, alternatively less than 10 nm deep, alternatively less than 5 nm deep, alternatively less than 3 nm deep, alternatively less than 1 nm deep, alternatively less than 0.5 nm deep in the lubricity layer. As another contemplated option, the surface treatment can be between 0.1 and 50 nm deep in the lubricity layer.

The optional surface treatment can comprise $SiO_x$, in which x can be from about 1.5 to about 2.9. Optionally, at least a second layer or coating of $SiO_x$, wherein x can be from 1.5 to 2.9, can be applied between the coating and the substrate surface.

Embodiments are contemplated in which the substrate is a vessel having an interior surface defining a lumen and an exterior surface. The lubricity coating can be on the interior surface of the vessel, and the vessel can contain at least one further layer or coating on its exterior surface of $SiO_x$, wherein x can be from 1.5 to 2.9. Alternatively, the further layer or coating on the exterior surface can comprise polyvinylidene chloride (PVDC). The further layer or coating on the exterior surface optionally can be a barrier coating.

VIII. Product Made of Vessel Plus Contents, Optional for any Embodiment

In any embodiment, the substrate can be a vessel having an interior surface defining a lumen and an exterior surface, the coating can be on the interior surface of the vessel, and the vessel can contain a citrate or a citrate containing composition in its lumen.

Plasma Coating Deposition

The new plasma coating technology discussed herein is based on Plasma Enhanced Chemical Vapor Deposition (PECVD). The process utilizes a silicon containing vapor that can be combined with oxygen at reduced pressures (mTorr range—atmospheric pressure is 760 Torr) inside a blood tube or syringe. An electrical field generated at 13.56 MHz [radio frequency range] is then applied between an external electrode and an internal grounded gas inlet to create a plasma. At the pressures and powers that are used to coat tubes and syringes, the plasma process is driven by electron impact ionization, which means the electrons in the process are the driving force behind the chemistry. Specifically, the plasma drives the chemical reaction through electron impact ionization of the silicon containing material [hexamethyldisiloxane (HMDSO and other reactants like octamethylcyclotretrasiloxane (OMCTS)] resulting in a silicon dioxide or $SiO_xC_yH_z$ coating deposited onto the interior surfaces of the tube or syringe. These coatings are on the order of 20 or more nanometers in thickness. HMDSO consists of an Si—O—Si backbone with six (6) methyl groups attached to the silicon atoms. The process breaks the Si—C bonds and (at the surface of the tube or syringe) reacts with oxygen to create silicon dioxide. Since the coating is grown on an atomic basis, dense, conformal coatings with thicknesses of 20-30 nanometers can achieve significant barrier properties. The silicon oxide acts as a physical barrier to gases, moisture, and small organic molecules, and is of greater purity than commercial glasses. OMCTS results in coatings with lubricity or anti-adhesion properties.

The new technology is unique in several aspects:

1. The process utilizes the rigid container as the vacuum chamber. PECVD conventionally uses a secondary vacuum vessel into which the part(s) are loaded and coated. Utilizing the container as a vacuum chamber significantly simplifies the process apparatus and reduces cycle/processing time, and thus manufacturing cost and capital. This approach also reduces scale-up issues since scale-up is as simple as replicating the number of tubes or syringes required to meet the throughput requirements.

2. Radio Frequency excitation of the plasma allows energy to be imparted to the ionized gas with little heating of the part. Unlike microwave excitation energies, typically used in PECVD, which will impart significant energy to water molecules in the part itself, radio frequency will not preferentially heat the polymeric tubes or syringes. Controlled heat absorption is critical to prevent substrate temperature increases approaching plastic glass transition temperatures, causing loss of dimensional integrity (collapse under vacuum).

3. Single layer gas barrier coating—the new technology utilizes a single layer of silicon dioxide directly on the interior surface of the part. Most other barrier technologies (thin film) require at least two layers.

4. Combination barrier-lubricity coatings—the new technology utilizes a combination silicon dioxide/$SiO_xC_yH_z$ coating to provide multiple performance attributes (barrier/lubricity).

5. Gas inlet/electrode configuration—the highly asymmetric design helps to prolong the gas inlet life.

The plasma deposition technology utilizes a simple manufacturing configuration. The system is based on a "puck," which is used in transportation of tubes and syringes in and out of the coating station. The device-puck interface (see FIGS. 1 and 2, below) is critical, since once coating/characterization conditions are established at the pilot scale, there are no scaling issues when moving to full scale production; one simply increases the number of pucks through the same process. The puck is manufactured from a polymeric material (e.g. Delrin™) to provide an electrically insulated base. The tube and syringe are mounted into the puck with the largest opening sealing against an o-ring (mounted in the puck itself). The o-ring provides the vacuum seal between the part and the puck so that the ambient air (principally nitrogen and oxygen with some water vapor) can be removed (pressure reduced) and the process gases introduced. The puck has several key features in addition to the o-ring seal. The puck provides a means of connection to the vacuum pump (which pumps away the atmospheric gases and the by-products of the silicon dioxide reaction), a means of accurately aligning the gas inlet in the part, and a means of providing a vacuum seal between the puck and gas inlet.

For SiO2 deposition, HMDSO and oxygen gases are then admitted into the container through the grounded gas inlet which extends up into the part. At this point, the puck and container are moved into the electrode area. The electrode is constructed from a conductive material (for example copper) and provides a tunnel through which the part passes. The electrode does not make physical contact with the container or the puck and is supported independently. An RF impedance matching network and power supply are connected directly to the electrode. The power supply provides energy (at 13.56 MHz) to the impedance matched network. The RF matching network acts to match the output impedance of the power supply to the complex (capacitive and inductive) impedance of the ionized gases. The matching network delivers maximum power delivery to the ionized gas which ensures deposition of the silicon dioxide coating.

Once the container is coated (as the puck moves the container through the electrode channel—which is stationary), the gases are stopped and atmospheric air (or pure nitrogen) is allowed inside the puck/container to bring it back to atmospheric pressure. At this time, the container can be removed from the puck and moved to the next processing station.

The above describes clearly the means of coating a blood tube, parenteral vial or ampule. Syringes require an additional step before and after loading onto the puck. Since the syringes have opening at both ends (one for connection to a needle and the second for installation of a plunger), the needle end must be sealed prior to coating. The above process allows reaction gases to be admitted into the plastic part interior, an electrical current to pass through the gas inside of the part and a plasma to be established inside the part. The plasma (an ionized composition of the HMDSO or OMCTS and oxygen gases) is what drives the chemistry and the deposition of the plasma coating.

Product Specifications/Plasma-Coated Plastic Evacuated Blood Collection Tubes

It is established in the evacuated blood collection tube ("tubes") industry that plastic tube replacement of glass tubes in the mid-1980's is driven by the improved safety benefits of plastic tubes. While eliminating glass tube breakage and reducing blood exposure to phlebotomists, analysts, and patients, plastic tubes did not, and currently do not, match glass tubes in almost all medical performance categories. It is the purpose of this plasma-coated tube technology ("plasma coating") to impart significantly improved performance relative to incumbent plastic tubes, and in some key areas, match (or exceed) glass tube performance.

Incumbent tubes are predominantly comprised of injection-molded grade polyethylene terephthalate (PET) plastic in sizes 13×75 mm, 13×100 mm, and 16×100 mm. Some tubes (containing sodium citrate additives) are PET/PP multilayer compositions for purposes of improved moisture retention, and a minor number of glass tubes are still required for trace metal analysis due to unacceptable performance of plastic tubes. The plasma coating technology will replace the current tube market (Glass, PET) with a single plasma-coated PET tube composition offering for all evacuated blood tube products. For the sodium citrate tube, a glass tube or a 2-walled PET/PP tube is currently used in the marketplace. These tubes will be replaced with a single plasma-coated COP or PP tube composition.

A compromise in plastic tube versus glass tube performance relates to maintenance of partial vacuum inside the tube assemblies, which is required to maintain appropriate blood draw volumes critical to accurate blood analysis. Based on NCCLS standards, when an evacuated blood tube looses 10% of its initial blood draw capability, it is considered unacceptable for use and should be discarded. PET (or PET/PP)-based tubes typically claim a shelf life of 6-18 months from manufacture. Glass tubes, with their improved gas barrier performance, claim a shelf life of 24-36 months. The plasma coating technology has been shown to extend the shelf life of PET-based tubes to 24-36 months, matching the glass standard. Using accelerated aging methods, a 36-month shelf life has been demonstrated with plasma coated tubes.

PET is synthesized via condensation polymerization of terephthalic acid and ethylene glycol using antimony or titanium catalysts. While present in low levels, these metals have potential to interfere with trace metal analysis. Additionally, all PET contains varying trace levels of acetaldehyde, which has been demonstrated to migrate into aqueous fluid media from the plastic. With plasma coating technology, the $SiO_2$ coating, derived entirely from non-metal gaseous precursors [hexamethyldisiloxane (HMDSO)], will itself contain no trace metals and function as a barrier to trace metals and organic solutes potentially leaching from the PET into the additives or blood in the tubes. In addition to control of leaching from PET tubes, the same plasma coating technology offers potential to provide a solute barrier for the tube closure, typically an elastomeric plastic composition containing even higher levels of leachable organic oligomers and catalysts.

A negative effect of polymeric surfactant, used in PET plastic tubes for surface wetting, is the presence of low molecular weight oligomers (from polymeric surfactant synthesis). These oligomers can leach into the blood sample (as determined by MALDI-ToFS oligomer analysis) and can affect subsequent clinical analysis. Thus, the use of polymeric surfactants with PET tubes can result in oligomer contamination. The plasma coating technology will provide a glass-like hydrophilic, $SiO_2$ surface on PET offering good wettability and low wall shear blood hemolysis potential without generating issues relating to polymeric surfactant oligomer leaching.

Physical analysis of saline-tube extracts using ICP-MS (total extractible elemental silicon analysis) have validated no elemental silicon extraction from the $SiO_2$ plasma coating. Subsequent clinical analysis studies will validate these physical improvements.

Table 1 (Appendix) summarizes the incumbent product issues, plasma coating technology improvements, and impact to evacuated blood collection tube devices.

Product Specifications/Plasma-Coated Plastic Vials and Pre-Fill Syringes

The PECVD coating can be applied to plastic-injectable drug packaging to provide a gas barrier and solute barrier for the drug product.

Vials are small vessels or bottles, especially used to store medication as liquids, powders or lyophilized powders. They can also be sample vessels e.g. for use in autosampler devices in analytical chromatography. A vial can have a tubular shape or a bottle-like shape with a neck. The bottom is usually flat unlike test tubes or sample collection tubes which usually have a rounded bottom. Vials can be made, for example, of plastic (e.g. polypropylene, COC, COP).

Syringes, comprising a barrel holding fluid (for example volumes of 2-20 milliliters) with a capillary neck to permit injection needle attachment, are used for administration of synthetic and biological drugs and pharmaceuticals. Historically, syringes have been all glass construction to leverage glass' inertness and barrier performance. Glass barrel/plunger combinations are highly precision machined, so as to prevent leakage, and expensive to manufacture. Driven by cost reduction, plastic plungers comprising a PP plunger with an elastomeric tip have replaced glass plungers, but glass barrels are still the standard, mainly due to concerns over the lack of inertness and barrier performance of plastic barrels for synthetic or biological drug stability.

Separately, issues of trace metal and oxide interaction of glass syringe leachants with biological drugs has warranted consideration of alternative injectable packaging materials. There is a significant market opportunity [cost, weight, and safety (from breakage)] and payload stability to provide a plastic-based package that demonstrates acceptable inertness and barrier performance for the injectable drug market. It is a purpose of this plasma-coated tube technology ("plasma coating") to provide a plasma-coated plastic package, replacing glass packaging for injectable or other liquid drugs, resulting in lower cost, reduced weight, and safer products for the marketplace.

Table 2 (Appendix) lists injectable and other liquid drugs for which the use of plasma-coated plastic packaging is contemplated.

Table 3 (Appendix) lists diagnostic test for which plasma-coated plastic vessels can be used for sample retention.

With utilization of elastomeric-tipped PP plungers and glass barrel syringes, a thick (ca 400+ nanometer) silicone coating is required to reduce both "sticking" friction [resulting from elastomeric and glass contact over time] as well as "sliding" friction during payload injection. Low molecular weight silicones are carried with the payload and delivered into the patient. Efforts to provide a high lubricity, low leachable equivalent have not been realized in the marketplace. It is the purpose of this plasma-coated tube technology ("plasma coating") to provide a plasma coated plastic syringe barrel offering high lubricity, low leachable performance. Work to date indicates use of octamethylcyclotetrasiloxane (OMCTS) plasma-polymerized coatings offers comparable lubricity to silicones. Leaching studies are underway.

For glass syringes, various types of glass have been utilized, including soda glass and borosilicate-type glasses. These glasses, alloys of silica ($SiO_2$) and other metal oxides, can leach metal ions into the syringe fluid contents, affecting the payload stability. Separately, formation of the capillary annulus is accomplished via hot metal wire insertion through the solid capillary. The hot metal wire leaves trace metal residues on the glass which can also affect fluid content stability. In contrast, plasma coating technology utilizes gaseous silicon precursors depositing a metal-free silica or silicon-based coating. The plasma coating technology applied to molded plastic syringe barrels will eliminate traditional glass-based metal contamination issues.

A concern of converting from glass to plastic syringes centers around the potential for leachable materials from plastics. With plasma coating technology, the coating, being derived from non-metal gaseous precursors e.g. HMDSO, will itself contain no trace metals and function as a barrier to inorganic, metals and organic solutes, preventing leaching of these species from the PET into syringe fluids. In addition to leaching control of plastic syringes, the same plasma coating technology offers potential to provide a solute barrier to the plunger tip, typically elastomeric plastic compositions containing even higher levels of leachable organic oligomers and catalysts.

Certain syringes prefilled with synthetic and biological pharmaceutical formulations are very oxygen and moisture sensitive. A critical factor in the conversion from glass to plastic syringe barrels will be the improvement of plastic oxygen and moisture barrier performance. The plasma coating technology is targeted to provide greater improvement in oxygen barrier COP packages. Additional increases in oxygen and moisture barrier performance may be realized combining compatible plasma barrier coatings with other barrier improvement technologies including multilayer, multi-component two-shot syringe compositions and external barrier coatings such as Saran films.

Coated Stoppers and Plungers

A plasma enhanced vapor deposition (PECVD) process has been used for coating rubber stoppers and plunger components that are used in injectable drug packaging (ex. vials, syringes and auto injector cartridges). The process applies a very thin coating of $SiO_x$ to the drug contact surfaces of rubber packaging elements. The $SiO_x$ coating on the rubber prevents materials from leaching into the drug. In addition, the $SiO_x$ coating improves the gas barrier to water and oxygen. The coating is applied selectively, on rubber stoppers and plungers along the areas that are in direct contact with the injectable drug. Since the coating is applied selectively, the coating does not alter the sealing surface, or in the case of syringes, the plunger interaction (movement) with the syringe. Tests are currently being conducted to demonstrate the effectiveness and robustness of the coating to withstand all aspects of injectable drug packaging.

The system approach described herein of plasma coating the plastic container body and rubber components of the injectable drug package provides an inert (pure glass) drug contact surface with significantly improved gas barrier properties, low leaching and lubricity performance; a combination not realized in incumbent products.

Table 4 (Appendix) summarizes the incumbent product issues, and plasma coating technology improvements and impact on prefilled syringe barrel devices.

In-Line Process Coating Validation Methods

For several years, plasma coating technology has been commercially applied to 2D plastic films and 3D plastic containers to improve plastic moisture, oxygen, and carbon dioxide barrier performance, in the food and beverage packaging markets. While 2D plasma coated plastic laminate processes have incorporated optical interference-based thickness measurements as an on-line quality control measure of coating thickness, little on-line development of coating thickness has been realized with beverage containers; instead periodic offline sampling is the norm.

The screening criterion applied in the evaluation and incorporation of in-line coating validation methods for blood tubes and syringe barrels are:

(1) fast [less than 30 seconds (desirably much faster) to accommodate the fast production rates (300+ articles per minute)].

(2) non-destructive (coating/article interrogation without modification).

(3) coating distinguishable [must be able to determine presence (or absence) of 20-40 nanometer thick coating].

(4) correlated to physical or clinical attribute.

(5) available or adaptable to a commercial on-line process (cost effective and adaptable to continuous line operation).

(6) sufficient measurement precision (from one or more methods) to have an alpha risk (allowing out of specification product to pass) equivalent to a six-sigma level of quality, while still maintaining a low enough beta risk (rejecting in-specification product) to be commercially acceptable.

Many methods have been screened (Table 5). The approach which currently best addresses all of these criterion utilizes Microflow Technology (Table 5, A3; FIG. 3). Microflow Technology and sensors demonstrate sensitivity similar to helium detection approaches (mass spectrometry), typically starting from $5\times10^{-7}$ standard cc/second using only air. High sensitivity coupled with fast discrimination offers excellent methodology for coated article verification (FIG. 4). Additionally, this same method can be utilized for traditional leak detection after final product packaging. Work with this kinetic degassing approach is continuing to both correlate with established (but slow) equilibrium oxygen and moisture permeation methods and shorter coating assessment times, currently in the 5-10 second range.

Continued exploration of fast, more sensitive coating assessment methods continues, with investigation, including state of the art microcantilever nanogravemetric methods.

APPENDIX

TABLE 1

Evacuated Blood Collection Tube Devices: Incumbent Product Issues, Plasma Coating Technology Improvements and Impact.

| Incumbent Product (plastic tube device) Issues | Plasma Technology Improvement | Impact |
| --- | --- | --- |
| Blood tube compositions comprise PET plastic, PET/PP laminate plastics, and glass | 20-40 nanometer thick SiO2-coated PET tubes provide a uniform glass-like interface to all additives and blood | Single raw material base for complete product line, reducing raw material inventory, production, and recycle cost |
| Citrate-containing tubes require multiwall tubes (PET/PP) to provide sufficient moisture barrier. | Plasma coating compositions (from hexamethyldisilazane or aceylene (amorhous carbon) may reduce moisture permeabilty rates 50-100% | A plasma-coated plastic composition will reduce production costs. |
| Multiple composition tubes (multiple shot injection or shrink laminates) are difficult to recycle | 20-40 nanometer thick SiO2-coated PET tubes are recyclable | 100 percent raw material utilization (zero waste) will reduce costs |

TABLE 4

Pre-fill Syringe Devices: Incumbnt Product Issues,
Plasma Coating Technology Improvements and Impact.

| Incumbent Product (plastic tube device) Issues | Plasma Technology Improvement | Impact |
|---|---|---|
| Glass syringe barrels are expensive, heavy, and have high potential for breakage resulting in loss of expensive presciption medicines | A plasma-coated plastic syringe barrel will be less expensive, lighter, and more resistant to breakage. | Less expensive, lighter, and more durable prefilled packages will drive growth of the prefill syringe market |
| Glass syringe barrels leach metals into fluid contents | 20-40 nanometer thick plasma SiO2 coated plastic syringe barrels are free of metal content present in traditional glasses | Synthetic and biological drugs and pharmaceuticals will have no metal interactions, extending the assay and shelf life of prefilled syringe products |
| PET syringes permeate oxygen/moisture affecting additive reagent assay levels | 20-40 nanometer thick SiO2-coated PET syringes reduce oxygen permeation rates 300+% | Additive reagent assay levels will be more stable, providing increased clinical analysis reliability |
| PET syringes contains trace metal and organic compositions which can leach into syringe contents | 20-40 nanometer thick SiO2-coated PET tubes reduce (inorganic and organic) leaching rates | Syringe formulations will be more stable, offering improved dose administration accuracy and longer shelf life. |
| Elastomeric tips (sealing the syringe plunger to the barrel) contain trace metal and organic compositions which can leach | Plasma-coated elastomeric closures reduce (inorganic and organic) leaching rates | Syringe formulations will be more stable, offering improved dose administration accuracy and longer shelf life. |
| Silicone fluids for plunger/barrel lubricity demonstrate high leachable levels into pharmaceutical formulations, which are delivered into the blood stream. | Polymeric plasma-coatings on plastic syringes can provide lubricity with reduced leaching leaching | Syringe formulations will be more stable, offering improved dose administration accuracy and longer shelf life. |
| Cyclic olefin copolymer (COC) syringe barrels permeate oxygen affecting additive pharmaceutucal assay levels | 20-40 nanometer thick SiO2-coated plastic syringe barrels reduce oxygen permeation rates 300+% | Syringe formulations will be more stable, offering improved dose administration accuracy and longer shelf life. |

TABLE 5

In-Line Coating Verification Methods.

| | Method | Dection Principle | Detection Mode | Speed | Non-Destructive | Practical | Sensitivity |
|---|---|---|---|---|---|---|---|
| | Mass Transfer | | | | | | |
| | Helium Permeation | differential permeation rates (uncoated/coated) | helium mass spectrometer | − | + | − | +++ |
| A1 | Wall (Air) Diffusion | differential wall diffusion rates (uncoated/coated) | pressure transducer | + | + | ++ | + |
| A2 | Wall (Oxygen) Diffusion | differential wall diffusion rates (uncoated/coated) | fluorescence spectrometer | + | + | ++ | ++ |
| A3 | Wall (Microflow) Diffusion | differential wall diffusion rates (uncoated/coated) | capacitance bridge | + | + | ++ | +++ |
| A4 | Wall (Helium) Diffusion | differential wall diffusion rates (uncoated/coated) | helium mass spectrometer | + | + | − | +++ |
| | Photon Transfer | | | | | | |
| | Reflectance | reflectance (uncoated/coated) | 500-800 nm spectrometer | + | + | − | ++ |
| A5 | Transmission | absorption (uncoated/coated) | 500-800 nm spectrometer | + | + | + | + |
| A6 | Transmission | absorption (SiOxCyHz coated) | 1-10 micron spectrometer | + | + | + | |
| | Electron Transfer | | | | | | |
| | Volume Resistivity | resistance (uncoated/coated) | ohm meter | + | − | − | − |
| A7 | Breakdown Voltage | leakage current (uncoated/coated) | ammeter | + | + | − | − |
| | Sound Wave Transfer | | | | | | |
| | Ultrasonic | frequency shift (uncoated/coated) | ultrasonic dectector | + | + | − | − |

Mass Transfer Rate Methods

Initial efforts are directed toward measurement of gas permeation rates through the plastic article. Knowing that standard (MOCON) oxygen transmission rate (OTR) measurements required 3 and 5+ days for equilibration and gas permeation through a 1 mm thick blood tube, high pressure (100 psi) helium transmission to facilitate faster permeation and offer a very sensitive (helium has 5 ppm natural abundance in air) measurement method for distinguishing pinhole defects is investigated. While fast helium permeation (less than 55 seconds) is realized, the plasma coating is not sufficiently dense to provide a higher resistance than an uncoated tube to helium permeation, thus both coated and uncoated plastic articles exhibited the same permeation rate.

Based on these findings, rather than looking for full permeation through the article, efforts are directed toward investigating inner wall gas depletion (surface diffusion/degassing) rates under a partial vacuum. The principle is to differentiate the rate of gas diffusion from the inner wall of the article, based on the presence or absence of a SiO2 barrier coating.

(A1) Wall (air) Diffusion Rate (pressure change)—Use of pressure transducers offers fast (seconds), high precision determination of air diffusion rate differences between uncoated and coated plastic articles.

(A2) Wall (oxygen) Diffusion Rate (oxygen fluorescence)—Use of fiber optic-based fluorescence detectors (Ocean Optics) offer fast (0.5 seconds), high sensitivity (5× air) determination of oxygen diffusion rate differences between uncoated and coated plastic articles.

(A3) Wall (air) Diffusion Rate (change in gas flow via capacitance measurement)—Use of microflow controllers (Advanced Test Concepts) offer fast, high sensitivity (comparable to helium detection) with surface degassing. This technique may also be incorporated for leak detection for closure/tube vacuum integrity prior to labeling/packaging.

Methods A1-A3 should provide coating coverage determination precision within +/−0.2 percent precision. These methods can be simultaneously operated with respective probe attachments to (the coater hardware) vacuum manifold, and do not require direct interaction with the plastic article/puck system. These wall diffusion rate methods are relative methods and will (a) require either measurement of diffusion rate both before (uncoated) and after (coated) or statistical uncoated tube calibration and (b) correlation to physical (MOCON OTR, Accelerated Aging Water Draw) or clinical data. Method A3 has demonstrated the capability to distinguish between coated and uncoated tubes. One recent finding is that the rate of wall diffusion is greatly affected by the equilibration condition of the PET tube. Therefore it may be critical to maintain a controlled environment for the PET tube prior to testing. Additionally the precision of the test can potentially be improved by increasing the ambient RH that the tubes are exposed to prior to coating and between coating and testing. This will accentuate the difference between a coated and uncoated tube and also increase the diffusion through any small areas of the tube that are either uncoated or the coating is damaged.

Increased sensitivity of the degassing measurement using Microflow can be realized by using a carbon dioxide flush and/or by spiking the test sample with carbon dioxide gas. This is particularly useful when testing COP substrates where the solubility for nitrogen, water and oxygen are low.

Photon Transfer Methods

Photon transfer methods can be broadly grouped into two categories; methods which interrogate a particular area (mm2) on the plastic article and methods which interrogate the overall article, the latter similar to the Mass Transfer methods previously discussed. [Separately, in contrast to glass articles, PET plastic articles have significant absorption bands in the UV (200-400 nm) wavelength range. Both the relative thicknesses of plastic substrate/coating and intrinsic UV absorption of PET plastics make UV wavelength measurement difficult. Visible and Infrared absorptions of SiO2 and $SiO_xC_yH_z$ coating compositions have been investigated.]

Use of reflectance, transmission/absorbance, and fluorescence measurement of coatings for specific area (mm2) detection has been a key method for flat thin films.

With tubes and syringe barrels, the nature of their curved surface and on-line multiple article/puck assemblies make specific area coating detection problematic due to difficulty in reproducible positioning [distance (x), location (y, z) angle (pitch/yaw)]. Also, area detection methods have difficulty to address article thickness transition areas, such as blood tube cylinder-to-bottom sphere interface and molding tip (at bottom of blood tube), and syringe barrel luer adaptor and capillary sections. One the other hand, use of total article detection methods, particularly transmission methods are showing good correlation to mass transfer methods.

(A4) Optical Transmission—Use of fiber optic-based transmission (from 640 nmLED source), a integrating sphere light collector, and visible spectrometer detector (Ocean Optics) offers fast (100 millisecond) coating detection through reduced transmittance of coated tubes relative to uncoated tubes.

This method will be complementary to the mass transfer methods, but not likely have coating coverage determination precision of better than +/−1 percent. This method does require both LED light source and integrating sphere to be in plastic article/puck proximity, but the sphere can be easily lowered and raised onto the tube/puck assembly for measurement. It is envisioned this method would be a multiple station circular array detection approach similar to the coating array.

(A5) Infrared Transmission—Use of fiber optic Near Infrared Detectors will enable area detection of $SiO_xC_yH_z$ lubricity coating compositions on plastic syringe barrels.

Electron Transfer Methods

High resolution analytical techniques (Scanning Electron Microscopy, Scanning Transmission Electron Microscopy) provide highly desirable, nanometer coating thickness characterization, but these are essentially destructive and very costly techniques, not readily adaptable to a fast online process.

Working Examples

Basic Protocols for Forming and Coating Syringe Barrels

The vessels tested in the subsequent working examples are formed and coated according to the following exemplary protocols, except as otherwise indicated in individual examples. Particular parameter values given in the following basic protocols, e.g. the electric power and gaseous reactant or process gas flow, are typical values. Whenever parameter values are changed in comparison to these typical values, this will be indicated in the subsequent working examples. The same applies to the type and composition of the gaseous reactant or process gas. Regardless of tense, these examples are hypothetical unless otherwise indicated expressly.

Protocol for Coating Tube Interior with $SiO_x$

The apparatus as shown in FIG. 1 with the sealing mechanism of FIG. 13, which is a specific contemplated embodiment, is used. The vessel holder 50 is made from Delrin® acetal resin, available from E.I. du Pont de Nemours and Co., Wilmington Del., USA, with an outside diameter of 1.75 inches (44 mm) and a height of 1.75 inches (44 mm). The vessel holder 50 is housed in a Delrin® structure that allowed the device to move in and out of the electrode (160).

The electrode 160 is made from copper with a Delrin® shield. The Delrin® shield is conformal around the outside of the copper electrode 160. The electrode 160 measures approximately 3 inches (76 mm) high (inside) and is approximately 0.75 inches (19 mm) wide.

The tube used as the vessel 80 is inserted into the vessel holder 50 base sealing with Viton® O-rings 490, 504 (Viton® is a trademark of DuPont Performance Elastomers LLC, Wilmington Del., USA) around the exterior of the tube (FIG. 13). The tube 80 is carefully moved into the sealing position over the extended (stationary) ⅛-inch (3-mm) diameter brass probe or counter electrode 108 and pushed against a copper plasma screen.

The copper plasma screen 610 is a perforated copper foil material (K&S Engineering, Chicago Ill., USA, Part #LXMUW5 copper mesh) cut to fit the outside diameter of the tube, and is held in place by a radially extending abutment surface 494 that acted as a stop for the tube insertion (see FIG. 13). Two pieces of the copper mesh are fit snugly around the brass probe or counter electrode 108, insuring good electrical contact.

The brass probe or counter electrode 108 extends approximately 70 mm into the interior of the tube and has an array of #80 wire (diameter=0.0135 inch or 0.343 mm). The brass probe or counter electrode 108 extends through a Swagelok® fitting (available from Swagelok Co., Solon Ohio, USA) located at the bottom of the vessel holder 50, extending through the vessel holder 50 base structure. The brass probe or counter electrode 108 is grounded to the casing of the RF matching network.

The gas delivery port 110 is 12 holes in the probe or counter electrode 108 along the length of the tube (three on each of four sides oriented 90 degrees from each other) and two holes in the aluminum cap that plug the end of the gas delivery port 110. The gas delivery port 110 is connected to a stainless steel assembly comprised of Swagelok® fittings incorporating a manual ball valve for venting, a thermocouple pressure gauge and a bypass valve connected to the vacuum pumping line. In addition, the gas system is connected to the gas delivery port 110 allowing the gaseous reactant or process gases, oxygen and hexamethyldisiloxane (HMDSO) to be flowed through the gas delivery port 110 (under process pressures) into the interior of the tube.

The gas system is comprised of a Aalborg® GFC17 mass flow meter (Part #EW-32661-34, Cole-Parmer Instrument Co., Barrington Ill. USA) for controllably flowing oxygen at 90 sccm (or at the specific flow reported for a particular example) into the process and a polyether ether ketone ("PEEK") capillary (outside diameter, "OD" $\frac{1}{16}$-inch (1.5-mm.), inside diameter, "ID" 0.004 inch (0.1 mm)) of length 49.5 inches (1.26 m). The PEEK capillary end is inserted into liquid hexamethyldisiloxane ("HMDSO," Alfa Aesar® Part Number L16970, NMR Grade, available from Johnson Matthey PLC, London). The liquid HMDSO is pulled through the capillary due to the lower pressure in the tube during processing. The HMDSO is then vaporized into a vapor at the exit of the capillary as it entered the low pressure region.

To ensure no condensation of the liquid HMDSO past this point, the gas stream (including the oxygen) is diverted to the pumping line when it is not flowing into the interior of the tube for processing via a Swagelok® 3-way valve. Once the tube is installed, the vacuum pump valve is opened to the vessel holder 50 and the interior of the tube.

An Alcatel rotary vane vacuum pump and blower comprise the vacuum pump system. The pumping system allows the interior of the tube to be reduced to pressure(s) of less than 200 mTorr while the gaseous reactant or process gases are flowing at the indicated rates.

Once the base vacuum level is achieved, the vessel holder 50 assembly is moved into the electrode 160 assembly. The gas stream (oxygen and HMDSO vapor) is flowed into the brass gas delivery port 110 (by adjusting the 3-way valve from the pumping line to the gas delivery port 110). Pressure inside the tube is approximately 300 mTorr as measured by a capacitance manometer (MKS) installed on the pumping line near the valve that controlled the vacuum. In addition to the tube pressure, the pressure inside the gas delivery port 110 and gas system is also measured with the thermocouple vacuum gauge that is connected to the gas system. This pressure is typically less than 8 Torr.

Once the gas is flowing to the interior of the tube, the RF power supply is turned on to its fixed power level. A ENI ACG-6 600 Watt RF power supply is used (at 13.56 MHz) at a fixed power level of approximately 50 Watts. The output power is calibrated in this and all following Protocols and Examples using a Bird Corporation Model 43 RF Watt meter connected to the RF output of the power supply during operation of the coating apparatus. The following relationship is found between the dial setting on the power supply and the output power: RF Power Out=55×Dial Setting. In the priority applications to the present application, a factor 100 might have been used, and if used is incorrect. The RF power supply is connected to a COMDEL CPMX1000 auto match which matched the complex impedance of the plasma (to be created in the tube) to the 50 ohm output impedance of the ENI ACG-6 RF power supply. The forward power is 50 Watts (or the specific amount reported for a particular example) and the reflected power is 0 Watts so that the applied power is delivered to the interior of the tube. The RF power supply is controlled by a laboratory timer and the power on time set to 5 seconds (or the specific time period reported for a particular example). Upon initiation of the RF power, a uniform plasma is established inside the interior of the tube. The plasma is maintained for the entire 5 seconds until the RF power is terminated by the timer. The plasma produces a silicon oxide coating of approximately 20 nm thickness (or the specific thickness reported in a particular example) on the interior of the tube surface.

After coating, the gas flow is diverted back to the vacuum line and the vacuum valve is closed. The vent valve is then opened, returning the interior of the tube to atmospheric pressure (approximately 760 Torr). The tube is then carefully removed from the vessel holder 50 assembly (after moving the vessel holder 50 assembly out of the electrode 160 assembly).

Protocol for Forming COP Syringe Barrel or Other Drug Containing Vessel

Some non-limiting examples of suitable vessels which can be provided with barrier layers are films or vessels. Some specific contemplated vessels are a syringe barrel, a medical sample collection vessel, a vial, an ampoule, a tube with one end closed and the other end open, for example a blood or other medical sample collection tube.

The vessel can have a thermoplastic wall. The wall can comprise, consist essentially of, or consist of, for example, a thermoplastic material, for example a cyclic olefin polymer (COP).

In any embodiment, the vessel can have a thermoplastic wall made in part of a cyclic olefin polymer, consisting essentially of cyclic olefin polymer, or consisting of a cyclic olefin polymer resin composition. In this embodiment, "consisting of" does not exclude other materials blended with the pure cyclic olefin polymer to make a complete molding composition. This definition of "consisting of" applies throughout this specification, to all materials. "Consisting of" also does not exclude laminar materials having at least one layer consisting of the indicated resin composition and other layers of unlike composition.

COP syringe barrels for a syringe can be used, each having a 2.8 mL overall volume (excluding the Luer fitting) and a nominal 1 mL delivery volume or plunger displacement, Luer adapter type, are injection molded from CZ cyclic olefin polymer (COP) resin, available from Hoechst AG, Frankfurt am Main, Germany, having these dimensions: about 51 mm overall length, 8.6 mm inner syringe barrel diameter and 1.27 mm wall thickness at the cylindrical portion, with an integral 9.5 millimeter length needle capillary Luer adapter molded on one end and two finger flanges molded near the other end.

Protocol for Coating COP Syringe Barrel Interior with $SiO_x$

An injection molded COP syringe barrel can be interior coated with $SiO_x$. The apparatus as shown in FIG. 1 is modified to hold a COP syringe barrel with butt sealing at the base of the COP syringe barrel. Additionally a cap is fabricated out of a stainless steel Luer fitting and a polypropylene cap that seals the end of the COP syringe barrel (illustrated in FIG. 7), allowing the interior of the COP syringe barrel to be evacuated.

The vessel holder 50 can be made from Delrin® with an outside diameter of 1.75 inches (44 mm) and a height of 1.75 inches (44 mm). The vessel holder 50 can be housed in a Delrin® structure that allowed the device to move in and out of the electrode 160.

The electrode 160 can be made from copper with a Delrin® shield. The Delrin® shield can be conformal around the outside of the copper electrode 160. The electrode 160 can be approximately 3 inches (76 mm) high (inside) and approximately 0.75 inches (19 mm) wide. The COP syringe barrel can be inserted into the vessel holder 50, base sealing with an Viton® O-rings.

The COP syringe barrel can be carefully moved into the sealing position over the extended (stationary) ⅛-inch (3-mm.) diameter brass probe or counter electrode 108 and pushed against a copper plasma screen. The copper plasma screen can be a perforated copper foil material (K&S Engineering Part #LXMUW5 Copper mesh) cut to fit the outside diameter of the COP syringe barrel and can be held in place by a abutment surface 494 that acts as a stop for the COP syringe barrel insertion. Two pieces of the copper mesh are fit snugly around the brass probe or counter electrode 108 insuring good electrical contact.

The probe or counter electrode 108 extends approximately 20 mm into the interior of the COP syringe barrel and can be open at its end. The brass probe or counter electrode 108 extends through a Swagelok® fitting located at the bottom of the vessel holder 50, extending through the vessel holder 50 base structure. The brass probe or counter electrode 108 can be grounded to the casing of the RF matching network.

The gas delivery port 110 can be connected to a stainless steel assembly comprised of Swagelok® fittings incorporating a manual ball valve for venting, a thermocouple pressure gauge and a bypass valve connected to the vacuum pumping line. In addition, the gas system can be connected to the gas delivery port 110 allowing the gaseous reactant or process gases, oxygen and hexamethyldisiloxane (HMDSO) to be flowed through the gas delivery port 110 (under process pressures) into the interior of the COP syringe barrel.

The gas system can be comprised of a Aalborg® GFC17 mass flow meter (Cole Parmer Part #EW-32661-34) for controllably flowing oxygen at 90 sccm (or at the specific flow reported for a particular example) into the process and a PEEK capillary (OD 1/16-inch (3-mm) ID 0.004 inches (0.1 mm)) of length 49.5 inches (1.26 m) or other length as indicated in a particular example. The PEEK capillary end can be inserted into liquid hexamethyldisiloxane (Alfa Aesar® Part Number L16970, NMR Grade). The liquid HMDSO can be pulled through the capillary due to the lower pressure in the COP syringe barrel during processing. The HMDSO can be then vaporized into a vapor at the exit of the capillary as it entered the low pressure region.

To ensure no condensation of the liquid HMDSO past this point, the gas stream (including the oxygen) can be diverted to the pumping line when it is not flowing into the interior of the COP syringe barrel for processing via a Swagelok® 3-way valve.

Once the COP syringe barrel is installed, the vacuum pump valve can be opened to the vessel holder 50 and the interior of the COP syringe barrel. An Alcatel rotary vane vacuum pump and blower comprised the vacuum pump system. The pumping system allowed the interior of the COP syringe barrel to be reduced to pressure(s) of less than 150 mTorr while the gaseous reactant or process gases are flowing at the indicated rates. A lower pumping pressure can be achieved with the COP syringe barrel, as opposed to the tube, because the COP syringe barrel has a much smaller internal volume.

After the base vacuum level is achieved, the vessel holder 50 assembly is moved into the electrode 160 assembly. The gas stream (oxygen and HMDSO vapor) is flowed into the brass gas delivery port 110 (by adjusting the 3-way valve from the pumping line to the gas delivery port 110). The pressure inside the COP syringe barrel is approximately 200 mTorr as measured by a capacitance manometer (MKS) installed on the pumping line near the valve that controlled the vacuum. In addition to the COP syringe barrel pressure, the pressure inside the gas delivery port 110 and gas system is also measured with the thermocouple vacuum gauge that is connected to the gas system. This pressure is typically less than 8 Torr.

When the gas is flowing to the interior of the COP syringe barrel, the RF power supply is turned on to its fixed power level. A ENI ACG-6 600 Watt RF power supply is used (at 13.56 MHz) at a fixed power level of approximately 30 Watts. The RF power supply is connected to a COMDEL CPMX1000 auto match that matched the complex impedance of the plasma (to be created in the COP syringe barrel) to the 50 ohm output impedance of the ENI ACG-6 RF power supply. The forward power is 30 Watts (or whatever value is reported in an example) and the reflected power is 0 Watts so that the power is delivered to the interior of the COP syringe barrel. The RF power supply is controlled by a laboratory timer and the power on time set to 5 seconds (or the specific time period reported for a particular example).

Upon initiation of the RF power, a uniform plasma is established inside the interior of the COP syringe barrel. The plasma is maintained for the entire 5 seconds (or other coating time indicated in a specific example) until the RF power is terminated by the timer. The plasma produces a silicon oxide coating of approximately 20 nm thickness (or the thickness reported in a specific example) on the interior of the COP syringe barrel surface.

After coating, the gas flow is diverted back to the vacuum line and the vacuum valve is closed. The vent valve is then opened, returning the interior of the COP syringe barrel to atmospheric pressure (approximately 760 Torr). The COP syringe barrel is then carefully removed from the vessel holder 50 assembly (after moving the vessel holder 50 assembly out of the electrode 160 assembly).

Protocol for Coating COP Syringe Barrel Interior with OMCTS Lubricity Layer or Coating COP syringe barrels as previously identified are interior coated with a lubricity layer. The apparatus as shown in FIG. 1 is modified to hold a COP syringe barrel with butt sealing at the base of the COP syringe barrel. Additionally a cap is fabricated out of a stainless steel Luer fitting and a polypropylene cap that seals the end of the COP syringe barrel (illustrated in FIG. 7). The installation of a Buna-N O-ring onto the Luer fitting allows a vacuum tight seal, allowing the interior of the COP syringe barrel to be evacuated.

The vessel holder 50 is made from Delrin® with an outside diameter of 1.75 inches (44 mm) and a height of 1.75 inches (44 mm). The vessel holder 50 is housed in a Delrin® structure that allows the device to move in and out of the electrode 160.

The electrode 160 is made from copper with a Delrin® shield. The Delrin® shield is conformal around the outside of the copper electrode 160. The electrode 160 measures approximately 3 inches (76 mm) high (inside) and is approximately 0.75 inches (19 mm) wide. The COP syringe barrel is inserted into the vessel holder 50, base sealing with Viton® O-rings around the bottom of the finger flanges and lip of the COP syringe barrel.

The COP syringe barrel is carefully moved into the sealing position over the extended (stationary) ⅛-inch (3-mm.) diameter brass probe or counter electrode 108 and pushed against a copper plasma screen. The copper plasma screen is a perforated copper foil material (K&S Engineering Part #LXMUW5 Copper mesh) cut to fit the outside diameter of the COP syringe barrel and is held in place by a abutment surface 494 that acts as a stop for the COP syringe barrel insertion. Two pieces of the copper mesh are fit snugly around the brass probe or counter electrode 108 insuring good electrical contact.

The probe or counter electrode 108 extends approximately 20 mm (unless otherwise indicated) into the interior of the COP syringe barrel and is open at its end. The brass probe or counter electrode 108 extends through a Swagelok® fitting located at the bottom of the vessel holder 50, extending through the vessel holder 50 base structure. The brass probe or counter electrode 108 is grounded to the casing of the RF matching network.

The gas delivery port 110 is connected to a stainless steel assembly comprised of Swagelok® fittings incorporating a manual ball valve for venting, a thermocouple pressure gauge and a bypass valve connected to the vacuum pumping line. In addition, the gas system is connected to the gas delivery port 110 allowing the gaseous reactant or process gas, octamethylcyclotetrasiloxane (OMCTS) (or the specific gaseous reactant or process gas reported for a particular example) to be flowed through the gas delivery port 110 (under process pressures) into the interior of the COP syringe barrel.

The gas system is comprised of a commercially available Horiba VC1310/SEF8240 OMCTS 10SC 4CR heated mass flow vaporization system that heated the OMCTS to about 100° C. The Horiba system is connected to liquid octamethylcyclotetrasiloxane (Alfa Aesar® Part Number A12540, 98%) through a ⅛-inch (3-mm) outside diameter PFA tube with an inside diameter of ¹⁄₁₆ in (1.5 mm). The OMCTS flow rate is set to 1.25 sccm (or the specific organosilicon precursor flow reported for a particular example). To ensure no condensation of the vaporized OMCTS flow past this point, the gas stream is diverted to the pumping line when it is not flowing into the interior of the COP syringe barrel for processing via a Swagelok® 3-way valve.

Once the COP syringe barrel is installed, the vacuum pump valve is opened to the vessel holder 50 and the interior of the COP syringe barrel. An Alcatel rotary vane vacuum pump and blower comprise the vacuum pump system. The pumping system allows the interior of the COP syringe barrel to be reduced to pressure(s) of less than 100 mTorr while the gaseous reactant or process gases is flowing at the indicated rates. A lower pressure can be obtained in this instance, compared to the tube and previous COP syringe barrel examples, because the overall gaseous reactant or process gas flow rate is lower in this instance.

Once the base vacuum level is achieved, the vessel holder 50 assembly is moved into the electrode 160 assembly. The gas stream (OMCTS vapor) is flowed into the brass gas delivery port 110 (by adjusting the 3-way valve from the pumping line to the gas delivery port 110). Pressure inside the COP syringe barrel can be, for example, approximately 140 mTorr as measured by a capacitance manometer (MKS) installed on the pumping line near the valve that controls the vacuum. In addition to the COP syringe barrel pressure, the pressure inside the gas delivery port 110 and gas system is also measured with the thermocouple vacuum gauge that is connected to the gas system. This pressure is typically less than 6 Torr.

Once the gas is flowing to the interior of the COP syringe barrel, the RF power supply is turned on to its fixed power level. A ENI ACG-6 600 Watt RF power supply is used (at 13.56 MHz) at a fixed power level of approximately 6 Watts (or other power level indicated in a specific example). The RF power supply is connected to a COMDEL CPMX1000 auto match which matched the complex impedance of the plasma (to be created in the COP syringe barrel) to the 50 ohm output impedance of the ENI ACG-6 RF power supply. The forward power is 6 Watts and the reflected power is 0 Watts so that 6 Watts of power (or a different power level delivered in a given example) is delivered to the interior of the COP syringe barrel. The RF power supply is controlled by a laboratory timer and the power on time set to 10 seconds (or a different time stated in a given example).

Upon initiation of the RF power, a uniform plasma is established inside the interior of the COP syringe barrel. The plasma is maintained for the entire coating time, until the RF power is terminated by the timer. The plasma produces a lubricity layer or coating on the interior of the COP syringe barrel surface.

After coating, the gas flow is diverted back to the vacuum line and the vacuum valve is closed. The vent valve is then opened, returning the interior of the COP syringe barrel to atmospheric pressure (approximately 760 Torr). The COP syringe barrel is then carefully removed from the vessel holder 50 assembly (after moving the vessel holder 50 assembly out of the electrode 160 assembly).

Protocol for Coating COP Syringe Barrel Interior with HMDSO Coating

The Protocol for Coating COP Syringe Barrel Interior with OMCTS Lubricity layer or coating is also used for applying an HMDSO coating, except substituting HMDSO for OMCTS.

Protocol for Lubricity Testing

VII.B.1.a. The following materials are used in this test:
Commercial (BD Hypak® PRTC) glass prefillable syringes with Luer-Lok® tip) (ca 1 mL)
COP syringe barrels made according to the Protocol for Forming COP Syringe barrel;
Commercial plastic syringe plungers with elastomeric tips taken from Becton Dickinson Product No. 306507 (obtained as saline prefilled syringes);
Normal saline solution (taken from the Becton-Dickinson Product No. 306507 prefilled syringes);
Dillon Test Stand with an Advanced Force Gauge (Model AFG-50N)
Syringe holder and drain jig (fabricated to fit the Dillon Test Stand)

VII.B.1.a. The following procedure is used in this test.

VII.B.1.a. The jig is installed on the Dillon Test Stand. The platform probe movement is adjusted to 6 in/min (2.5 mm/sec) and upper and lower stop locations are set. The stop locations are verified using an empty syringe and barrel. The commercial saline-filled syringes are labeled, the plungers are removed, and the saline solution is drained via the open ends of the syringe barrels for re-use. Extra plungers are obtained in the same manner for use with the COP and glass barrels.

VII.B.1.a. Syringe plungers are inserted into the COP syringe barrels so that the second horizontal molding point of each plunger is even with the syringe barrel lip (about 10 mm from the tip end). Using another syringe and needle assembly, the test syringes are filled via the capillary end with 2-3 milliliters of saline solution, with the capillary end uppermost. The sides of the syringe are tapped to remove any large air bubbles at the plunger/fluid interface and along the walls, and any air bubbles are carefully pushed out of the syringe while maintaining the plunger in its vertical orientation.

VII.B.1.a. Each filled syringe barrel/plunger assembly is installed into the syringe jig. The test is initiated by pressing the down switch on the test stand to advance the moving metal hammer toward the plunger. When the moving metal hammer is within 5 mm of contacting the top of the plunger, the data button on the Dillon module is repeatedly tapped to record the force at the time of each data button depression, from before initial contact with the syringe plunger until the plunger is stopped by contact with the front wall of the syringe barrel.

VII.B.1.a. All benchmark and coated syringe barrels are run with five replicates (using a new plunger and barrel for each replicate).

VII.B.1.a. COP syringe barrels made according to the Protocol for Forming COP Syringe barrel are coated with an OMCTS lubricity layer or coating according to the Protocol for Coating COP Syringe Barrel Interior with OMCTS Lubricity layer, except at a power of 7.5 Watts, assembled and filled with saline, and tested as described above in this Example for lubricity layers. The polypropylene chamber used per the Protocol for Coating COP Syringe Barrel Interior with OMCTS Lubricity layer or coating allows the OMCTS vapor (and oxygen, if added) to flow through the syringe barrel and through the syringe capillary into the polypropylene chamber (although a lubricity layer or coating might not be needed in the capillary section of the syringe in this instance). Different coating conditions are tested. All of the depositions are completed on COP syringe barrels from the same production batch.

VII.B.1.a. The samples are created by coating COP syringe barrels according to the Protocol for Coating COP Syringe Barrel Interior with OMCTS Lubricity layer. An alternative embodiment of the technology would apply the lubricity layer or coating over another thin film coating, such as $SiO_x$, for example applied according to the Protocol for Coating COP Syringe barrel Interior with $SiO_x$.

EXAMPLES

Examples A-D

Syringe samples are produced as follows. A COP 8007 extended barrel syringe is produced according to the Protocol for Forming COP Syringe Barrel. An $SiO_x$ coating is applied to some of the syringes according to the Protocol for Coating COP Syringe Barrel Interior with $SiO_x$. A lubricity coating is applied to the $_{SiOx}$ coated syringes according to the Protocol for Coating COP Syringe Barrel Interior with OMCTS Lubricity layer, modified as follows. The OMCTS is supplied from a vaporizer, due to its low volatility. Argon carrier gas is used. The process conditions are set to the following:
OMCTS—3 sccm
Argon gas—65 sccm
Oxygen flow—1 sccm
Power—6 watts
Time—10 seconds
The L3 samples are produced without introducing oxygen.

Several syringes are then tested for lubricity using a Genesis Packaging Plunger Force Tester according to the Protocol for Lubricity Testing. Both the initiation force and maintenance forces (in Newtons) are noted relative to an uncoated sample.

Syringes coated with silicone oil are included as a reference since this is the current industry standard.

Examples E-H

Syringe samples are produced as follows. A COP 8007 extended barrel syringe is produced according to the Protocol for Forming COP Syringe Barrel. An $SiO_x$ coating is applied to the syringe barrels according to the Protocol for Coating COP Syringe Barrel Interior with $SiO_x$. A lubricity coating is applied to the $SiO_x$ coated syringes according to the Protocol for Coating COP Syringe Barrel Interior with OMCTS Lubricity layer, modified as follows. The OMCTS is supplied from a vaporizer, due to its low volatility. Argon carrier gas and oxygen are used in some instances. The process conditions are set to the following:
OMCTS—3 sccm (when used)
Argon gas—7.8 sccm (when used)
Oxygen 0.38 sccm (when used)
Power—3 watts
Power on time—10 seconds Syringes E and F prepared under these conditions, Syringes G prepared under these conditions except without a lubricity coating, and Syringes H (commercial syringes coated with silicone oil) are then tested for lubricity using a Genesis Packaging Plunger Force Tester according to the Protocol for Lubricity Testing. Syringes coated with silicone oil are included as a reference since this is the current industry standard.

It is expected under these test conditions that the lubricity coating on Syringes E and F will markedly improve their lubricity compared to Syringes G which lack any lubricity coating. It is expected under these test conditions that the lubricity coating on Syringes E and F also will markedly improve their lubricity compared to Syringes H which contain the standard lubricity coating in the industry.

Syringes E, F, and G are also tested to determine total extractable silicon levels (representing extraction of the organosilicon-based PECVD coatings) using an Inductively Coupled Plasma-Mass Spectrometry (ICP-MS) analysis.

The silicon is extracted using saline water digestion. The tip of each syringe plunger is covered with PTFE tape to prevent extracting material from the elastomeric tip material, then inserted into the syringe barrel base. The syringe barrel is filled with two milliliters of 0.9% aqueous saline solution via a hypodermic needle inserted through the Luer tip of the syringe. This is an appropriate test for extractables because many prefilled syringes are used to contain and deliver saline solution. The Luer tip is plugged with a piece of PTFE beading of appropriate diameter. The syringe is set into a PTFE test stand with the Luer tip facing up and placed in an oven at 50° C. for 72 hours.

Then, either a static or a dynamic mode is used to remove the saline solution from the syringe barrel. According to the static mode, the syringe plunger is removed from the test stand, and the fluid in the syringe is decanted into a vessel. According to the dynamic mode, the Luer tip seal is removed and the plunger is depressed to push fluid through the syringe barrel and expel the contents into a vessel. In either case, the fluid obtained from each syringe barrel is brought to a volume of 50 ml using 18.2MΩ*cm deionized water and further diluted 2× to minimize sodium background during analysis. The CVH barrels contained two milliliters and the commercial barrels contained 2.32 milliliters.

Next, the fluid recovered from each syringe is tested for extractable silicon using Inductively Coupled Plasma-Mass Spectrometry (ICP-MS) Analysis. The instrument: used is a Perkin Elmer Elan DRC II equipped with a Cetac ASX-520 autosampler. The following ICP-MS conditions are employed:
Nebulizer: Quartz Meinhardt
Spray Chamber: Cyclonic
RF (radio frequency) power: 1550 Watts
Argon (Ar) Flow: 15.0 L/min
Auxiliary Ar Flow: 1.2 L/min
Nebulizer Gas Flow: 0.88 L/min
Integration time: 80 sec
Scanning mode: Peak hopping
RPq (The RPq is a rejection parameter) for Cerium as CeO (m/z 156): <2%

Aliquots from aqueous dilutions obtained from Syringes E, F, and G are injected and analyzed for Si in concentration units of micrograms per liter. It is expected under these test conditions that extractables from the lubricity coating will not be clearly higher than the extractables for the $SiO_x$ barrier layer only. Also, it is expected under these test conditions that the static mode will produce far less extractables than the dynamic mode, which is expected.

Examples I-K

Syringe samples I, J, and K, employing three different lubricity coatings, are produced in the same manner as for Examples E-H except as follows:
OMCTS—2.5 sccm
Argon gas—7.6 sccm (when used)
Oxygen 0.38 sccm (when used)
Power—3 watts
Power on time—10 seconds Syringe I has a three-component coating employing OMCTS, oxygen, and carrier gas. Syringe J has a two component coating employing OMCTS and oxygen, but no carrier gas. Syringe K has a one-component coating (OMCTS only). Syringes I, J, and K are then tested for lubricity as described for Examples E-H.

It is expected under these test conditions that Syringe I with a three-component coating employing OMCTS, oxygen, and carrier gas will provide the best lubricity results for both initiation force and maintenance force, Syringe J omitting the carrier gas will yield intermediate results, and Syringe K, having a one-component coating (OMCTS only), will provide the lowest lubricity. In short, it is expected that the addition of both a carrier gas and oxygen to the process gas will improve lubricity under the tested conditions.

Examples L-N

Examples I-K using an OMCTS precursor gas are repeated in Examples L-N, except that HMDSO is used as the precursor in Examples L-N. It is expected under these test conditions that for the tested three-component, two-component, and one-component lubricity coatings, the OMCTS coatings will provide lower resistance, thus better lubricity, than the HMDSO coatings, demonstrating the value of OMCTS as the precursor gas for lubricity coatings.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A package containing a pharmaceutical composition, the package comprising:
   a container comprising a wall defining a lumen, in which at least a portion of the wall defining the lumen comprises a double wall plastic material, in which the double wall material comprises an interior polymer layer enclosed by an exterior polymer layer, in which at least one of the polymer layers is a layer made of a cyclic olefin polymer (COP) resin free of co-monomers;
   a coating on at least a portion of the wall facing the lumen, the coating consisting essentially of a material comprising the atomic ratio $SiO_x$ measured by X-ray photoelectron spectroscopy (XPS), in which x is from 1.5 to 2.9, or a coating comprising the following atomic ratio, measured by XPS, $Si_wO_xC_y$ where w is 1, x in this formula is from about 0.5 to 2.4, and y is from about 0.6 to about 3; and
   a composition contained in the lumen comprising:
   one or more active medicaments which are at least one of a protein, a peptide, or a DNA sequence;
   water; and
   optionally, at least one organic preservative.

2. The package of claim 1, in which the coating comprises a barrier coating of $SiO_x$.

3. The package of claim 2, further comprising, between the barrier coating and the lumen, a second coating or layer having the following atomic ratio, measured by X-ray photoelectron spectroscopy (XPS), $Si_wO_xC_y$ where w is 1, x in this formula is from about 0.5 to 2.4, and y is from about 0.6 to about 3.

4. The package of claim 3, in which the second coating or layer is $Si_wO_xC_y$ applied by chemical vapor deposition, employing as the gaseous reactant or process gas,
   from 1 to 6 standard volumes of an organosilicon precursor,
   from 1 to 100, optionally from 5 to 100, optionally from 10-70 standard volumes of a carrier gas, and
   from 0.1 to 2, optionally from 0.2 to 1.5, optionally from 0.2 to 1, optionally from 0.5 to 1.5, optionally from 0.8 to 1.2 standard volumes of an oxidizing agent.

5. The package of claim 1, comprising an organic preservative.

6. The package of claim 5, in which the organic preservative comprises at least one of m-cresol, benzyl alcohol, and phenol.

7. The package of claim 1, in which the one or more active medicaments comprises pharmaceutical insulin.

8. A medical or diagnostic kit comprising
   the package of claim 1;
   a hypodermic needle, double-ended needle, or other delivery conduit; and
   optionally, an instruction sheet.

9. A method for preparing a pharmaceutical package containing a protein, a peptide, or a DNA sequence, comprising:
providing a container comprising a wall defining a lumen, in which at least a portion of the wall defining the lumen comprises a double wall plastic material;
coating at least a portion of the lumen with a barrier coating consisting essentially of a material comprising the atomic ratio $SiO_x$ measured by X-ray photoelectron spectroscopy (XPS), in which x is from 1.5 to 2.9;
applying between the barrier coating and the lumen, a second coating or layer having the following atomic ratio, measured by XPS, $$Si_wO_xC_y$$

where w is 1, x in this formula is from about 0.5 to 2.4, and y is from about 0.6 to about 3; and
putting a composition into the lumen comprising:
one or more active medicaments which are at least one of a protein, a peptide, or a DNA sequence;
water; and
optionally, at least one organic preservative.

10. The method of claim 9, in which the container further comprises a stopper, plunger or piston and the second coating or layer is a lubricity layer that reduces the friction between the wall facing the lumen and the stopper, plunger or piston.

11. The method of claim 9, in which the barrier coating, the second coating, or a combination comprising the two protects a compound or composition contacting the coating against mechanical and/or chemical effects of the surface of the uncoated vessel material.

12. The method of claim 9, in which the barrier coating, the second coating, or a combination comprising the two is effective for preventing or reducing precipitation and/or clotting or platelet activation of a compound or a component of the composition in contact with the coating.

13. The package of claim 1, in which the one or more active medicaments comprises insulin, and wherein precipitation of the insulin is prevented or reduced.

14. The package of claim 1, in which the one or more active medicaments comprises blood or a blood fraction, and wherein blood clotting or platelet activation is prevented or reduced.

15. The method of claim 9, in which the active medicament is insulin and the container is used for storage of insulin.

16. A package containing a pharmaceutical composition, the package comprising:
a container comprising a wall defining a lumen, in which at least a portion of the wall defining the lumen comprises a cyclic olefin polymer (COP) resin free of co-monomers;
a coating on at least a portion of the wall facing the lumen, the coating consisting essentially of a material comprising the atomic ratio $SiO_x$ measured by X-ray photoelectron spectroscopy (XPS), in which x is from 1.5 to 2.9, or a hydrophobic coating comprising the following atomic ratio, measured by XPS, $$Si_wO_xC_y$$

where w is 1, x in this formula is from about 0.5 to 2.4, and y is from about 0.6 to about 3; and
a composition contained in the lumen comprising:
one or more active medicaments which are at least one of a protein, a peptide, or a DNA sequence;
water; and
optionally, at least one organic preservative.

17. The package of claim 16, in which the hydrophobic coating is applied on top of the $SiO_x$ coating.

* * * * *